(12) United States Patent
McLeod et al.

(10) Patent No.: US 9,402,579 B2
(45) Date of Patent: Aug. 2, 2016

(54) REAL-TIME ASSESSMENT OF ABSOLUTE MUSCLE EFFORT DURING OPEN AND CLOSED CHAIN ACTIVITIES

(75) Inventors: Kenneth J. McLeod, Vestal, NY (US); Jason P. Cole, Ithaca, NY (US)

(73) Assignee: The Research Foundation for the State University of New York, Binghamton, NY (US)

( * ) Notice: Subject to any disclaimer, the term of this patent is extended or adjusted under 35 U.S.C. 154(b) by 558 days.

(21) Appl. No.: 12/701,203

(22) Filed: Feb. 5, 2010

(65) Prior Publication Data

US 2011/0196262 A1 Aug. 11, 2011

(51) Int. Cl.
*A61B 5/22* (2006.01)
*A61B 5/00* (2006.01)

(52) U.S. Cl.
CPC .............. *A61B 5/224* (2013.01); *A61B 5/0053* (2013.01); *A61B 5/411* (2013.01); *A61B 5/726* (2013.01); *A61B 5/7225* (2013.01)

(58) Field of Classification Search
CPC ............. A65B 5/0488; A65B 5/04882; A65B 5/04884; A65B 5/04886; A65B 5/04888; A65B 5/0492; A65B 5/224; A65B 5/7207; A65B 5/721; A65B 5/7214
USPC .......................................... 600/587, 595, 546
See application file for complete search history.

(56) References Cited

U.S. PATENT DOCUMENTS

| | | | |
|---|---|---|---|
| 4,649,934 A | 3/1987 | Fraser et al. | |
| 5,384,725 A | 1/1995 | Coifman et al. | |
| 2004/0263337 A1* | 12/2004 | Terauchi et al. | 340/573.1 |
| 2005/0010139 A1* | 1/2005 | Aminian et al. | 600/595 |
| 2009/0159082 A1* | 6/2009 | Eger | 128/204.23 |
| 2009/0326419 A1* | 12/2009 | Gonzalez Rojas et al. | 600/587 |
| 2010/0137735 A1* | 6/2010 | Hoppe | 600/546 |

OTHER PUBLICATIONS

Watson, G.H. "Introduction to Wavelet Analysis." RTO SCI Lecture Series "Applicaiton of MAthetmatical Signal Processing Techniques to Mission Systems." Monterey USA. Nov. 9-10, 1999.*
G. 0. Matheson, L. Maffey-Ward, M. Mooney, K. Ladly, T. Fung, Y-T. Zhang, "Vibromyography as a quantitative measure of muscle force production," Scand. J. Rehab. Med., vol. 29, pp. 29-35, 1997.
Cole & McLeod (2006) applied time-frequency analysis techniques (Wavelet Packet Analysis—WPA).

(Continued)

*Primary Examiner* — Adam J Eiseman
(74) *Attorney, Agent, or Firm* — Medlen & Carroll, LLP

(57) ABSTRACT

Methods and apparatus based on vibromyography technology are provided that overcome the substantial limitations of current VMG muscle assessment approaches. Specifically, embodiments of the invention provide a means by which clinicians and trainers can perform real-time muscle assessment during typical functional activities (activities involving substantial human movements). In some embodiments, the invention allows the artisan to simultaneously measure muscle forces being generated by complementary, supplementary, and/or antagonistic muscle pairs such that real-time muscle effort ratios can be calculated. In some embodiments, the measurements provide a means by which clinicians and trainers can diagnose musculo-skeletal injuries and pains associated with muscle imbalances.

10 Claims, 43 Drawing Sheets

(56) References Cited

OTHER PUBLICATIONS

C. J. DeLuca, R. S. LeFever, M. P. McCue, A. P. Xenakis, "Behavior of human motor units in different muscles during linearly varying contractions," *J. Physiol*, vol. 329, pp. 113-128, 1982.

R. Merletti, P.A. Parker, *Electromyography: Physiology, Engineering, and noninvasive Applications*. Piscataway, NJ: IEEE Press, 2004, pp. 305-318.

C. Orizio, D. Liberati, C. Locatelli, D. De Grandis, A. Veicsteinas, "Surface mechanomyogram reflects muscle fibres twitches summation," *J. Biomechanics*, vol. 29(4), pp. 475-481, 1996.

Y. Yoshitake, T. Moritane, "The muscle sound properties of different muscle fiber types during voluntary and electrically induced contractions," *J. Electromyog Kinesiol*, vol. 9, pp. 209-217, 1999.

M. Petitjean, B. Maton, "Phonomyogram from single motor units during voluntary isometric contraction," *Eur. J. Appl. Physiol.*, vol. 71, pp. 215-222, 1995.

J. Basmajian, C. De Luca, *Muscles alive*. Baltimore, MD: Waverly Press, Inc, 1985.

K. Akataki, K. Mita, Y. Itoh, "Relationship between mechanomyogram and force during voluntary contractions reinvestigated using spectral decomposition," *Eur. J. Appl. Physiol*, vol. 80, pp. 173-179, 1999.

K. Akataki, K. Mita, M. Watakabe, K. Itoh, "Mechanomyogram and force relationship during voluntary isometric ramp contractions of the biceps brachii muscle," *Eur. J. Appl. Physiol.*, vol. 84, pp. 19-25, 2001.

K. Ebersole, T. Housh, G. Johnson, T. Evetovich, D. Smith, S. Perry, "The effect of leg flexion angle on the mechanomyographic responses to isometric muscle actions," *Eur. I Appl. Physiol. Occup. Physiol.*, vol. 78(3), pp. 264-269, 1998.

D. Denoho, "De-noising by soft-thresholding," *IEEE Trans. Informat. Theory*, vol. 41, pp. 613-627, 1995.

H. Gao, "Choice of thresholds for wavelet shrinkage estimate of the spectrum," *J. Time Series Anal.*, vol. 18, pp. 231-251, 1997.

K. Akataki, K. Mita, Y. Itoh, "Repeatability study of mechanomyography in submaximal isometric contractions using coefficient of variation and interclass correlation coefficient," *Electromyogr. Clin. Neurophysiol.*, vol. 39, pp. 161-166, 1999.

M. Kouzaki, M. Shinohra, T. Fukunaga, "Non-uniform mechanical activity of quadriceps muscle during fatigue by repeated maximal voluntary contraction in humans," *Eur. J. Appl. PhysioL*, vol. 80, pp. 9-15, 1999.

B. Maton, M. Petitjean, J. C. Cnockaert, "Phonomyogram and electromyogram relationships with isometric force reinvestigated in man," *Eu. J. Appl. Physiol.*, vol. 60, pp. 194-201, 1990.

L. J. DeFelice, Introduction to membrane noise. New York, Plenum Press, 1981.

\* cited by examiner

A.
B.
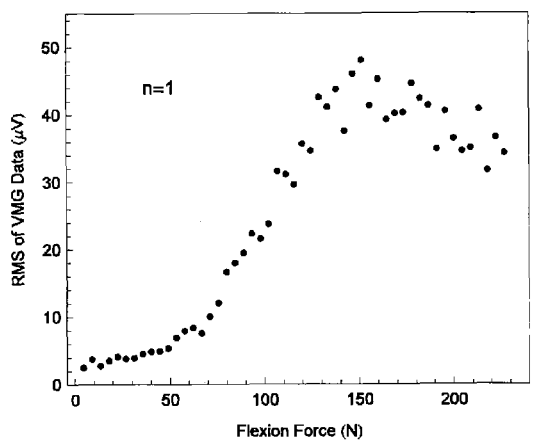
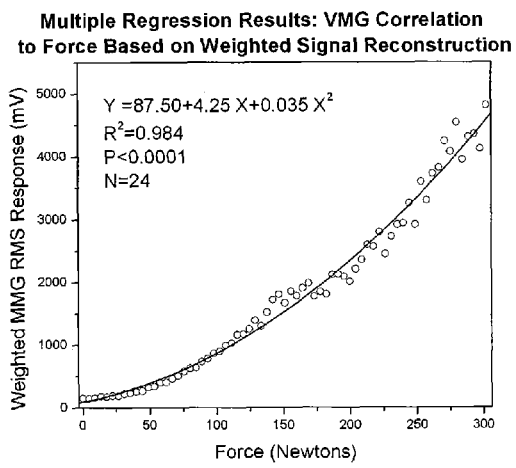
*PRIOR ART*
*PRIOR ART*
FIGURE 1

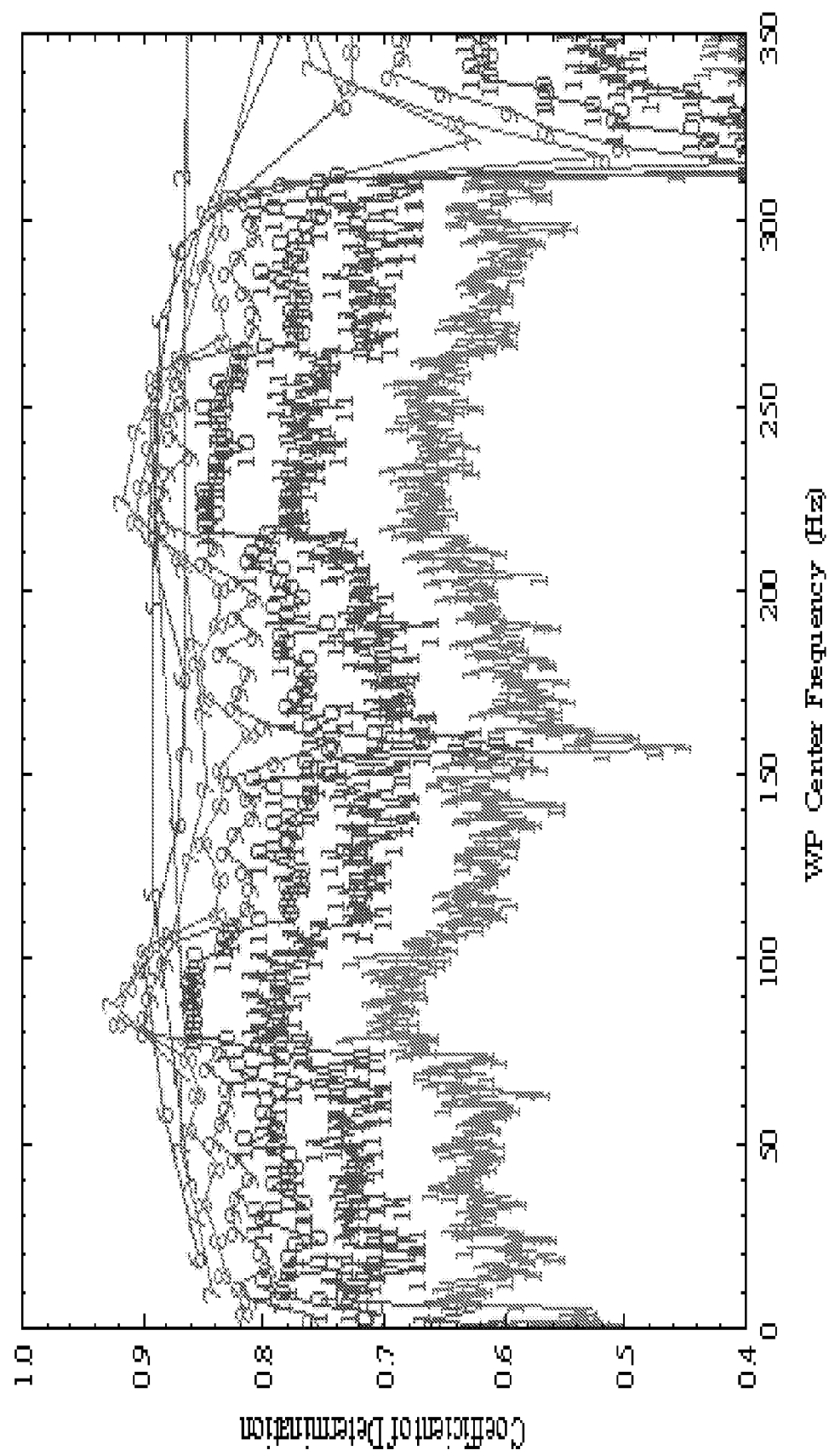
Figure 6A – Wavelet Order 1

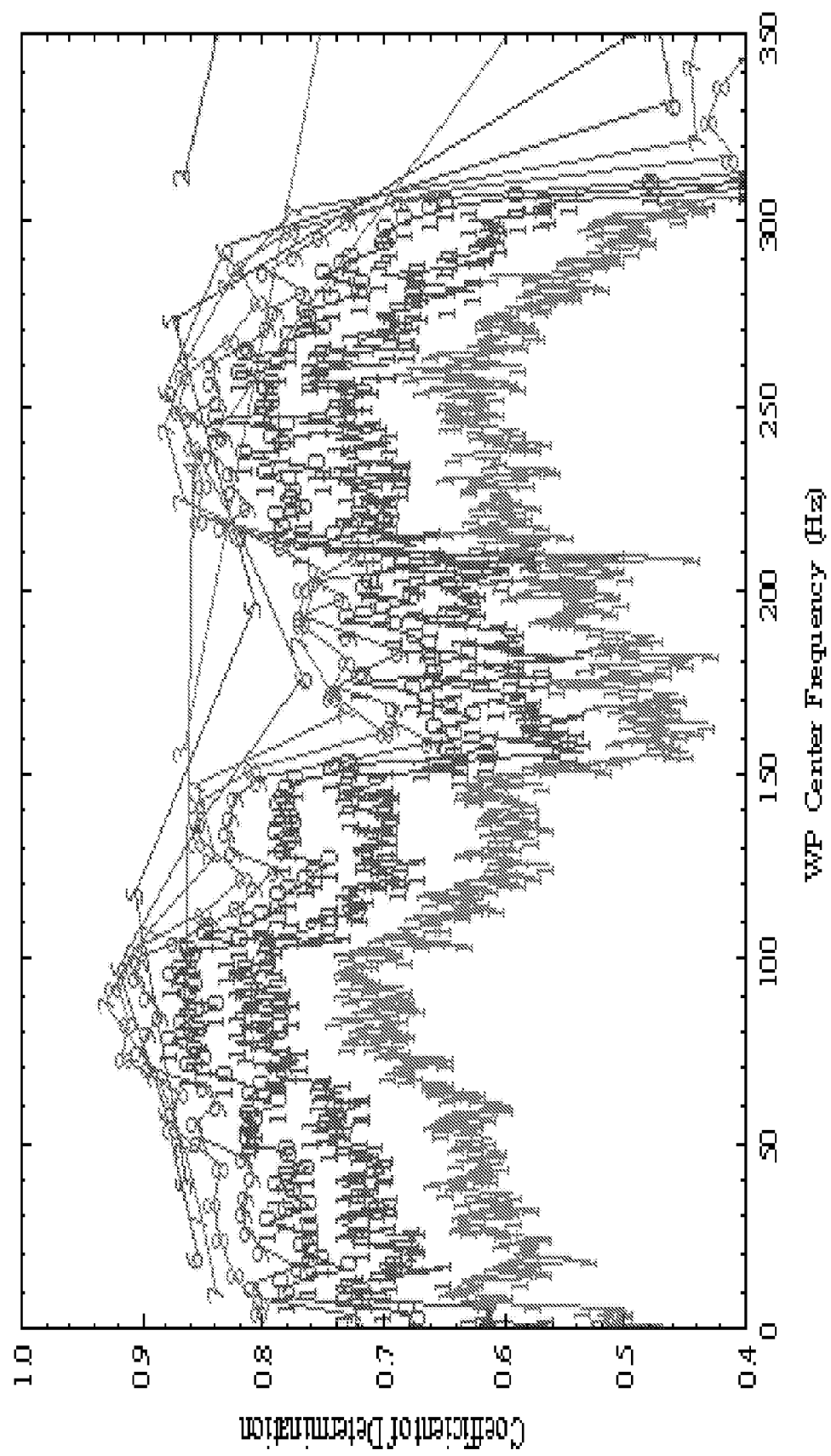
Figure 6B – Wavelet Order 2

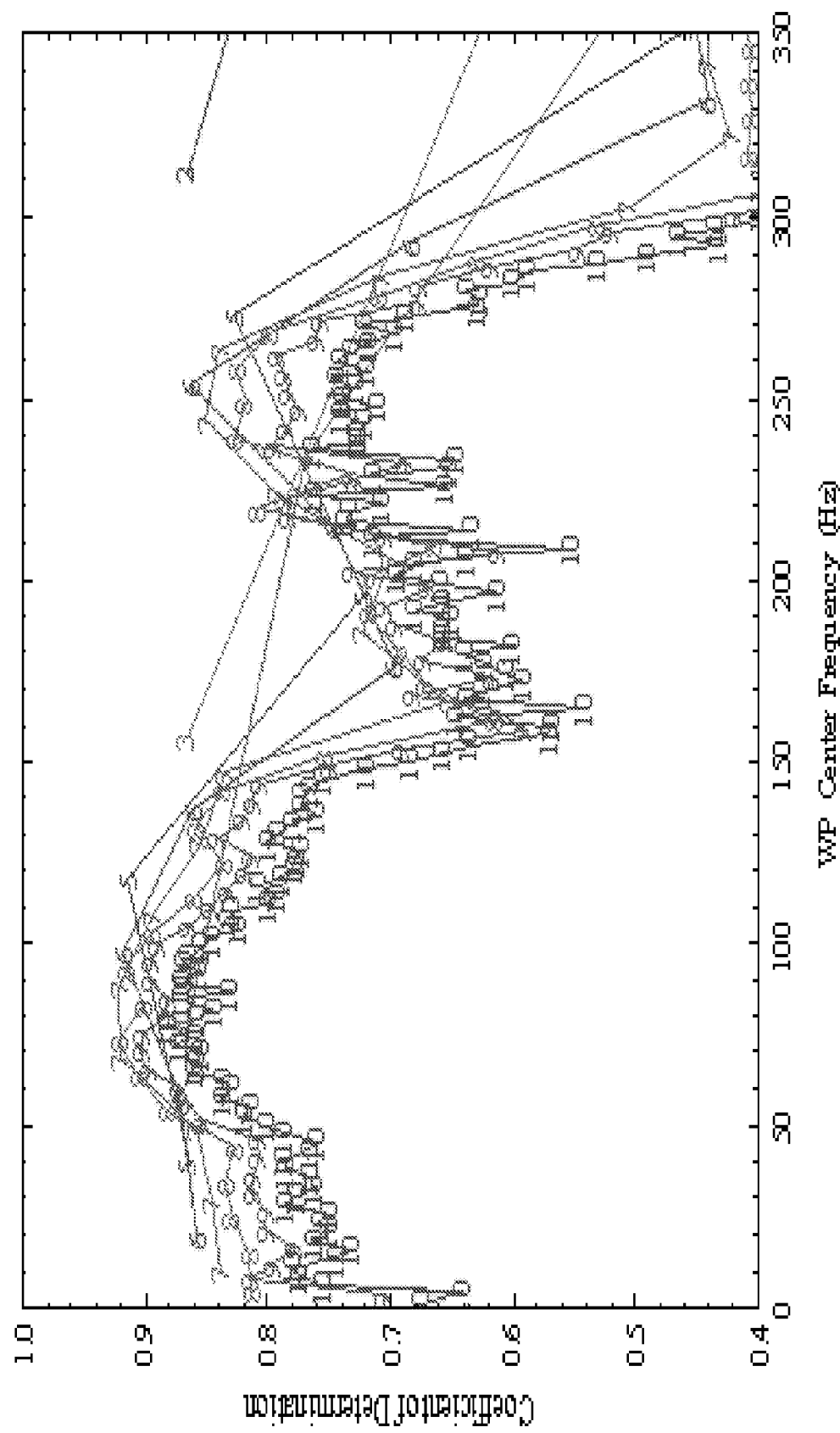
Figure 6C – Wavelet Order 3

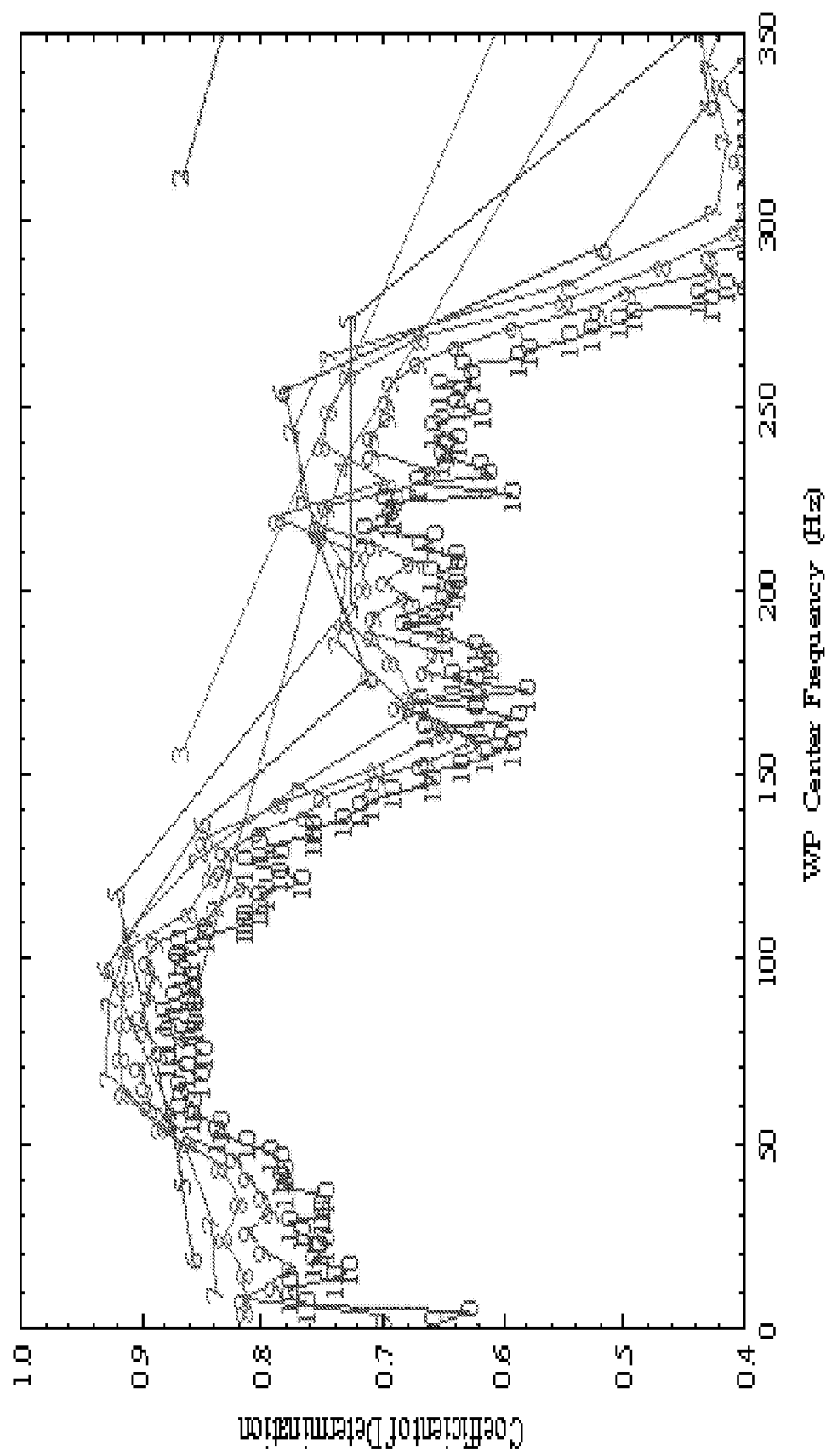
Figure 6D – Wavelet Order 4

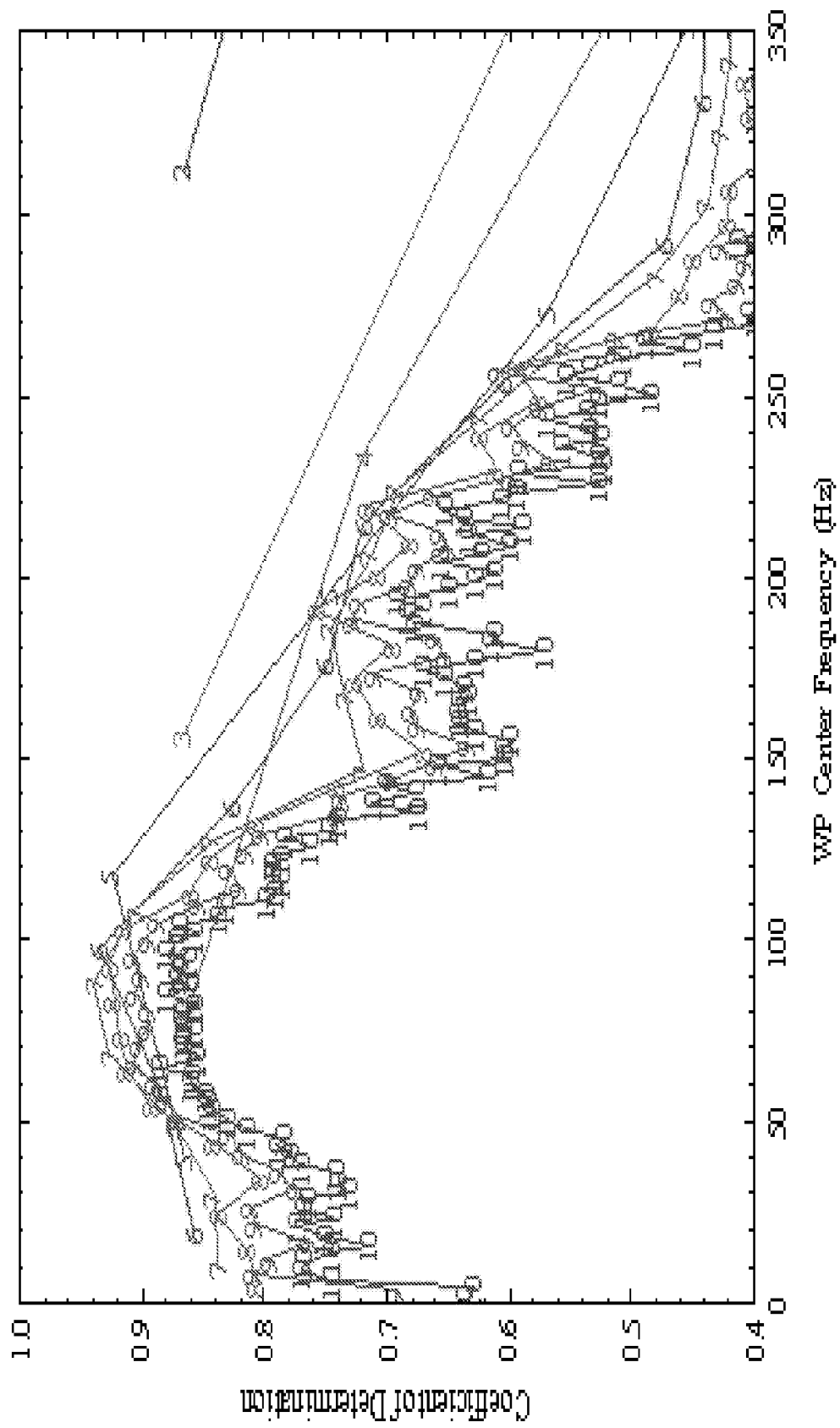

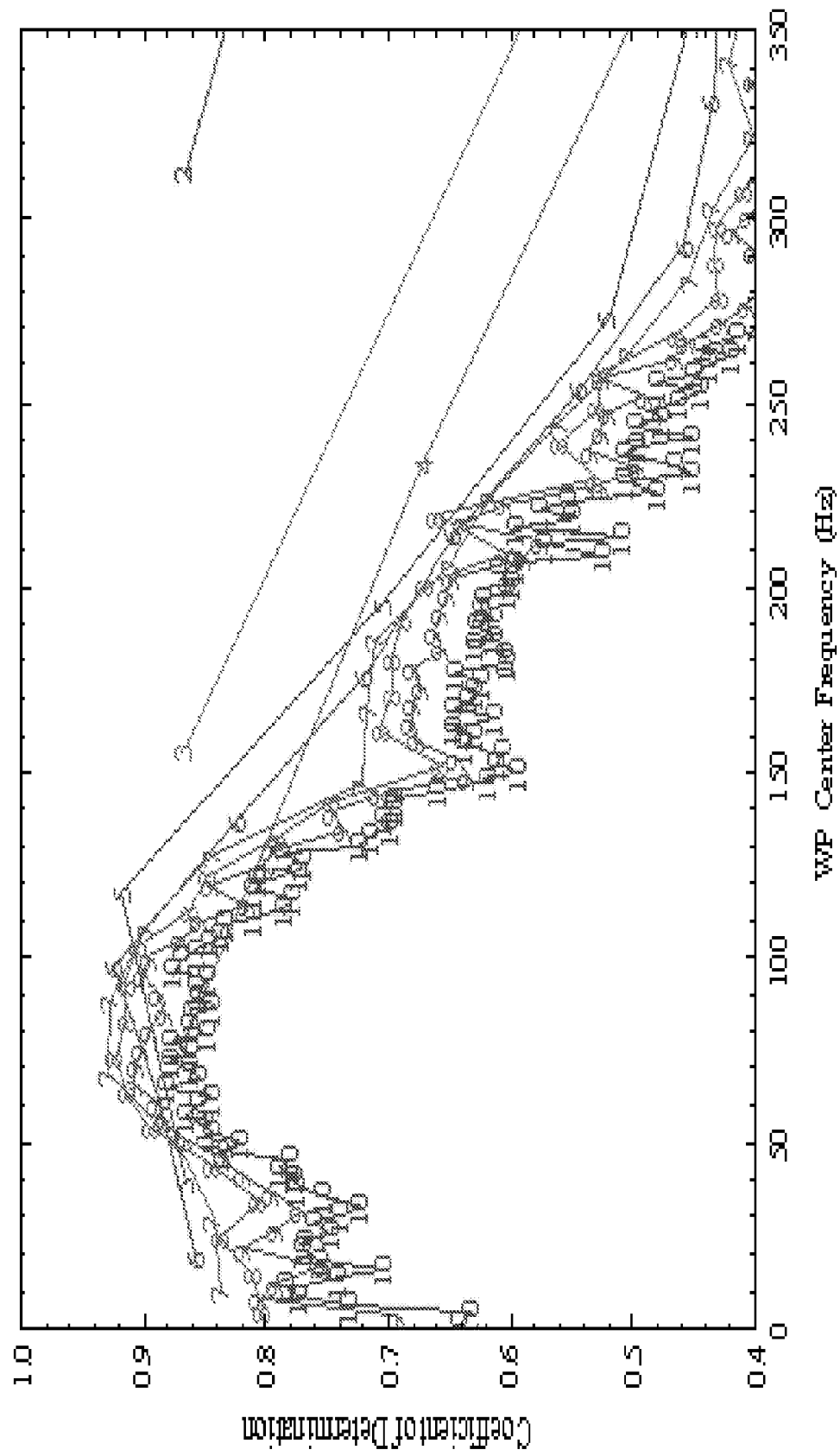
Figure 6F – Wavelet Order 6

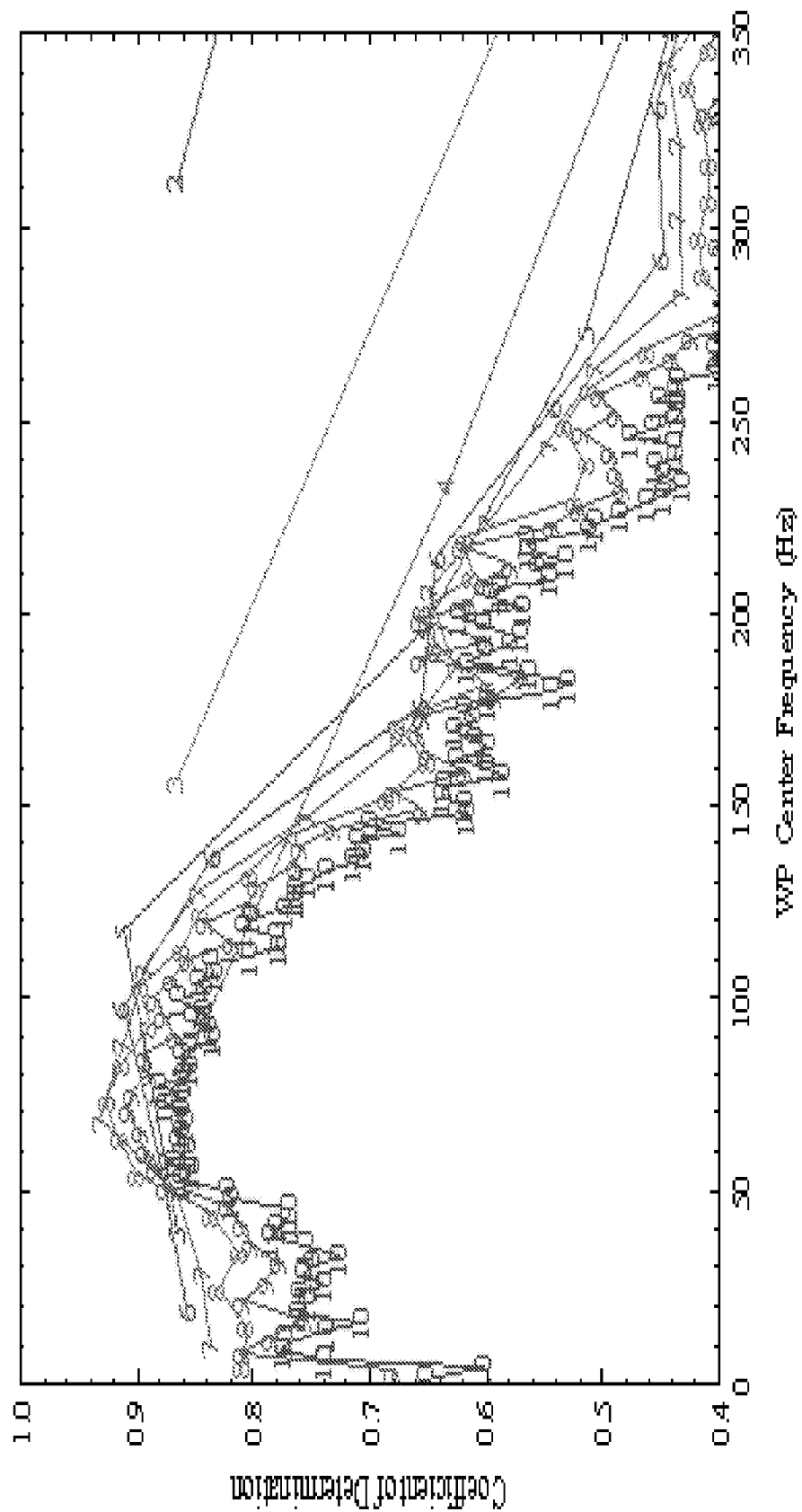
Figure 6G – Wavelet Order 7

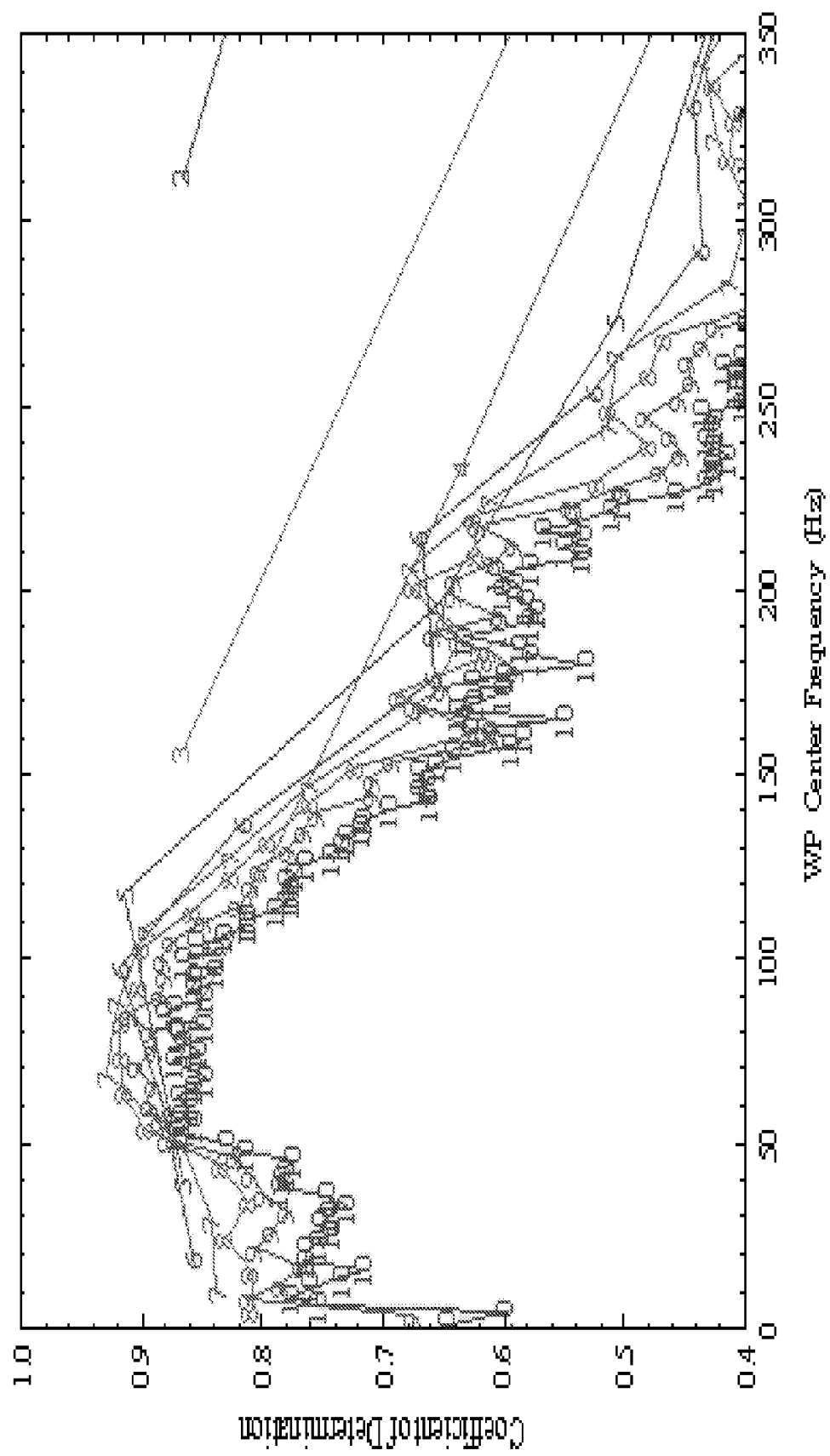
Figure 6H – Wavelet Order 8

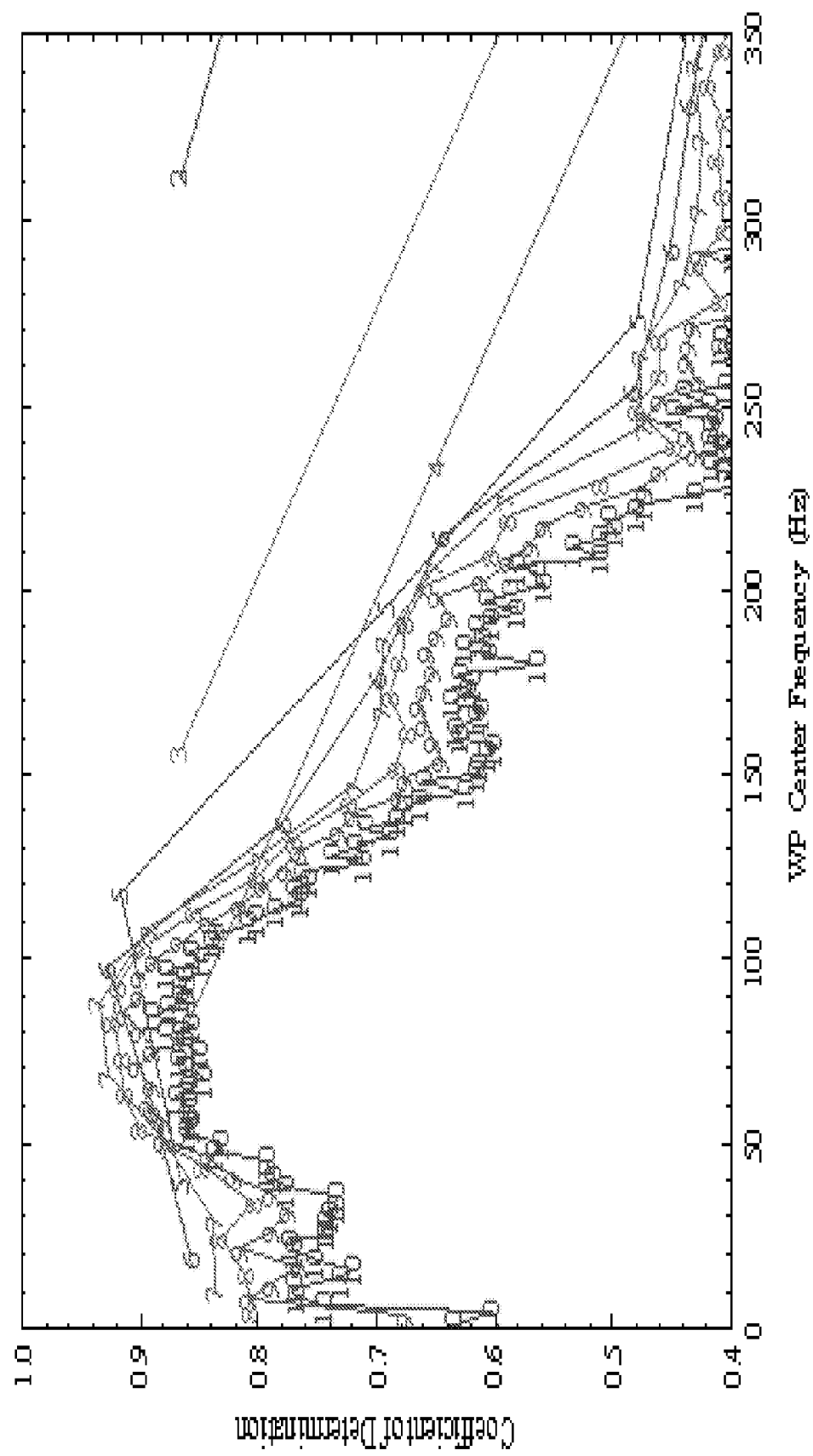
Figure 6I – Wavelet Order 9

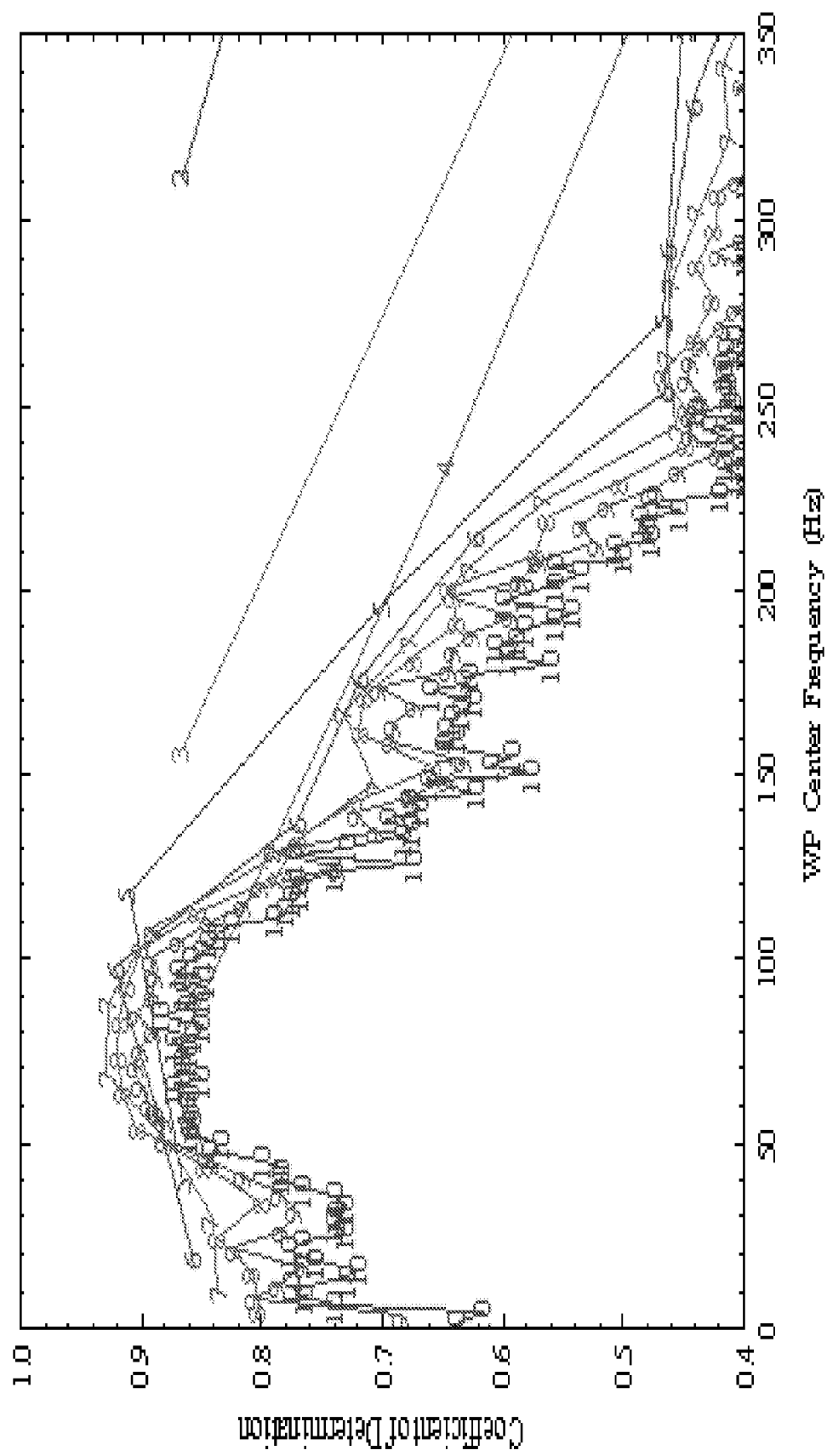
Figure 6J – Wavelet Order 10

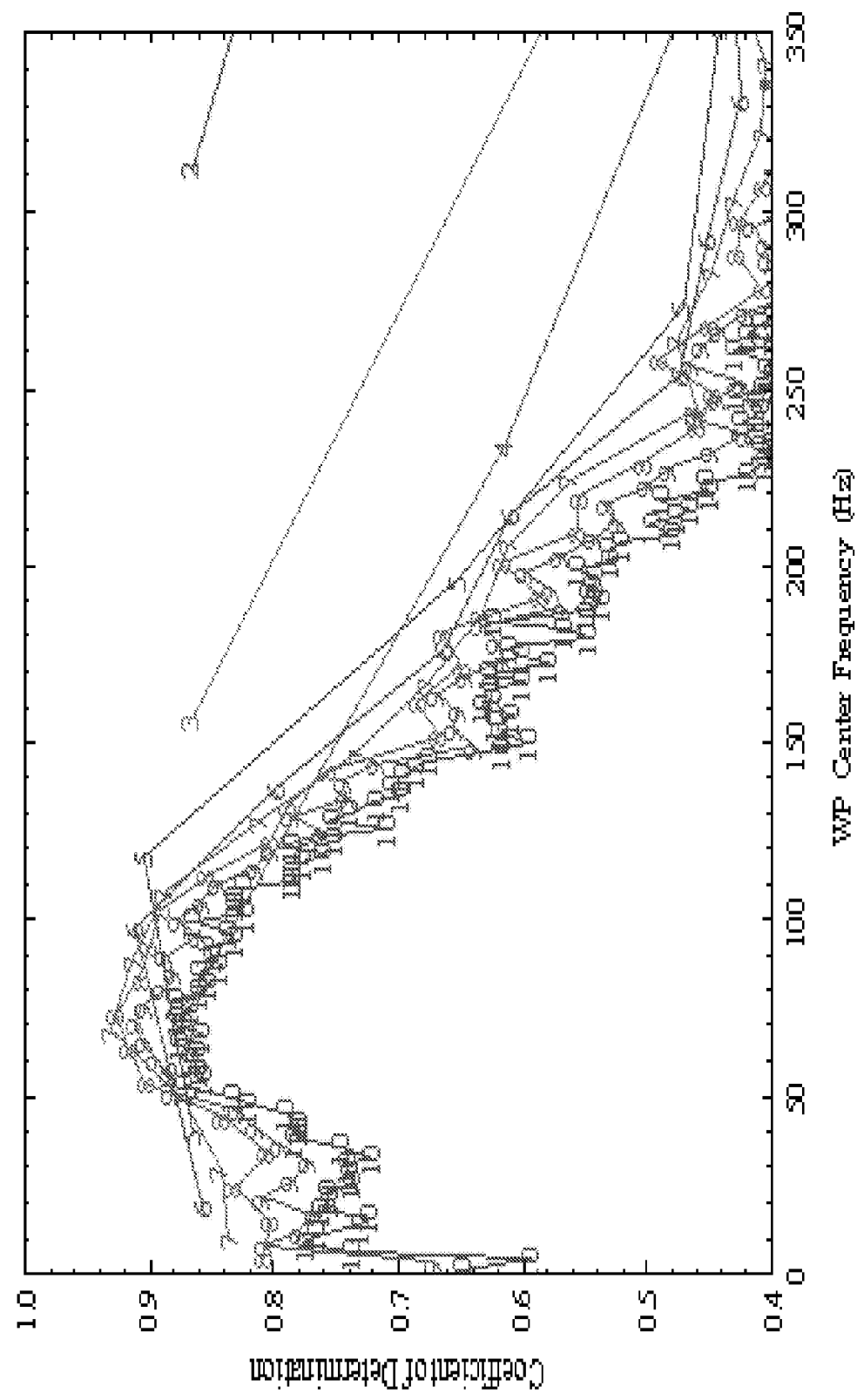
Figure 6K – Wavelet Order 11

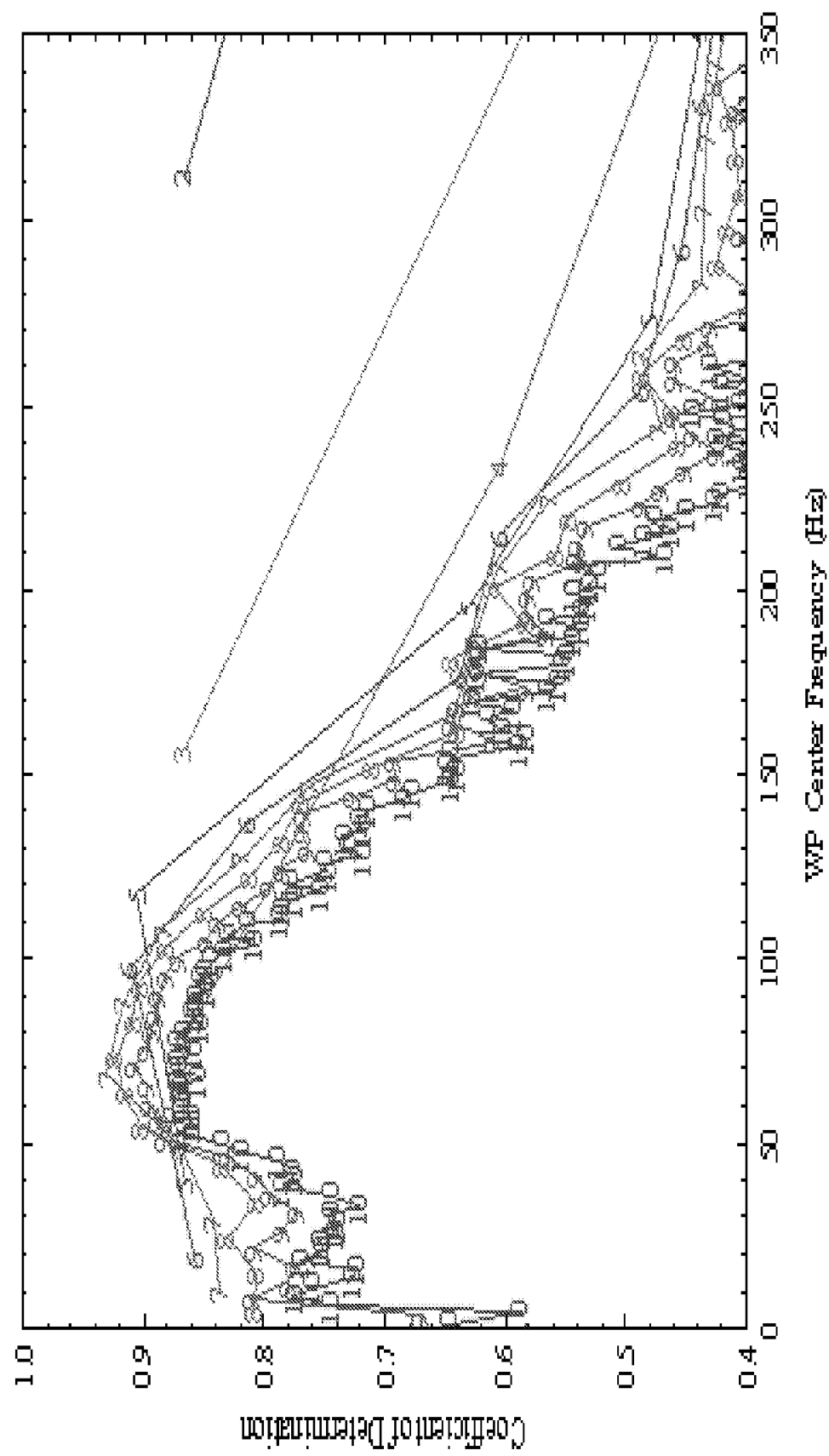
Figure 6L – Wavelet Order 12

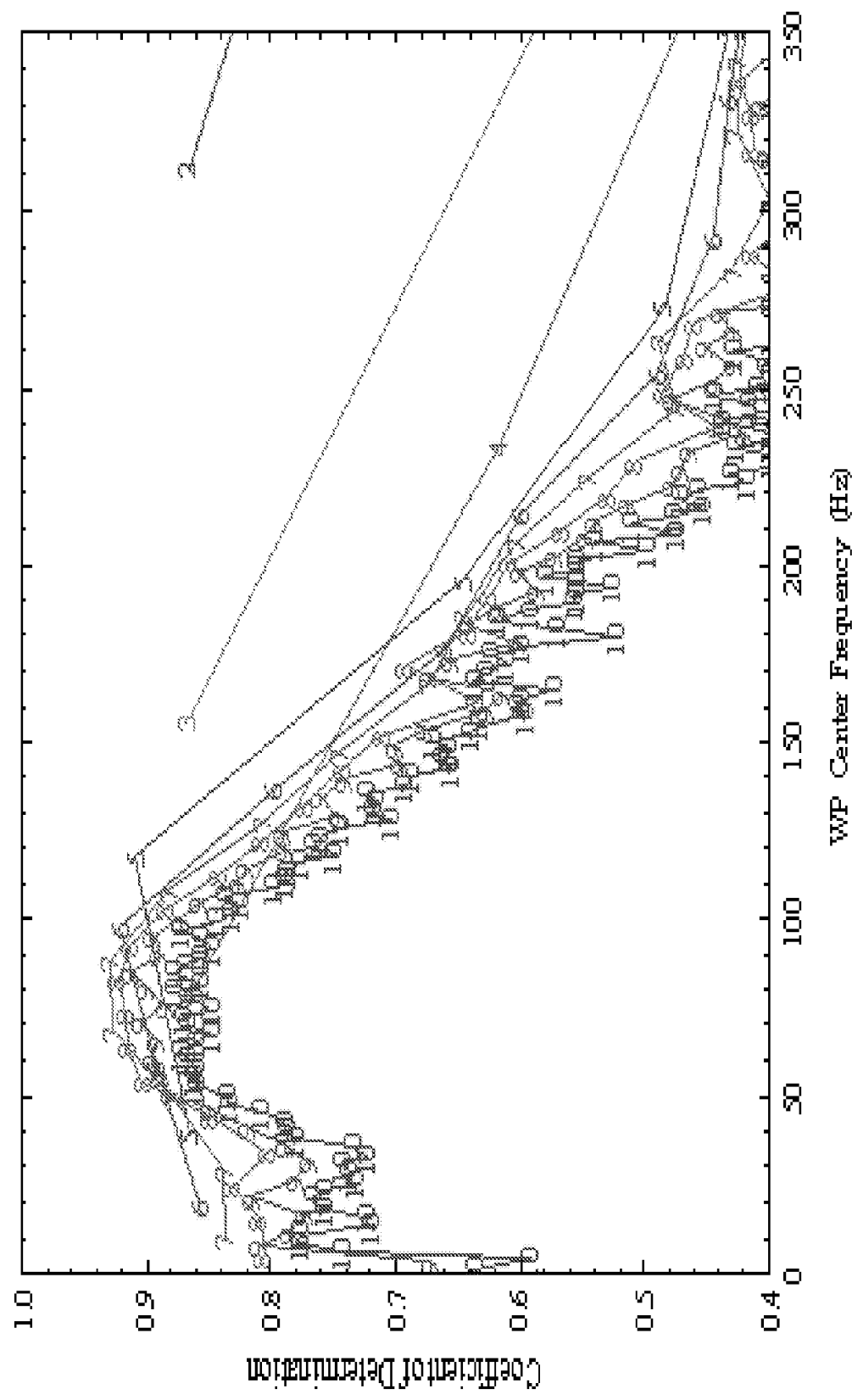
Figure 6M – Wavelet Order 13

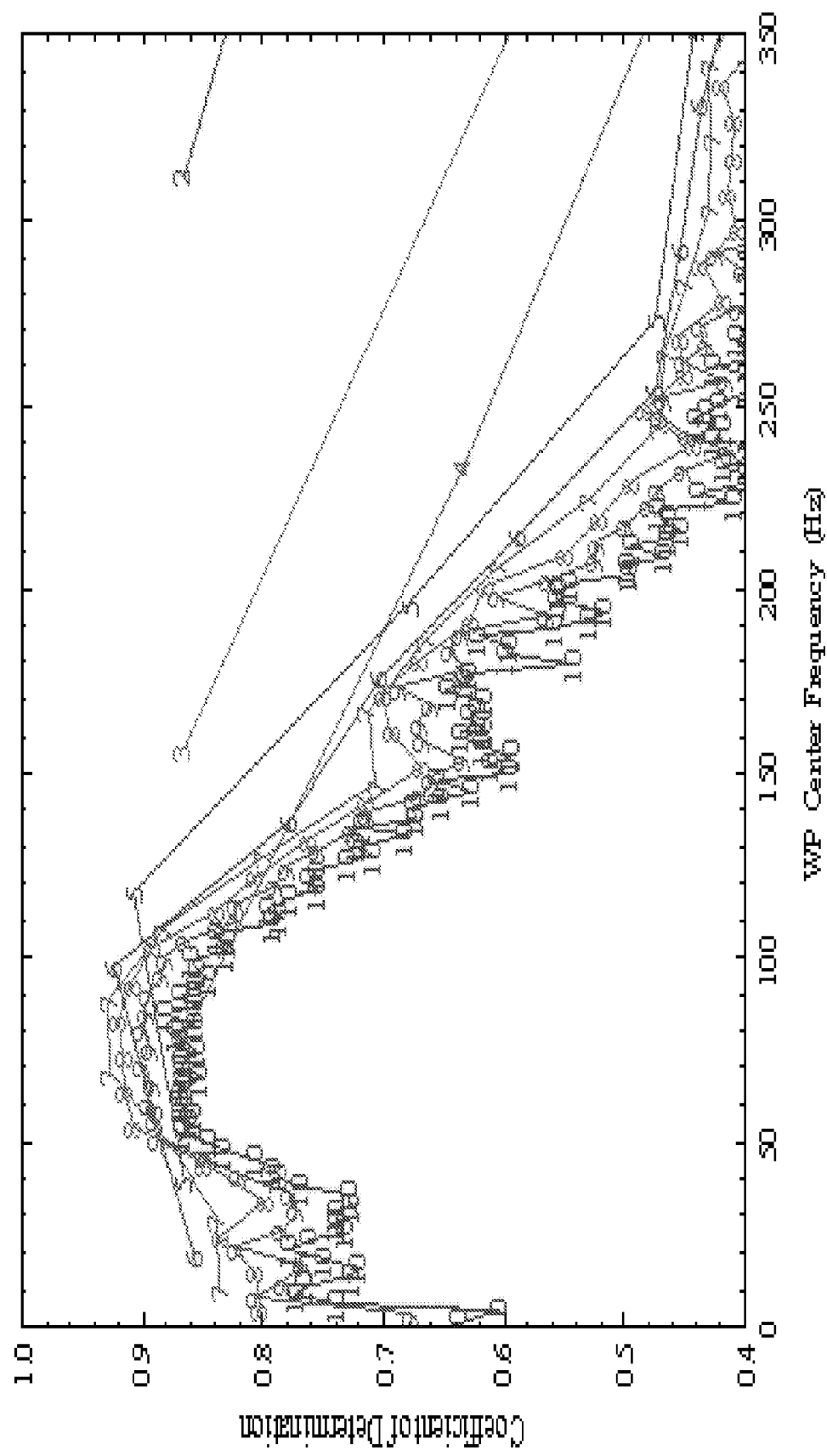
Figure 6N – Wavelet Order 14

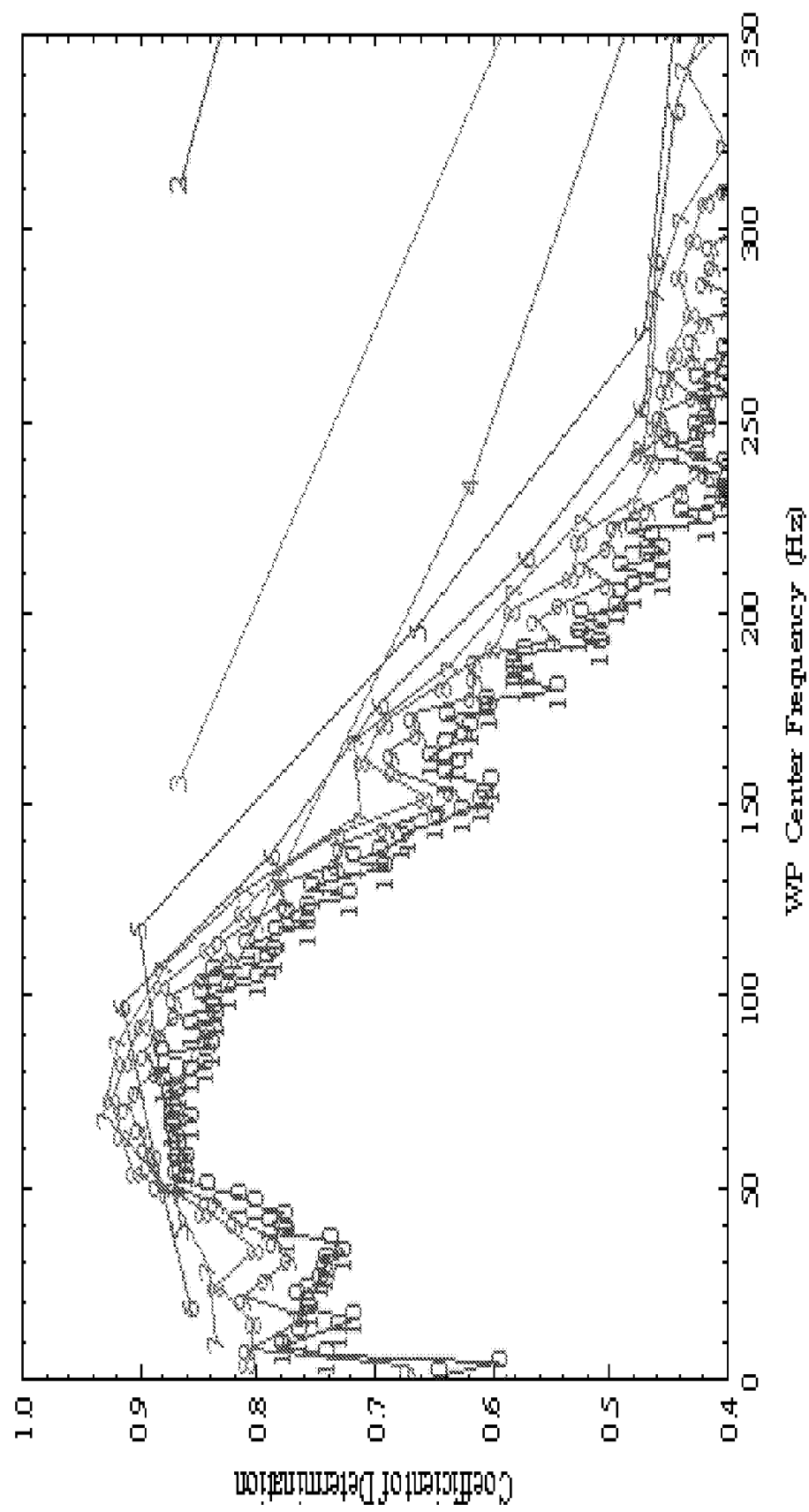
Figure 6O – Wavelet Order 15

SIGNAL ACQUISITION AND ANALYSIS

REAL-TIME ASSESSMENT OF ABSOLUTE MUSCLE EFFORT DURING OPEN AND CLOSED CHAIN ACTIVITIES

FIELD OF THE INVENTION

The present invention applies wavelet transforms to vibromyographic (VMG) data. In one embodiment, the present invention extracts estimates of muscle effort during contraction in real-time. In one embodiment, said contraction is selected from the group consisting of isometric contraction, isotonic contraction, isokinetic contraction, and functional contractions.

BACKGROUND

Individuals typically seek out, or are referred to, physical therapists (PT) for rehabilitation under one of three situations: 1) they are experiencing muscle or joint pain, 2) they have recently undergone surgery and need to regain a function lost due to the surgery, or 3) they have injured themselves at work or during recreation and need to restore function while limiting the risk of re-injury. Restoration of muscle function is by far the largest component of most rehabilitation protocols. This includes restoring range of motion, muscle strength and joint stability.

Individuals also seek out trainers in order to improve their performance, generally with the goal of enhancing performance without increasing the risk of injury or re-injury. Training focuses on three interrelated aspects of muscle function: strength, coordination, and bursting power or impulse.

In both scenarios, therapists and trainers prefer to use training activities that mimic the functional activities of the subject, and to evaluate function by accurately assessing the condition of the musculoskeletal system during such activities.

Range of motion is readily quantified through the use of inexpensive, easy to use, goniometer measurements.

Muscle strength measurements, by contrast, have posed more significant challenges. This, in large part, is because existing means for evaluating how strong a muscle is provide no direct measurements of the muscle's physiological activity. Instead, measurements of the displacement of a mass or resistance to an applied force are relied upon as surrogate indices of a muscle's functional status. Evaluation is typically made through specific performance measures (throwing, hitting, kicking, etc.), since no means exist for evaluating, in real-time in the field environment, the force-generating capabilities of a muscle. In these surrogate types of measurements, whether the muscle is lengthening or shortening, how fast the muscle is moving, the position of the limb or body part associated with the muscle(s) of interest, etc., are uncontrolled variables, any or all of which may influence the outcome of the measurement.

One means of measuring muscle strength is the dynamometer, either laboratory based or hand-held. Dynamometers measure the torque produced by a muscle, or group of muscles, at a skeletal joint, not muscle strength per se. Isokinetic dynamometers minimize shortening artifacts but are extremely expensive to purchase and maintain, and require trained personnel to operate. While hand-held dynamometers are less expensive and are easier to use, they are limited by the strength of the individual performing the measurement. In no case can a dynamometer measurement be made during typical functional activities (i.e. under conditions that physical therapists and trainers refer to as "closed chain" activities). Of most consequence, dynamometers can record the effect of only one muscle group at a time. They cannot separate out the contributions of each of the several muscles that cooperate to provide the complementary, supplementary, and/or antagonistic actions required to execute a particular motion. Physical therapists and trainers, however, need such differentiable information if they are to design safe and reliable exercises by ensuring that the strength of the involved muscles is well-balanced. As a result of these many limitations, dynamometers are used only very rarely in the PT clinic or among trainers. Consequently, PTs and trainers typically have no objective means for accurately and reproducibly evaluating muscle strength.

Joint stability, especially dynamic joint stability, cannot be measured objectively with available technology. The skills and experience of the examiner must be relied upon extensively. Attempts to quantify dynamic joint stability by measuring "joint laxity" (e.g., U.S. Pat. No. 4,649,934) confront the limitation that only passive stabilization can be employed in such measurements, which provides measurements for only a fraction of the components of dynamic stabilization.

Muscle coordination reflects the timing and strength of contraction of multiple muscles during a function. Again, evaluation is typically made through specific performance measures (throwing, hitting, kicking, etc.).

Bursting power is sometimes evaluated through dynamometer measurements, though it is more usually evaluated through a specific performance measure (e.g., height of a jump or exercise repetitions in a given time period).

The foregoing methods are inadequate for determining the effectiveness of a training program or for motivating an athlete/patient by providing objective feedback on a specifiable training goal. They are also less than acceptably reliable for evaluating whether an athlete/patient has safely reached a performance level equal to the risk of the competition/work that the individual intends. Finally, their effectiveness in medical diagnosis/prognosis is marginal.

More effective means of assessing muscle strength, coordination and joint stability are needed. Assessment should be founded on a reproducible, real-time, quantitative measure of effort expended by specific muscles of an individual during voluntary and stimulated contractions, whether concentric, eccentric and/or isometric, through the entire range of motion. The measurement should be realizable with portable, inexpensive testing apparatus, and should be of a form that permits a valid comparison of the effort of the various muscles involved in accomplishing a functional closed chain activity, either within one individual, or between individuals.

SUMMARY

The present invention employs wavelet analysis to transform vibromyographic (VMG) data acquired during a muscle contraction into wavelet packets. In one embodiment, the present invention extracts from one or more such wavelet packets a determinant of muscle effort during contraction in real-time. In one embodiment, said contraction is selected from the group consisting of isometric contraction, isotonic contraction, isokinetic contraction, and functional contractions. In some embodiments, the invention allows the artisan to simultaneously measure muscle efforts being generated by complementary, supplementary, and/or antagonistic muscle pairs such that real-time effort ratios can be calculated. In some embodiments, the measurements provide a means by which clinicians and trainers can diagnose musculo-skeletal injuries and pains associated with muscle imbalances.

VMG signals are waveforms comprising waves having frequencies up to about 150 Hz. A prime objective of the present invention is to recover from said signal, via wavelet packet analysis, a signal generated during (a) muscle contraction(s) of interest for use as a determinant of muscle effort. Recovery of this relatively slowly varying (0-5 Hz) signal is achieved by treating the wavelet packet as a relatively high frequency signal modulated by the 0-5 Hz signal. In preferred embodiments of the invention, demodulation methods are applied to extract the signal. Other groups that have applied wavelet transforms to VMG signals to isolate wavelet packets from VMG data teach that one should focus on (i.e., treat as a modulated signal of interest) only wavelet packets having center frequencies in the 30 Hz regime, where amplitudes tend to be highest. Applicants, by contrast, have shown that high amplitude components should not be used. Instead, they should be filtered out, as they simply confound the process for extracting effort information. As a result, preferred embodiments of the present invention treat only higher frequency wavelet packets as signals, the demodulation of which yields muscle effort information. Wavelet packets extending from about 50 Hz to about 150 Hz are preferred, and packets in the 70-100 Hz sub-band are more preferred.

Embodiments of the present invention, by providing, in real-time, information relevant to the generation of force during muscle contraction, allow the practitioner to 1) assess muscle activity during typical functional activities of the athlete/patient; 2) interrogate specific, individual muscles; 3) directly compare the effort produced by multiple muscles within a given athlete/patient (or between individuals) at a single point in time or over the course of time (days, weeks, months, for example). Embodiments of the present invention provide a convenient means of accurately assessing, in a time-resolved manner, the strength of muscles and muscle groups in the body in the context of the effort they contribute to coordinating movement of the body and its parts, and to maintaining joint stability. In preferred embodiments, vibromyographic data, transformed by wavelet packet analysis, are employed.

One embodiment of the invention provides a method of acquiring a determinant of an effort produced by a contraction of a muscle in a subject, the method comprising the steps of
   a. identifying a surface area of said subject, wherein said area overlies a muscle body of said muscle;
   b. positioning an accelerometer on at least a portion of said area in the proximity of said muscle body to create a positioned accelerometer, wherein said positioned accelerometer senses a vibromyographic input signal;
   c. applying to said positioned accelerometer an accelerometer-constraining means for pressing said accelerometer against said area to urge said accelerometer toward said muscle body in a manner that maintains said positioning during said acquiring.
   d. causing a contraction of said muscle body;
   e. receiving from said accelerometer a vibromyographic output signal;
   f. pre-processing said vibromyographic output signal in a wave filter to suppress a wave in said signal, said wave having a pre-determined frequency, to create a pre-processed vibromyographic signal;
   g. amplifying said vibromyographic output signal to create an amplified vibromyographic signal; and
   h. processing said pre-processed vibromyographic signal to create said determinant.

In a preferred embodiment, steps d-h occur during said contraction.

In one embodiment, said pre-processing suppresses a motion artifact in said vibromyographic signal. In one embodiment, said pre-processing suppresses essentially all waves in said signal having frequencies greater than 0 Hz and less than 40 Hz. In another embodiment, said amplifying amplifies said vibromyographic signal by more than about 10-fold and less than about 500-fold.

In one embodiment, said pre-processing comprises sampling said vibromyographic signal to create a digitized signal. In one embodiment, said digitized signal is created with a 16 bit analog-to-digital converter. In a preferred embodiment, said sampling is performed at a sampling rate greater than a Nyquist frequency. In one embodiment, said pre-processing creates a non-aliasing vibromyographic signal. In one embodiment, said digitized vibromyographic signal consists essentially of waves having frequencies > than $1/16^{th}$ of said sampling rate and < ½ of said sampling rate.

In another embodiment, said pre-processing suppresses a noise artifact in said digitized vibromyographic signal. In one embodiment, said de-noised signal consists essentially of waves having frequencies higher than about 30 Hz and less than about 300 Hz.

In still another embodiment, said pre-processing comprises down-sampling said digitized vibromyographic signal to create a down-sampled signal. In one embodiment, said down-sampled signal, in one second, comprises less than about 1000 samples and more than about 60 samples, and preferably more than about 500 samples.

In one embodiment, the invention provides a method of processing said pre-processed vibromyographic signal, the method comprising the steps of:
   a. decomposing said signal in a wavelet filterbank a pre-determined number of times to extract from said signal a wavelet packet, and
   b. demodulating said wavelet packet to extract an envelope of said wavelet packet.

In one embodiment, said demodulating comprises
   a. applying a Hilbert transform to said wavelet packet to create a 90° phase-shifted wavelet packet, such that each sample in said wavelet packet corresponds to a sample in said 90° phase-shifted wavelet packet, wherein said wavelet packet samples and said phase-shifted wavelet packet samples have real values;
   b. squaring said sample values to create square values;
   c. summing, for corresponding values, said square values to create a sum of squares, and calculating a square root of said sum to create a positive-valued wavelet packet, and
   d. low-pass filtering said positive-valued wavelet packet to create an envelope of said wavelet packet.

In one embodiment, said envelope is a determinant of said effort.

In another embodiment, said envelope is calibrated to create a muscle force expression.

In one embodiment, said muscle force expression is adjusted by subtracting therefrom a pre-determined threshold value, to create a supra-threshold value.

In one embodiment, said contraction occurs during a closed-chain activity. In one embodiment, said contraction occurs during an open chain activity. In another embodiment, the contraction occurs in response to an external stimulation. In yet another embodiment, the contraction occurs involuntarily.

In one embodiment, said muscle is selected from the group consisting of a voluntary muscle, a cardiac muscle, and an involuntary muscle.

In one embodiment, said muscle is a single muscle body.

In another embodiment, said muscle comprises a plurality of muscle bodies. In one embodiment, said determinant is one of a plurality of said determinants. In one embodiment, a ratio of said determinants is determined. In one embodiment, said ratio is determined for a muscle pair. In one embodiment, said ratio provides an index of balance between the members of said muscle pair. In one embodiment, said ratio provides a stability index of a joint. In some embodiments, said muscle pairs are selected from the group listed in Table 1.

In one embodiment, said determinants are created simultaneously. In another embodiment, said determinants are scaled by a calibration factor to create comparative determinants such that muscle effort can be compared between subjects.

In one embodiment, said accelerometer has a frequency sensitivity range of more than about 0 Hz and less than about 5 KHz. In another embodiment, said accelerometer has a working range from a noise floor of said accelerometer to about 100 m/sec$^2$. In another embodiment, said accelerometer has an electrical potential sensitivity of more than about 10 mV/(m/sec$^2$) and less than about 10,000 mV/(m/sec$^2$). In another embodiment, said accelerometer has a bandwidth of less than about 1000 Hz and more than about 10 Hz. In another embodiment, said accelerometer has a noise density of less than about 100 μg/Hz$^{1/2}$ and more than about 1.0 μg/Hz$^{1/2}$. In another embodiment, said accelerometer has a noise density of less than about 20 μg/Hz$^{1/2}$.

In another embodiment, the invention provides a method of selecting a wavelet filterbank and a decomposition level for use in a wavelet packet analysis of muscle effort, the method comprising:
  a. positioning an accelerometer in the proximity of a muscle body of a subject to create a positioned accelerometer, wherein said positioned accelerometer senses a vibromyographic input signal;
  b. causing a contraction of said muscle body against a plurality of different loads to create a plurality of different force generation measurements;
  c. receiving from said accelerometer during each said contraction a vibromyographic output signal;
  d. pre-processing said vibromyographic output signals;
  e. decomposing said pre-processed vibromyographic output signals at least one time in at least one filterbank to extract from said output signals a plurality of different wavelet packets;
  f. demodulating said wavelet packets to create a plurality of wavelet packet envelopes.
  g. for each said wavelet packet envelope, correlating a plurality of instantaneous force generation magnitudes and corresponding instantaneous wavelet packet envelope amplitudes;
  h. selecting for use in said analysis said wavelet filterbank and decomposition level that corresponds to said wavelet packet in said plurality of wavelet packets whose instantaneous envelope values correlate most closely with said instantaneous force generation measurements.

In another embodiment, the invention provides a method for converting a wavelet packet envelope representation of a client subject's muscle effort into units of force, the method comprising:
  a. providing a plurality of reference subjects;
  b. acquiring from said reference subjects a plurality of reference vibromyographic signals and reference force generation measurements of a muscle effort by a muscle in each of said reference subjects, wherein said muscle is made to contract against a plurality of loads to create a set of reference signals having corresponding force generation measurements;
  c. pre-processing and decomposing each said reference signal in a wavelet filterbank a selected number of times to extract from said signal a reference wavelet packet;
  d. demodulating said reference wavelet packet to create a reference wavelet packet envelope;
  e. determining a regression relation for a regression of a plurality of instantaneous reference force generation magnitudes and corresponding instantaneous wavelet packet envelope amplitudes against said corresponding force measurements to create a calibration factor, and
  f. applying said calibration factor to said client subject's wavelet packet envelope representation, such that said envelope is expressed in units of force.

In one embodiment, said load is a free weight. In another embodiment, said load is a torque. In one embodiment, said vibromyographic signals and force measurements are acquired from a plurality of muscles of said reference subjects to create a plurality of calibration factors for use in a database of said calibration factors.

In another embodiment, the invention provides an apparatus for acquiring and pre-processing a vibromyographic signal to condition said signal for extracting therefrom a determinant of a muscle effort, the apparatus comprising:
  a. an accelerometer having a working range of more than about 2 g and less than about 50 g, a bandwidth of 0-1 KHz, a sensitivity of more than about 0.01 V/g and less than about 10 V/g, and a noise density greater than zero and less than about 20 μg/Hz$^{1/2}$, wherein said accelerometer is in electrical, optical or wireless communication with a high-pass filter, said filter having a cutoff frequency of about 30 Hz;
  b. a pressing means for pressing said accelerometer against said muscle body;
  c. an amplifier in electrical, optical or wireless communication with said high-pass filter, wherein said amplifier (i) produces a high-pass filtered vibromyographic signal capable of spanning a full range of a 16 bit analog-to-digital converter, and (ii) is in electrical, optical or wireless communication with said converter.

In another embodiment, said apparatus further comprises:
  a. said analog-to-digital converter;
  b. an anti-aliasing filter in electrical, optical or wireless communication with said accelerometer and said converter, wherein said filter is constructed such that said converter digitizes said vibromyographic signal by sampling said signal at a rate greater than a Nyquist frequency.
  c. a de-noising filter from a signal frequencies higher than about 225 Hz, wherein said de-noising filter is in electrical, optical or wireless communication with said converter, and
  g. a down-sampling means for reducing the frequency of sampling, said downsampling means in electrical, optical or wireless communication with said converter.

In another embodiment, the invention provides a kit for assessing muscle effort, the kit comprising:
  a. a means of pressing an accelerometer against a muscle body such that said accelerometer receives a vibromyographic input signal from said muscle body;
  b. a vibromyographic sensor comprising:
    i. said accelerometer;
    ii. a means of sending a vibromyographic output signal from said accelerometer to an input port of a filter for removing motion artifacts from said output signal;
    iii. a high pass filter, and
    iv. an amplifier;

c. a software program for performing steps 240, 245, 250, and 255 as outlined in FIG. 22, wherein said program is embodied in a machine-readable medium, and d. instructions for the use of said pressing means, sensor and software.

BRIEF DESCRIPTION OF THE FIGURES

FIG. 1. Relationship between load force supported by the brachio-radialis and corresponding VMG recordings. 1A: Classical analysis utilizing RMS magnitude of the recording as a function of load force. A plateau in the VMG recording is observed at around 60% maximum voluntary contraction. 1B: VMG response following decomposition using wavelet packet analysis (WPA) techniques. Combinations of certain wavelet packets, specifically in this case, wavelet packets 9.7 & 9.9, are seen to provide the best correlations to absolute muscle effort (correlations >90%). Data represent average obtained for 24 individuals.

FIG. 6. Variation in muscle effort estimation using a variety of wavelet packets at mother wavelet orders 1-15 for data sampled at 5 KHz. Packets are identified by the center frequency of their power spectrum.

FIG. 13($a$): An elastic strap is wrapped around the thigh to provide compressive pressure on the recording accelerometers. The accelerometers are located between the skin and the strap. Three accelerometers are utilized, one recording from each of the VL, VM, and BF. FIG. 13($b$): Accelerometer signals are filtered, amplified, and digitally sampled, then serially communicated to a digital computer where analysis of the data is completed and results displayed.

FIG. 16($a$): Males. FIG. 16($b$): Females.

FIG. 19($a$): Males. FIG. 19($b$): Females.

DEFINITIONS

Figure 2:
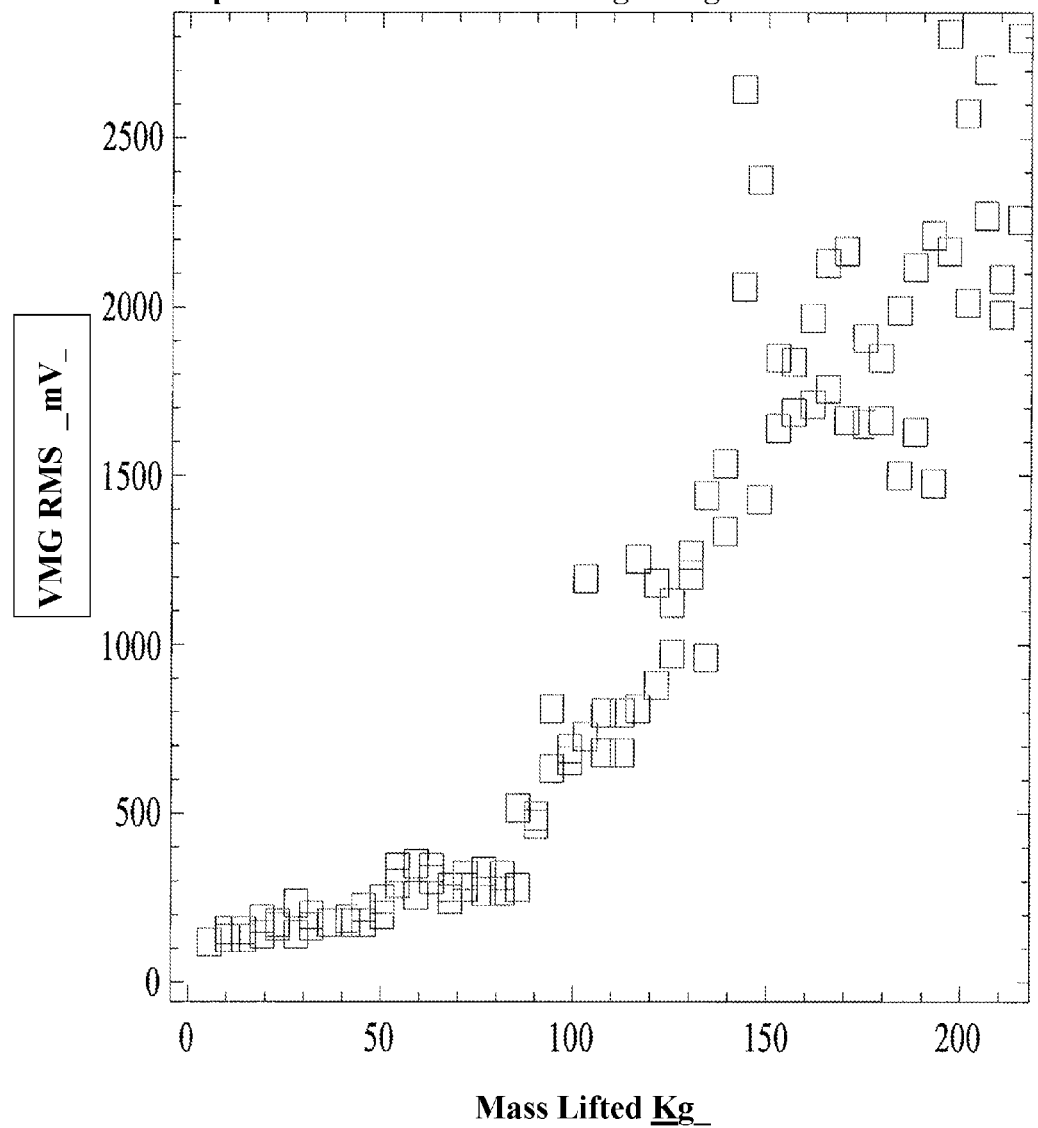
FIG. 2. Variation in VMG:Load-force data when utilizing static analysis technique with short (1 second) data segments. Large variations in predicted muscle force are evident above approximately 60% maximum voluntary contraction.

To facilitate an understanding of the descriptions herein of embodiments of the invention, a number of terms are defined below. Terms defined herein (unless otherwise specified) have meanings as commonly understood by persons of ordinary skill in the areas relevant to the present invention. As used in the Specification herein and its appended claims, terms such as "a" "an" and "the" are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

The phrase "chosen from A, B, and C" as used herein, means selecting one or more of A, B, C.

As used herein, absent an express indication to the contrary, the term "or" when used in the expression "A or B," where A and B may refer to compositions, objects, diseases, products, etc., means one or the other ("exclusive OR"), or both ("inclusive OR"). As used herein, the term "comprising" when placed before the recitation of steps in a method means that the method may encompass one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities in the specification and claims are to be understood as being modified in all instances by the term "about." Accordingly, unless indicated to the contrary, the numerical parameters in the specification and claims are approximations that may vary depending upon the desired properties sought to be obtained in a particular embodiment of the present invention. At the very least, and without limiting the application of the doctrine of equivalents to the scope of the claims, each numerical parameter should be construed in light of the number of reported significant digits and by applying ordinary rounding techniques. Any numerical value, however, inherently contains deviations that necessarily result from the errors found in the numerical value's testing measurements. Thus, "about," unless otherwise specified, typically means plus or minus 10%.

The term "not" when preceding any particularly named entity or phenomenon, and made in reference thereto, means that only the particularly named entity or phenomenon is excluded.

The term "altering" and grammatical equivalents as used herein in reference to any entity and/or phenomenon refers to an increase and/or decrease in the quantity of the entity in a given space and/or the intensity, force, energy or power of the phenomenon, regardless of whether determined objectively, and/or subjectively.

The terms "increase," "elevate," "raise," "amplify" and grammatical equivalents when used in reference to the quantity of an entity and/or the intensity, amplitude, frequency, incidence, force, energy or power of a phenomenon (including, in the case of a disease, a symptom) in a first sample or subject, relative to a second sample or subject, mean that the quantity of the entity and/or the intensity, amplitude, frequency, incidence, force, energy or power of the phenomenon in the first sample or subject is higher than in the second sample or subject by any amount, ratio or rank in a rank order that is statistically significant using any art-accepted statistical method of analysis. The terms may be used similarly in respect of a phenomenon observed at different time-points. In one embodiment, the increase may be determined subjectively, for example when a patient refers to his subjective perception of disease symptoms, such as pain, clarity of vision, etc.

The terms "reduce," "inhibit," "diminish," "suppress," "decrease," and grammatical equivalents when used in reference to the quantity of an entity and/or the intensity, amplitude, frequency, incidence, force, energy or power of a phenomenon (including, in the case of a disease, a symptom) in a first sample or subject relative to a second sample or subject, mean that the quantity of the entity and/or the intensity, amplitude, frequency, incidence, force, energy or power of the phenomenon in the first sample or subject is lower than in the second sample or subject by any amount or ratio or rank in a rank-order that is statistically significant using any art-accepted statistical method of analysis. The terms may be used similarly in respect of a phenomenon observed at different time-points. In one embodiment, the reduction may be determined subjectively, for example when a patient refers to their subjective perception of disease symptoms, such as pain, weakness, etc.

A "subject" herein refers to any person or animal to which embodiments of the invention may be applied. Said subject may be referred to as a "patient," a "client subject," or simply an "individual" without implying different meanings. Embodiments of the invention may be applied to subjects to acquire data for statistical purposes, in which case such subjects may be referred to as "test subjects" or "reference subjects."

The term "determinant," as used herein, refers to any measure, indicium, sign, signal, etc. employed to determine a quantity, condition, state, effect or outcome. For example, the peak force generated by a muscle is a determinant of the strength condition of the muscle. A "pre-determined" measure refers to a quantity, condition or state of an embodiment of an invention as determined by the practitioner of the invention.

"Sensitivity," as used herein, refers to the power of a method of identification to make correct identifications. "Specificity," as used herein, refers to the power of a method of identification to exclude incorrect identifications. "Accuracy," as used herein, refers the power of a method of measurement to make a measurement equal to the true value of a quantity. "Precision," as used herein, refers to the power of a method of measurement to make the same measurement repeatedly.

A "database" herein refers to any set of data that is recorded and organized according to a logical relation such that said data may be retrieved, combined, transformed or otherwise manipulated for one or more purposes. The term includes, in particular, a database comprising wavelet packet data, and corresponding calibration factors derived from dynamometer measurements or measurements involving the lifting or moving of free weights. The data are segregated into a plurality of categories of muscle effort, including but not limited to muscle effort profiles in a variety of dynamically contracting muscles of both women and men, young and old. In preferred embodiments, the database is used to select the calibration factor that is appropriate for transforming a particular vibromyographic test result into the muscle force data that a dynamometer would, in principle, provide. In a most preferred embodiment, the database is integrated such that the vibromyographic measurements may be made, analyzed and expressed in real time.

Terms Related to Signal Analysis:

A "wave" herein refers to a disturbance in a state of matter or energy, which disturbance moves through space and/or time. In its simplest conception, the state of the matter or energy is in equilibrium (e.g., an electric field in which electrical energy is evenly distributed), but for the disturbance, and the disturbance moves sinusoidally, with amplitude u, through space (x) and over time (t) according to the equation $$u(x,t)=A\cos(kx-\omega t+\phi),$$

wherein A is the "semi-amplitude" and $\phi$ ("phase offset") takes into consideration changes in phase that occur as the disturbance moves through time.

Sinusoidal movement is cyclical. In each cycle, the disturbance moves from a peak "down" to what would be equilibrium, traversing a "distance" A (the semi-amplitude) equal to one half of the wave's overall amplitude, and then below equilibrium to a nadir (or "negative peak") and back up to the peak. The full cycle covers a "peak-to-peak" distance (wavelength $\lambda$), which it traverses in a period, T. The number k, of successive cycles that can traverse a unit of distance (such as a meter) depends upon the cycle's wavelength:

$$k=2\pi/\lambda$$

A wave can thus be characterized by k, its wavenumber.

A trace or "wave-train" of a wave viewed over several cycles creates, at its peaks, an "envelope." It is to be noted that the amplitude of a single cycle and the amplitude of the envelope, as the terms are used herein, may be different because of "pulses" or "packets" of energy that pass along the wave train, affecting the amplitudes of individual cycles within it. The terms "peak envelope" and "peak amplitude envelope" both refer herein to the envelope described or outlined by the successive peaks of a wave-train, whereas the term "envelope peak" is synonymous with "envelope amplitude" herein, and generally refers to an amplitude in the envelope of a wave packet. An envelope amplitude generally refers herein to an "instantaneous" amplitude, that is, the amplitude of the envelope at a specific point in time. Thus, a "peaky" packet envelope may have several amplitudes.

The number of periods that transpire in a unit of time is the frequency f, of the wave:

$$f=1/T.$$

If the unit of time is one second, frequency is denominated in "hertz." "Waves," inasmuch as every wave is uniquely identified by its particular "f," are often referred to simply as "frequencies." In some contexts, however, a given wave may be said to occur relatively "frequently," which leads to incongruous statements such as "The 220 Hz wave has a higher frequency than the 440 Hz wave." To avoid such confusion herein, the term "wave frequency" is generally a reference to the rate of oscillation of the wave, not to the number of times a wave having a particular rate of oscillation can be counted in a particular circumstance.

The wave frequency of a sinusoidal wave can be determined without relying on a measure of distance (or linear displacement) if each cycle is represented as a unit circle. A line between the circle's center and any given point on its circumference describes a radius. As the point moves on the circle's circumference, the radius subtends an angle, the magnitude of which relates to the rate at which the point moves in a unit of time:

$$\omega=2\pi/T$$

The position of the aforementioned point at any time, measured as an angle (the "phase angle"), defines the phase of a cycle. If the point moves at a constant speed v (the "phase speed") the relation $$v=\lambda f$$

holds.

Graphical expressions of sine (and cosine) waves, although commonly plotted "from left to right," are intended to represent a rotation in either direction. That is, when one observes a sine wave of a given frequency, one is actually observing two sine waves at once, one of which has a positive frequency (a first direction of rotation), the other of which has a "negative frequency" (an opposite direction of rotation).

The term "band" (or "waveband") when used herein in connection with waves, refers to a set of waves having wave frequencies that range over a "frequency domain," wherein the extent of the range is referred to as the "bandwidth." Subsets of the waves in a band are referred to herein as "sub-bands."

Sinusoidal waves can be variously "modulated." By way of a non-limiting example, information may be transmitted via radio by sending from an antenna a fundamental, high-frequency cosine wave (a so-called "carrier" wave) coupled to one or more waves of lower wave frequency in such a manner that the energy in the latter (e.g., acoustic energy generated by human vocal chords) combines with the energy of the carrier wave, changing the amplitude in several successive cycles of the carrier wave. The low frequency waves are, in a sense, "absorbed" by the carrier wave. The information (or "message") in them, however, is not lost but is carried along in the carrier signal. The outline within which the affected waves "fit" (the "envelope") approximates the information of interest that, before coupling, was in the waveform having the lower wave frequency. The modified carrier wave is an "amplitude modulated" signal. The combining process is modeled mathematically as a "convolution" operation. Radios "demodulate" the signal, recovering a facsimile of the vibrating vocal chords, the energy from which drives the radio's speakers.

Many demodulation schemes are known. All of them have the objective of "canceling out" the elements in the carrier wave itself without canceling elements of the aforementioned envelope. If the values for the parameters of the original carrier signal are known or can be determined, a suitable convolution of the original signal and the modulated signal will extract the message signal directly. So-called "coherent detection" is an example. Where these values are not known, as is the case herein, other cancellation schemes may be used.

It is to be noted that simple low-pass filtering is not effective in separating the low frequency message from the high frequency components of the wavelet packet, because the wavelet packet signal contains (real) positive and (real) negative values. It is also to be noted that the wavelet packet signal to be demodulated in preferred embodiments herein is a sampled signal. As such, the datapoints captured from the signal provide instantaneous amplitudes but do not generally fall at peak amplitudes. It follows that a straightforward time-plot of the sampled datapoints does not describe the envelope of the carrier wave.

A preferred method of overcoming these faults comprises applying a "Hilbert transform" to the digital data. Essentially, the Hilbert transform shifts the phase of the sampled signal by 90°. The sampled signal, combined with its Hilbert transform by squaring, at each time-point, the value of the wavelet packet signal as sampled and also squaring the value of its Hilbert transform at that time-point, and taking the square root of the sum of those squares, produces a set of (real) positive-valued datapoints adjusted to peak-point amplitude. At this stage, a low-pass filter can be used to suppress high frequencies, revealing a "clean" representation of the message. In this case, the message represents the generation of effort by a muscle.

The Hilbert transform is well-known to persons skilled in the art of signal analysis. U.S. Pat. No. 3,908,114, incorporated herein in its entirety for all purposes, and made a part hereof, provides a mathematical definition of the Hilbert transform, and describes a system for implementing the transform in the context of signal processing.

A "signal," as the term is used herein, is a waveform that has information embedded in it in the form of time-related variations in frequency, amplitude, wavelength and/or phase introduced by natural or man-made processes. A "sensor" of the signal picks up the waveform as "input" and transduces the energy therein by converting the signal to another form of energy (typically an electric current or voltage) to create an "output" signal. By way of a non-limiting but pertinent example, muscle bodies produce vibrational waves. The frequencies of those vibrations extend from 0 to about 150 Hz.

Although the applicants do not intend to be bound by any theory of how any embodiment of the present invention works, it is convenient to envision the higher frequency vibrations as serving a function reminiscent of the radio carrier waves discussed above. That is, the lower frequency vibrations in the VMG signal are treated, collectively, as the message. The energy of the message combines with the energy of the higher frequency vibrations, modulating the higher frequency waves. Although "faint," a sufficiently sensitive accelerometer placed on skin that overlies the contracting muscle can "sense" the modulated high-frequency vibrations as inputs. The accelerometer converts these into an electrical signal.

"Digital signal processing," as used herein, refers to the analysis or conditioning of discrete samples of data taken from a continuous (i.e., "analog") signal. Information embedded in the signal "between" samples is not processed. Because of this, it is possible that the analyzed signal will reflect not the original signal, but an "alias" of the original signal. To prevent this, it is highly preferable to sample the signal at a rate at least twice as high as the highest frequency that exists in the original signal (i.e., at or above the "Nyquist sampling frequency"). Sampling at frequencies higher than the Nyquist frequency improves resolution with a tradeoff in demands on memory and computational costs.

A waveform, particularly if it has an irregular graph, may appear complex but, if it is "stationary," it has constant statistical properties over time (or space). The set of waves that is the synthesis of a waveform typically comprises waves having different wave frequencies. Each waveform has a characteristic "pattern of frequencies," represented by the waveform's "frequency spectrum" or, simply, "spectrum." The amplitude of waves at each given wave frequency is reflected in the spectrum. The spectrum of some waveforms (a VMG signal from a contracting muscle, for example) can vary with time, in which case the waveform is "non-stationary." Variations in a spectrum over a period of time are explained by shifts that occur in the phase of some (at least one) of the waves with respect to others during the period, leading to reinforcements and cancellations of waves. The result is a rearranged pattern of frequencies, i.e., a "spectral shift." A signal that shifts in this way is non-stationary.

The frequency and amplitude of a wave together determine the energy, whether electrical, electromagnetic, mechanical or otherwise, that a wave propagates. Every waveform comprises waves of (usually) various amplitudes having different wave frequencies distributed over a spectrum, creating, in the aggregate, a "power spectrum."

Any waveform can be described (at least mathematically) as a sum of the amplitudes, as a function of time (or space), of a set of regular sine and cosine waves. Whether or not such waves (or any of them) have a basis in physical reality, any actual (i.e., measured or measurable) waveform, including signals of a wave nature, can be "resolved" or "decomposed" into such a set. For stationary signals, Fourier analysis achieves this result.

"Noise" as used herein refers to the time-dependent output of a sensor in the absence of any deliberate input. That is, whatever the difference ought to be between the input signal and the output signal, the noise component is not information. It is, instead, "artifact." Fortunately, since noise simply comprises unwanted waves, most signals can be "de-noised" by removing (suppressing) the waves attributable to the noise by means of a filter (or "wave filter"—see below)

"Noise density" as used herein refers to the spectral power of the output of a sensor in the absence of any deliberate input relative to that of an actual output signal. It is often represented as the noise power in a given frequency band divided by the width of that frequency band (i.e. typical units would be $V^2/Hz$)

"Transform" as used herein refers to a mathematical algorithm or rule which, when applied to data represented in one way (e.g., in a first domain), translates it for representation in a second domain. Exactly the same data, for example, may be represented in the time domain or in the frequency domain. Similarly, a set of data may be displayed on rectangular (Cartesian) coordinates or on polar coordinates by means of well-known equations. A transform generally includes a means of recovering the original representation.

As noted above, a waveform can be analyzed as if it were a composite of more mathematically tractable waves, for example, by Fourier analysis. Fourier analysis of digital data is accomplished utilizing the Fast Fourier Transform ("FFT"), also referred to as the Discrete Fourier Transform ("DFT"). A stream of samples (a "file" of datapoints) from the waveform is analyzed by applying to the file a so-called "decimation algorithm." The algorithm calls for reiterative computation. Each iteration, however, operates (typically) on one-half the file length of the prior iteration. To achieve this "decimation," one can either interrogate shorter and shorter time segments or sample the waveform over an extended period, but less and less frequently (but not less than the Nyquist frequency). The data in the datafile must exhibit no long-term "trend" or drift and, when applied to FFTs, the statistical variance of the data must not itself vary over time. FFT algorithms are commonly available in most statistical data analysis software packages (e.g., MatLab, Mathematica, Origin). To achieve the decomposition/decimation steps, however, Fourier methods require the use of data distributed over an extended period (from + to − infinity, in principle), so the methods only reveal which sinusoids (sine waves and cosine waves) comprise the waveform, not when in the history of the waveform a particular wave of a certain frequency is present. Indeed, a waveform comprising component waves that "come and go" while the waveform is being recorded does not yield to Fourier analysis. Instead, the time variations lead to incorrect values for the resolved waves. If one analyzes time-varying data over a very short time-period (or "window") and compares the period-to-period results, some possibly meaningful frequency variations over time can be discerned. However, the window simultaneously provides a view of a time period (where a narrow window is preferred) and of a frequency range (where a wide window is preferred, especially to capture lower frequencies.

The essence of "wavelet analysis" (see below) is that it allows the analyst to take scale into account by varying the width of the window and the extent of its time-shift (or space-shift) during analysis. Thus, the analysis, in effect, inspects the signal at relatively high resolution with respect to both frequency and time. The objective of wavelet analysis is to resolve a waveform into a set of components (sub-bands) that differ with respect to the range of wave frequencies in each sub-band, and also with respect to scale (i.e., the bandwidth of each sub-band).

The "frequency response" (also called the "amplitude response") of a device to an input signal is a measure of how much the device (1) changes the amplitude of the signal (i.e., attenuates or amplifies the oscillations comprising the signal at each of a "spectrum" of frequencies) and (2) shifts the phase of the entering waves. Any means that amplifies, attenuates, changes the phase of, or prevents the passage of a wave is a "filter" or ("wave filter") as that term is used herein. These operations on a waveform are "filter" operations whether applied to a stream of electrons passing through capacitors, resistors and inductors in a real electronic circuit or to an equation of the waveform undergoing transformation in a programmed computer, or to discrete data representing a waveform. In general, (time-invariant) filters work solely by changing the gain and/or shifting the phase of the waves that comprise input signals. The formula that relates the output of a filter from a given input to that filter is referred to as the filter's "transfer function." It is the ratio of the equation that describes the input signal as a function of frequency and the equation that describes the output signal as a function of frequency. Both, commonly, are differential equations. For computational convenience, this ratio of equations is mathematically transformed into an algebraic expression (i.e., an expression having no differential terms) that is simply the ratio of two polynomials (albeit comprising complex numbers). Over frequency ranges where the ratio tends not to spike (as it does when the denominator approaches zero) or dip (as it does when the numerator approaches zero), the transfer function is said to be "flat" or in an "extremal phase" (analogous to the "extrema" of a function, i.e., where the derivative of the function and therefore its slope is zero).

A "finite impulse response" filter ("FIR") as the term is used herein is distinguished from an "infinite impulse response" filter ("IIR"). The response (i.e., the output) of the latter to an "impulse" ("on" then immediately "off") may continue indefinitely. The response of the former is relatively short-lived ("finite").

"Analog filters" operate on signals that are essentially continuous (setting aside exceptions such as quantum scale discontinuities). "Digital filters" operate on discrete "samples" of sequential (i.e., continuous or "analog") data to impart gain and to shift phase. For example, a filter might store (see below) two or more successive input samples and add them to create an output. Some filters also employ an output sample to change the value of an input sample. These are "recursive" filters. The "order" of a filter relates to the number of samples the filter's transfer function must use to calculate an output as dictated by the polynomial expressions in its transfer function. For example, if three input samples and two output samples are required in a recursive filter, the filter is of order three. If two input samples and three output samples are required, the filter is also of order three. Equivalently, the order of the filter equals the order of the highest order polynomial in the transfer function. Digital systems (such as an analog-to-digital converter) may be rated on a "bit-scale." A "bit" conveys complete information about a binary state. A switch is binary inasmuch as it is either "on" or "off." A system of 16 such switches can exist at any given time in one of $2^{16}$ states. That is, it can have any of 65,536 values.

A delay in the transfer of an analog signal through the filter (i.e., a "storage" event) can be implemented in electrical "hardware" by using electrical induction. Inductor delay is adjustable using physical "taps" on an inductor. For historical reasons, the degree of storage in digital filters is sometimes quantified in terms of a number of "taps," although inductors are no longer implemented electromechanically. The more calculations the filter requires, the more storage events, and thus "taps," it will have. A filter design with many taps is more precise but also is more computationally expensive.

The transfer function of "high pass" filters is designed to allow only high frequency elements (i.e., rapidly oscillating waves) of the input signal to participate in the output (above a certain "cut-off" frequency). "Low pass" filters allow only low frequency elements to participate (up to a certain cutoff frequency). The cutoff settings of so-called "band-pass" filters permit only mid-frequency elements to participate. Because oscillations that are not part of the signal (i.e., "noise") confound the analysis of the signal, particularly if they are high-frequency oscillations, low-pass filters tend to create "reduced-noise" signals. Real filters do not cut off signals abruptly. Thus, a plot of amplitude as a function of frequency for a high pass filter will have, over some range of frequencies, a slope between infinity and zero (the so-called "roll-off").

The term "pre-processing," as used herein, refers to any conditioning of a signal (in particular, herein, a vibromyographic signal) that may be necessary to reduce or eliminate data embedded therein that might lead to misleading results or unnecessarily increase the analytic cost of the analysis. For example, embodiments of the present invention involve macroscopic motions that are irrelevant to the microscopic vibrational movements that a vibromyograph represents. Although such macroscopic data are referred to as "motion artifacts" in the vibromyograph, it will be understood that the motions themselves figure importantly in the activities analyzed in embodiments of the invention. As noted above, signals comprise waves that may differ from one another in frequency, amplitude, wavelength or phase. Thus, "pre-processing" encompasses any change induced in any such element including but not limited to removing a wave from the signal by electrical, electronic or other means, or by augmenting the signal by adding a wave thereto. It will be understood that "removing" a wave is not intended to imply complete removal, and "removal" is intended to encompass "suppression." That is, whether or not a wave or element thereof remains "in" the signal in some sense, suppression of its effect is herein equivalent to its removal.

"Time-frequency analysis," as used herein, relates to any analysis of a signal that characterizes the signal by resolving specific waves within the signal and the "locations in time" at which these waves arise and persist over a defined period. It is not intended that the present invention be limited to any specific method of time-frequency analysis. Any method that processes a vibromyographic signal acquired from a muscle during a contraction of that muscle, such that an effort-generation profile for that contraction can be derived from the processed signal, is within the scope of the invention.

"Wavelet analysis" is one method of time-frequency analysis. A "wavelet" is a designed waveform much shorter in length than the waveform of the signal being analyzed. Mathematically, it is a rapidly decaying wave function that oscillates above and below zero in such a way that its integral equals zero. When "convolved" (a method of vector multiplication that results in an "inner product") with a portion of the signal being analyzed, that portion (i.e., a subset—or "sub-band"—of all the waves that comprise the signal) is found to correspond (to some extent) to the spectrum of waves that comprises the wavelet. The amplitude of the convolution (expressed as a "wavelet coefficient" or "convolution coefficient") is a measure of the similarity between the wavelet's spectrum and the portion (the sub-band) of the signal that was convolved with it. In wavelet analysis, the wavelet, in effect, is "moved" or "translated" or "shifted" along the signal in a series of time-steps, and the convolution operation is reiterated at each step. The shifting exercise is typically repeated with a wavelet identical to the first but for its scale (i.e., the extent to which it is stretched or "dilated"). The wavelet to be shifted or rescaled is often referred to as a "mother wavelet" and its shifted or rescaled "offspring" are called "daughter," "child" or "baby" wavelets. For a signal that can be represented in two dimensions (as is the case herein), the shifting-scaling-convolution process amounts to an interrogation of various sub-bands of the signal. The objective of each interrogation is to determine the sub-band's similarity to the wavelet. The degree of similarity can be expressed in terms of the wavelet coefficients and plotted as a function of scale and time. The plot reflects how coarse and fine variations in the signal are distributed over time. Periods wherein coarse variations predominate (correlated with "stretched" or large scale wavelets) are periods dominated by low frequency oscillations in the signal, and periods wherein fine variations predominate (correlated with "compressed" or small scale wavelets) are periods dominated by high frequency oscillations in the signal. In time-varying signals, the dominant frequency varies. The shifting "balance of power" shows up in the plot, indirectly providing time-frequency resolution.

It is possible to make infinitesimal shifts and dilations to achieve "continuous wavelet analysis." This is generally unnecessary, however. It is much more efficient, and usually as effective, simply to apply a discrete set of wavelets to the signal under analysis ("discrete wavelet transformation"). Operationally, this can be achieved in a series of interconnected ("cascaded") high-pass and low-pass filters (the "wavelet filter bank"). For this reason, the terms "wavelet" and "wavelet filter bank" (or simply "wavelet filter") may be used interchangeably herein. The context will determine whether the term "wavelet" is being used to refer to a mathematical abstraction (such as a Daubechies order 2 wavelet) or to a wavelet whose parameters are specifically pre-determined by specific settings of filter parameters. It is to be understood that "filterbanks" herein may be implemented entirely in physical (electronic) devices or (for digital filters in particular) in software. Commercially available packages such as the Matlab® Wavelet Toolbox™, The Mathematica™ Wavelet Package and the S+ Wavelet Toolkit provide readily available tools for performing wavelet and wavelet packet analysis. An exemplary method of discrete wavelet transformation subjects the entire signal to a high-pass filter and to a low pass filter to produce two subcomponent signals, one of which has the relatively high frequency content of the original signal, the other the relatively low frequency content. It will be understood that such filtration of a digital signal does not reduce the number of samples in it. In fact, since the method processes the signal twice, the method doubles the total amount of data (at least). Since it is unnecessary to process all these data, it is generally advantageous to remove data points (usually every other one) from each filtered signal. This step is referred to herein (and generally) as "down-sampling." Convolving the signals with the wavelet then yields the same number of correlation coefficients as the number of samples in the original signal.

In general, one of the two filtered signals (usually the low-pass filtered signal) approximates the wavelet more closely than its counterpart, as indicated by the convolution co-efficients (which may be referred to herein as "approximation co-efficients"). In the counterpart signal (i.e., the high-pass filtered signal), approximations to the wavelet occur only in restricted regions. That is, a mathematical "structure" similar to the structure of the wavelet is to be found only upon inspection of the details. Optionally, but usually advantageously, the approximating signal is filtered again (and again) as above and the resulting signals are again (and again) convolved with the wavelet. The original signal may thus be "wavelet decomposed" through successive "levels."

"Wavelet packet analysis ("WPA") differs from wavelet analysis inasmuch as wavelet decomposition proceeds along two paths at once. Not only are low-pass components of the signal under analysis reiteratively decomposed to produce a succession of approximation coefficients, but the high-pass components are treated likewise, producing a succession of "detail coefficients." When a particular mother wavelet function is applied to inspect detail in a signal, it is common in the art to refer to the function as a "father wavelet." The mother and father wavelets are applied together to generate the approximation co-efficients and the detail co-efficients. Taken together, these co-efficients comprise a "packet" of information referred to as a "wavelet packet." WPA thus represents the generalized form of wavelet analysis. U.S. Pat. No. 5,384,725, incorporated herein in its entirety and made a part hereof for all purposes, sets forth both the theory of wavelet packet analysis and exemplary guidance for applying wavelets to a signal to create wavelet packets. Software to implement wavelet packet analysis and a number of other analyses that are within the scope of embodiments of the present invention are provided by MatLab®, for example.

An infinite number of different wavelets (and, consequently, wavelet packets) can be generated by choosing (or designing) different mother wavelets, each of which has advantages and disadvantages depending on the characteristics of the signal being analyzed. For example, one commonly used wavelet function is the Daubechies order 2 wavelet, which has strong fractal characteristics and therefore is often used to analyze waveforms with fractal properties (that is, wherein a portion of the overall waveform recapitulates the shape of the overall waveform). There exist Daubechies extremal phase filters of order 1, 2, 3, . . . N. The order of a Daubechies wavelet function represents the number of filter coefficients necessary to define the mother and father wavelet. An order "N" wavelet packet is generated when a wavelet filterbank having 2N filter coefficients in both the mother and father wavelets is used.

It is convenient to distinguish wavelet packets extracted from a signal by an "x.y" shorthand notation that identifies specific wavelet packets (sometimes also referred to as wavelet crystals). By way of example, a first decomposition of the signal through a low-pass and a high-pass wavelet filter (at a given dilation) separates the signal into two wavelet-convolved sub-bands, one of which measures the similarity of the overall signal to the selected wavelet, the other of which identifies details in the signal that are similar to the wavelet. A second decomposition, performed on the first convoluted signals (after re-scaling the selected wavelet), adds two more wavelet filters to the process and brings the total number of convoluted signals to four. A third decomposition (after again re-scaling the wavelet) brings the total to eight, etc. When x=3, 8 wavelet filters have interrogated 8 sub-bands for detail similarity. Each of the 8 sub-bands comprises a plurality of waves having a range of frequencies, with a "center frequency" mid-range. In the shorthand, the information in packet 3.1 would relate to the wavelet that best matches the detail in the sub-band having the lowest center frequency. The wavelet that best matches the detail in the sub-band with the highest center frequency would be referred to as packet 3.8. It is to be noted that the "best sub-band" of the 8 interrogated will be the one from which the best determination of muscle effort can be extracted by the analysis outlined below. Note also that if an effective analysis requires more decompositions, disproportionately more convolution calculations will be required (e.g., 4 decompositions requires interrogation of 16 sub-bands, etc.), raising the cost of such an analysis. Moreover, in some embodiments herein, where real-time processing is preferred, data storage is not a practical means of moderating such cost.

The term "real-time" as used herein refers to a response time of a system in operation, which response time is sufficiently short to allow an output from an operation to serve as an input to that operation.

The term "calibration factor" refers herein to a reference standard that allows a practitioner to adjust or convert a measurement obtained by one method or measuring instrument to its equivalent as measured by another method or instrument.

Terms Related to Musculoskeletal Analysis:

As used herein, the term "strength" (except as the context may otherwise admit) refers to physical strength; that is, the maximum ability of a person or animal to exert force on a physical object (including among such physical objects a part of the person's or animal's own body) by contracting one or more muscles.

The term "muscle body," as used herein, refers to any assembly of muscle fibers or bundles of such fibers. In skeletal muscle (also referred to as "voluntary" muscle), such assemblies are delimited by tendons which attach to processes of the skeleton. It will be understood, however, that some embodiments of the invention may apply to smooth muscle (also referred to as "involuntary" muscle) or cardiac muscle. Thus, the term "muscle body" is to be construed broadly herein. It encompasses any "muscle" that can be assessed according to an embodiment of the invention. It will also be understood that some embodiments of the invention may find use in evaluating a plurality of muscle bodies acting in concert. Such a plurality may be referred to herein as a "muscle group." Alternatively, where the context so admits, the term "muscle group" may be used in connection with the well-known classification of muscles according to the type of muscle fiber predominantly contained in them (see below).

"Muscle effort" refers to the contribution of the musculature to work done by the limbs or body. This includes not only the generation of forces but also the timing of the forces (in onset and duration), as well as the distribution of forces, all of which can significantly influence the effort required of an individual muscle to execute a task, independent of anatomical factors such as sites of muscle origin, or sites of muscle insertion. A muscle body can have multiple origins and multiple insertions, such that the effort of a muscle is translated into a number of different forces being imposed on different elements of the skeletal system. Therefore, muscle effort represents a more complete description of total muscle activity than muscle force generation per se. The term "effort" applies, further, to any element (e.g., fiber, fiber bundle, muscle body) of a muscle for which the generation and timing of such force can be measured, a muscle body in particular. Muscle effort can be expressed in units of force.

The term "absolute muscle effort," as used herein, refers to the force-generating capacity of muscle under contraction independent of any anatomical arrangement of the muscle body. Muscle effort comprises (1) forces developed by the muscle during a contraction, (2) the time needed to develop those forces, the measure of which is preferably expressed in units of time to peak force and (3) the "time-ordering" of the forces, expressible in units of force as a function of time (i.e., a "time-varying" function). Time-ordering creates a profile of force developments—an "effort generation profile"—over the duration of the contraction. The effort generation profile provides insight into the episodic nature of the activity of a muscle during a contraction.

The vibromyographic signal, "raw" except for its processing by wavelet packet analysis, is a preferred determinant herein of the effort produced by a given muscle in an individual. Indeed, it is an objective herein to define "effort" in the unitless terms of peak envelope values. To compare values between individuals, however, where anatomical differences come into play, it is preferable to calibrate the output of wavelet packet analysis into units of force to create a "muscle force expression." As noted, force values can be factored to make them comparable among different individuals by making simple mechanical measurements on the individuals being compared. Such determinants may be referred to herein as "comparative determinants."

Unless the context otherwise admits, the term "contraction," when used in relation to muscle activity or "muscle function," refers to tension in a muscle, whether or not that tension is associated with shortening of the muscle. A muscle that shortens under tension is said to be in "concentric" contraction, a muscle that lengthens under tension is in "eccentric" contraction. In "isotonic" activities, whether concentric or eccentric, the change in length is associated with constant muscle tension. A muscle that shortens at a constant rate over a period of time is undergoing "isokinetic contraction." A muscle that does not change in length as tension in the muscle increases is in "isometric" contraction. The term "functional contraction" refers herein to a contraction that is not controlled so as to isolate, in pure form, any of the above-defined contractions. Functional contractions occur in the normal course of a subject's activities.

"Muscle coordination" as used herein reflects the timing and strength of contraction of multiple muscles during an activity. Such multiple muscle activities generally comprise isometric and isotonic contractions. Under these conditions, measurement of the isometric elements may be distorted by "tension artifacts" and measurement of isotonic elements may be confounded by "shortening" artifacts. These artifacts represent certain elements of the "motion artifacts" (see below) that may distort vibromyographic signals.

As used herein, the term "joint stability" refers to the degree to which a skeletal joint that is capable of articulating (i.e., not fused or ankylosed on the one hand or freed of its attachments to muscles on the other) resists displacement by an applied force. The degree of resistance with respect to any given joint can be measured both directly and by means of embodiments of the present invention in a plurality of individuals categorized, without limitation, by sex, age, weight, body mass index, and any of a variety of measures of fitness to create for each joint a database to serve as a "stability index" for that joint. For example, if the average person's ankle in a particular category of subjects remains static until "X" foot-pounds of torque are applied to the joint, "X" (or another measure of central tendency) becomes the reference standard for the ankles of subjects in that category. It is to be understood that joints, whether in stasis or in dynamic articulation, may be stable or unstable, depending to a large extent on the "balance" of forces exerted on the joint at any instant by muscles that are "paired." The forces exerted on the joint by each member of the pair may be "antagonistic" (tending toward articulation controlled by the lengthening of one member and the shortening of the other), "complementary" (two or more different muscles that work in a coordinated fashion around two or more joints to accomplish a functional activity) or "supplementary" (two or more different muscles that work in a coordination fashion around a single joint to accomplish a functional activity, also referred to as synergistic).

"Dynamic joint stability," as the term is used herein, refers to force balances in a joint over time and positional changes. A "dynamic stability index," accordingly, takes time into account. "Joint laxity," which is reflected by forces that must be applied to extend a joint, relates only weakly to dynamic joint stability, as noted above.

Muscle "balance" refers to the relative effort that antagonistic, complementary or supplementary muscles must generate in an activity. Whether or not two or more muscles are in balance is determined by the ratio of efforts generated, especially as compared to corresponding ratios in reference subjects.

Muscles are characterized by the rate ("twitch rate") at which their individual fibers contract (usually spontaneously). A fiber may be categorized as a Type I ("slow twitch") fiber, or a Type II ("fast twitch") fiber. A muscle body comprising a preponderance of Type II fibers tends to generate force more quickly than a muscle body dominated by Type I fibers. It is often referred to as a "Type II muscle." Muscles are "grouped" by fiber type. As noted above, the term "muscle group" may also refer to a plurality of muscle bodies that cooperate in effecting movement of a body part. Herein, the context will distinguish between the two references "Bursting power" is sometimes evaluated through dynamometer measurements, though it is more usually evaluated through a specific performance measure (e.g., height of a jump). The assessment of interest is the peak effort generated by a particular muscle group, and the time required to generate this effort.

"Impact," as used herein, refers to a body contacting another body with sudden deceleration.

A "goniometer" herein is an angle-measuring device.

A "closed chain activity" refers herein to human movement (i.e., an "exercise") under conditions in which the distal end of an extremity is constrained. "Constraint" in this context typically refers to the distal extremity being supported throughout the exercise by a floor or a wall. In "open chain activities" there is no such constraint. It will be understood that many common activities, such as walking or running, are a mixture of closed chain and open chain activities.

"Torque" herein refers to the ability of an applied force to rotate an object about an axis, or about a fulcrum, and therefore has the units of distance multiplied by force (e.g. ft-lbs).

"Dynamometer" herein refers to a machine used to measure torque and/or rotational speed (rpm) produced by a prime mover (e.g., the net torque produced about a joint by a combination of muscle forces). It is to be noted that torque, measured with a dynamometer tends to provide more accurate measurements, but muscle effort may be measured under some circumstances simply by causing a muscle to lift a weight or "load" (so-called "free weights").

An "accelerometer" is, in principle, a mass on a spring, with a damping element. When a force displaces (i.e. accelerates) the mass, the accelerometer produces a recordable signal proportional to the acceleration. The strength of the damping element can be varied to adjust the frequency response of the system. It is not intended that the invention be limited to any particular embodiment of the accelerometer principle. Any device that responds to an applied acceleration and is sensitive in the frequency regime associated with the vibrations that contracting muscles produce is within the scope of the invention. In preferred embodiments, the accelerometer may be applied to the outer surface of the skin of a subject, positioned over the muscle of interest. One identifies a surface area that overlies the muscle body of interest and positions the accelerometer on at least a portion of that area to create a "positioned" accelerometer, i.e., an accelerometer whose proximity to the muscle body is such that vibrations arising from the muscle can sense vibrations arising from the muscle. That is, a "positioned accelerometer" is close enough to the muscle to pick up the vibrations. In a most preferred embodiment, this positioning is maintained throughout any period of data acquisition by an accelerometer-constraining means (or "restraining means") that keeps the muscle body and the accelerometer in an effectively constant relationship to one another. It is to be noted that the applicants, under the guidance of prior art (which teaches that pressure on a positioned accelerometer distorts its output), resisted this embodiment until they found, empirically, that pressing the accelerometer against the muscle body actually improves its performance as used herein.

Although a mechanical means of constraint ("restraint") is preferred, other means for acquiring muscle contraction-related vibrations wherein acquisitions are not distorted by macroscopic motions that the contracting muscle induces, or wherein such distortions are reduced, are within the scope of the invention, so long as the microscopic (vibrational) movements of interest (i.e., the "vibromyographic signal") can be isolated for analysis. Furthermore, although an accelerometer that emits an electrical signal (i.e., a waveform characterized by variations in electrical potential) as its output is preferred, the various embodiments of the invention encompass any other type of signal that comports with the frequency regime of vibromyography, or that can be made so by suitable pre-processing.

As used herein, the term "biofeedback" relates to methods wherein a subject receives an extrinsically acquired signal that relates to a particular function or activity of the subject such that the subject can change the signal intrinsically.

GENERAL DESCRIPTION OF THE INVENTION

Given the need for accurate assessment of muscle activity in terms of strength, coordination and joint stability under a variety of conditions, and given the inability of muscle dynamometers to provide such assessments except under specialized conditions, surrogate measurements thought to be indicative of strength, coordination or stability, such as the electrical activity and the high-frequency mechanical activity (i.e., vibration or "sound") of muscles, have been pursued. The former, electromyography ("EMG"), is the most well known, but the latter, vibromyography ("VMG") has certain advantages. The present invention, in preferred embodiments, employs VMG to provide a means of evaluating a muscle or a muscle group for its strength, its capacity to contribute to coordination of a physical activity, and its capacity to contribute to joint stability, without need of complicated anatomical measurements and calculations to evaluate these indicia of muscle effort, except for purposes of initial calibration. In one embodiment, the present invention extracts estimates of muscle effort during contraction in real-time, i.e., without needing to make calculations "after the fact" using stored data.

Electromyography.

EMG is a means of recording the muscle electrical action potential as it travels down the length of the muscle cells in a muscle body. The technique is an electrical potential measurement. Like all electrical potential measurements, it is a relative, or differential measurement. That is, an electrical potential is always measured relative to a reference point. While invasive EMG techniques (involving the insertion of wires or needles into the muscle body) have been developed as a means to more accurately assess muscle activity, PTs and trainers generally utilize surface electromyography (SEMG) techniques. SEMG requires the attachment of at least two electrodes to the surface of the skin above the muscle group of interest, using conducting electrode gel. Electrode size, electrode spacing, electrode orientation relative to the orientation of the muscle group, and electrode placement relative to the location of the motor nerve all affect the magnitude of the SEMG that will be recorded. Because SEMG measurements are relative, they must be normalized to a reference contraction level, typically the maximum voluntary contraction level ("MVC"). SEMG has significant limitations in this respect, particularly in the realm of muscle rehabilitation where the function of the musculoskeletal system has been compromised. Moreover, SEMG recordings are commonly paired with Fourier analysis (or a derivative of Fourier analysis) to assess muscle activity, which also has significant limitations.

Fundamental limitations in using SEMG to analyze muscle function include:

1. Fourier analysis is applicable only to statistically stationary signals but, when muscles are active, the myographic signals they produce are non-stationary. Extensive corrective computations are therefore required, resulting in relatively crude estimates of muscle effort during dynamic muscle activities.

2. Even when non-stationarity can be ignored, Fourier analysis requires relatively prolonged recording durations to ensure accurate frequency resolution (that is, a long period of time relative to the world of athletics and/or rehabilitation where movements can be and often are executed in fractions of a second).

3. Artifacts related to acquiring a differential signal, that is, a traveling wave whose "read-out" has no meaning except with respect to a reference (which is how SEMG signals are acquired) render the frequency content of the signal physiologically irrelevant (i.e. not directly related to muscle contractile frequency).

Practical limitations of SEMG include:

1. Standards of SEMG recording have not been adopted, and the nature of SEMG requires that recordings be collected with the same electrode size, spacing, skin condition, placement and materials in order to be comparable over time and from test to test. Therefore, even though SEMG has been in use for more than one hundred years, no coherent body of knowledge about electrical signals from muscles exists or is expected to exist.

2. Skin condition, including perspiration, hydration, epidermal thickness, and exfoliation, can have a significant effects on the resultant SEMG signal.

3. Interpretation of SEMG signals from subjects whose movement is not strictly controlled is difficult.

4. SEMG/force correlations are monotonic only from about 20% to 80% of a person's MVC. Forces that cause sports-related injuries are most often above this range (i.e. >80%), so SEMG cannot provide information about muscle dynamics in important application areas.

Vibromyography.

As a means of addressing the limitations of SEMG, numerous investigators have pursued the concept of measuring the microscopic muscle vibrations or "sounds" (i.e., a "pressure wave" propagated through a material by means of alternating compressions and expansions of the material) associated with contracting muscle to assess muscle function. That muscles make an audible sound when they contract has been known for over 400 years. Early attempts to detect these sounds and record them as microscopic muscle motions utilized small microphones. However, small (<1 cm) microphones have poor frequency response (i.e., transfer functions close to zero) at frequencies below 100 Hz, which is the frequency range in which most muscle sound energy is located.

While laser displacement technology and other approaches have been utilized to record muscle microscopic motion during contractions, the most common technique is to utilize small (micro-electro-mechanical) accelerometers to record the vibrations emanating from the muscle body on the skin surface above the muscle body. This technology is often referred to as mechanomyogrphy (MMG) or vibromyography (VMG).

VMG has several distinct advantages over SEMG. These include:

1. VMG signals are acquired by making measurements at but one point on the skin. Thus, VMG signals are inherently less complicated and so are simpler to analyze than SEMG signals.

2. By virtue of being a single point measurement that uses a sealed transducer, VMG does not require the same strict "standardization" as SEMG recordings, such as inter-electrode spacing, skin treatment, location on the muscle etc.

3. MEMS (micro-electro-mechanical) accelerometers are easily miniaturized, relatively inexpensive, and can be designed to have a frequency response that overlaps the normal physiologic range of muscle contractile frequencies (0-1 KHz).

4. VMG signals are a result of the mechanical contractile activity of muscles, and therefore more directly reflect the resultant forces produced by muscles.

5. Transducers involved in the collection of VMG signals from skeletal muscle are quite insensitive to skin conditions, making them useful during a wider variety of activities and conditions than SEMG measurements.

The modern era of VMG development, using small microphones, began in the 1980s. By the mid-1990s, relatively low cost micro-electromechanical accelerometers were becoming commercially available, and these small accelerometers permitted direct comparison to SEMG techniques. Matheson, et al. (Scan J. Rehab Med 29:29-35, 1997) undertook one such direct comparison. Utilizing three-second recordings and analyzing the SEMG and VMG signals using Fourier analysis in a test-retest experimental design, Matheson et al. concluded that "VMG is a better discriminator of absolute muscle force values between subjects than SEMG." However, Matheson et al. also noted that this correspondence extended only up to voluntary contractions of approximately 60% of maximum. This inability to report on the full range of muscle forces resulted in VMG research being largely abandoned by the muscle physiology community, and so the technology never entered the clinical realm.

In an attempt to address the lack of correlation between VMG data and high absolute muscle forces, Cole & McLeod (2006) applied time-frequency analysis techniques (Wavelet Packet Analysis—WPA) to VMG recordings. Utilizing an experimental set-up similar to that of Matheson (3-second recordings from the brachio-radialis), their approach demonstrated that it was feasible to overcome the 60% MVC limitation of VMG recordings. Reflecting Matheson's results, when Cole & McLeod (2006) determined isometric flexion force in the brachio-radialis directly from VMG recordings by plotting average (root mean square) magnitude as a function of the loading force (FIG. 1A), they found that a plateau is reached at around 60% of maximum voluntary contraction. When the VMG recordings were wavelet-decomposed so as to produce wavelet packets and the RMS values of the resulting packets were plotted (FIG. 1B), a much better, monotonic representation (correlation >90%) to loading force was observed. The combination of wavelet packets (wavelet packets 9.7 & 9.9), however, was applied to data averaged for 24 individuals, not to single individuals. Subsequent work by others has confirmed that wavelet analysis approaches can be beneficial in evaluating VMG data. However, these investigators have all focused on the region of the VMG spectrum where the highest amplitude intensities were observed (typically 30-40 Hz) [Beck, et al., (2009) A wavelet-based analysis of surface mechanomyographic signals from the quadriceps femoris].

The techniques utilized by Cole and McLeod 2006, and Beck et al, 2009 have several significant limitations that prevent acceptance of this technology in the clinic or by trainers. These limitations include:

1. The analysis techniques reported by Cole & McLeod 2006 and by Beck et al 2009 require relatively long recordings (similar to the three second recordings of Matheson), which are too long to be useful in a typical clinical/training session where functional evaluation is taking place. Functional muscle activities take place in a time as short as 0.25 seconds. Therefore, for a muscle assessment technique to be clinically useful, it must be accurate on a time scale of 10-50 milliseconds. As confirmation, attempts to utilize the technique of Cole and McLeod 2006 to obtain assessment of rapid muscle contractions by using one second data analysis segments resulted in greatly increased variability in the predicted muscle force. FIG. 2 displays VMG:Force data acquired using a static analysis (isometric) technique with 1 second data segments. Large variations in predicted muscle force are evident above approximately 150 Kg.

2. The algorithm reported by Cole and McLeod also required nine levels of wavelet decomposition to identify the crystals that provide the best correlations to absolute muscle force. Data cannot be collected and computed at rates fast enough to accommodate this level of analysis in real-time. In the clinic or gym, however, real-time processing is highly advantageous. The PT or trainer does not want to collect muscle data and then analyze it after the fact; rather, real-time analysis that is within the capability of present-day portable computers is needed so that an evaluation of muscle activity can be made during the functional activity to provide timely coaching or biofeedback.

Figure 3:
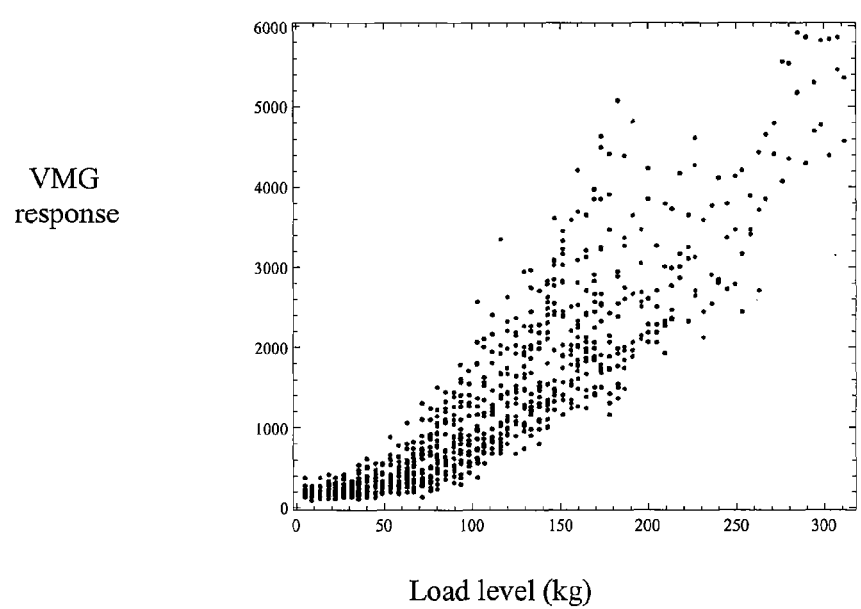
FIG. 3. VMG response vs. load force for 24 individuals. Note that at a load level of 180 Kg (x axis), the VMG assessment obtained using wavelet packets 9.7 & 9.9 vary by a factor of five. This level of variation would significantly limit the use of this technique in the clinic or training facility and the large number of decompositions would obviate real-time use.

3. While averaged VMG data obtained from multiple people demonstrated an excellent correlation to absolute muscle force, measurements on individuals using the technique of Cole & McLeod 2006 showed that force estimates varied considerably (FIG. 3). At a load force level of 180 Kg (x-axis), the VMG assessment obtained from wavelet packets 9.7 & 9.9 varied by a factor of five. This level of variation would significantly limit the use of this technique in the clinic or training facility.

4. The analysis protocol and algorithm reported by Cole & McLeod was developed for use under isometric muscle contraction conditions. Physical therapists and trainers need to be able to assess muscle function under conditions of motion—preferably closed chain functional activities such as stepping, squatting, and lunging. While useful for long-term isometric contractions, further testing of the approaches proposed by Cole and McLeod 2006 and Beck et al 2009 demonstrated that they are insufficient to be useful for evaluating concentric and eccentric muscle contractions under functional testing situations.

Any method that is likely to be useful for such evaluations must work without long datafiles or time-consuming computation. One possibility, then, would be to focus on data that best captures the peaks of the power spectrum of the VMG signal (where most of the vibrational energy of the VMG signal is centered). Surprisingly, however, the applicants have found that the most effective strategy is to actually remove these components from the VMG signal, which uncovers much smaller, higher frequency components. The latter evidently reflect (or predict) the observed large muscle forces with more fidelity than the highest energy components. Of course, to extract the small, high-frequency components, one must use a highly sensitive sensor (such as an accelerometer) and ensure that signals have minimal noise.

DETAILED DESCRIPTION

A. Real-Time Vibromyography

1. Measurement of Muscle Body Radial Accelerations.

Figure 21:
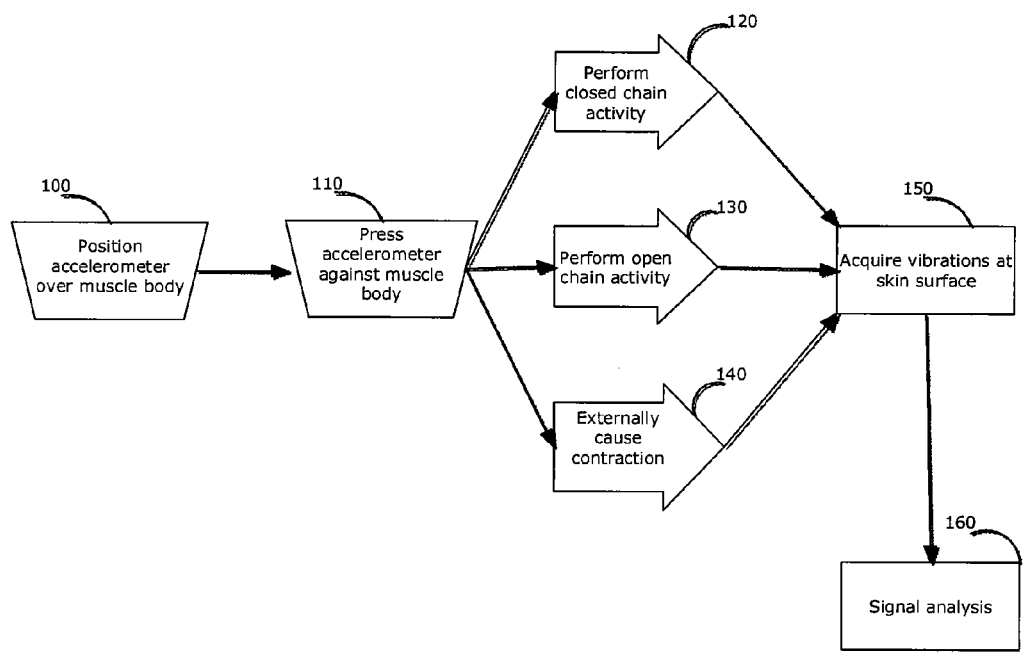
FIG. 21. Process flow diagram of steps for acquiring vibromyographic signals from a subject engaged in alternative activities (closed chain, open chain, and externally induced).
Figure 24:
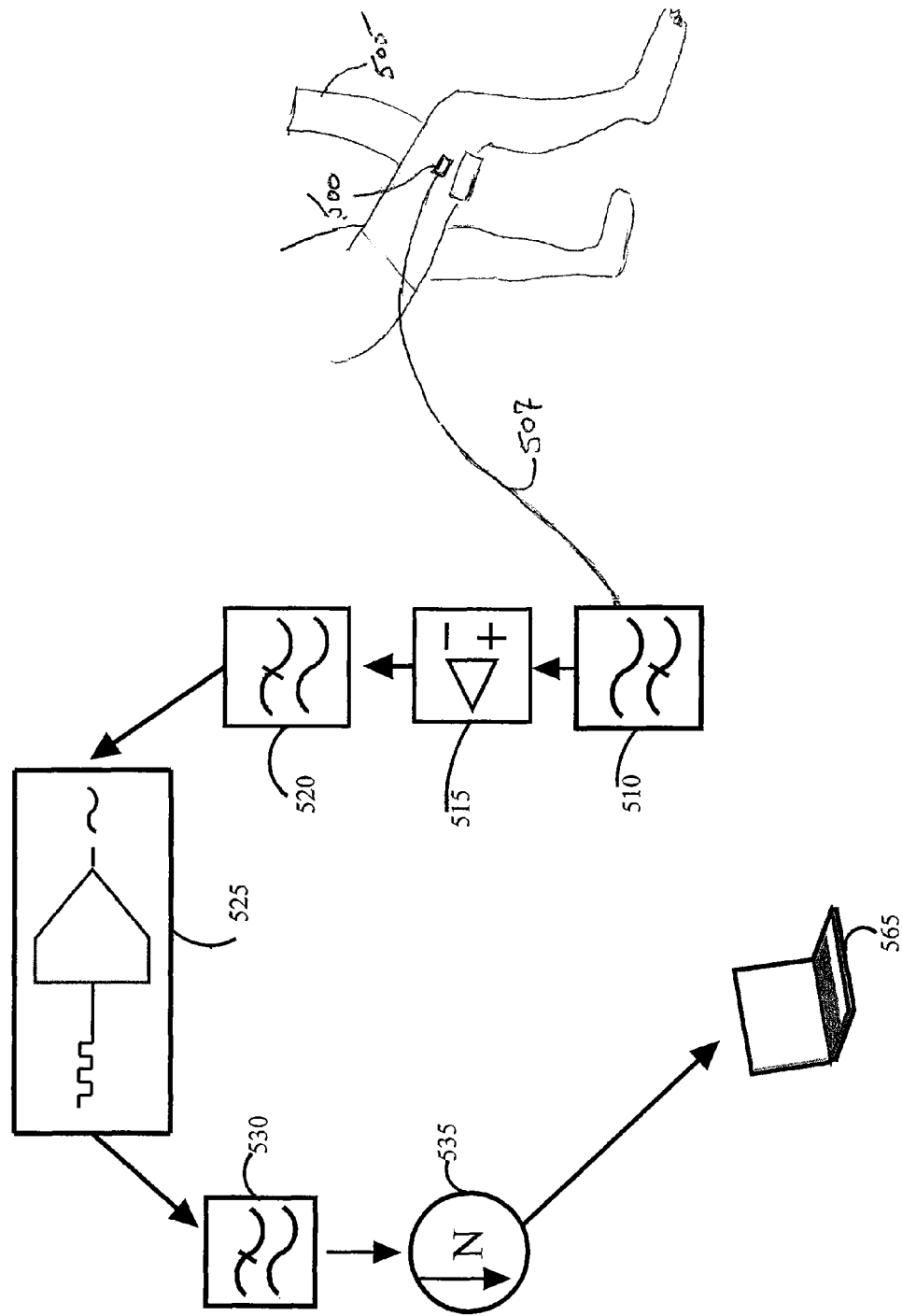
FIG. 24. Schematic of apparatus for acquiring and processing vibromyographic data.

The first steps of the process are flow-charted in FIG. 21. In a preferred embodiment, a micro-electro-mechanical accelerometer is utilized as the muscle vibration sensor. An accelerometer is positioned (100) on a muscle body of a subject. As a non-limiting example, a Kistler™ Model 8305A, which has a working range of about ±2 g (g=9.8 m/s$^2$) over a 500 Hz bandwidth; sensitivity of 500 mV/g, and noise density of 20 µg/Hz$^{1/2}$ may be used. More specifically, the noise floor, i.e., the square root of required bandwidth times the noise density, in preferred embodiments, is <300 µg. To achieve even lower noise floors, with greater sensitivity, the Silicon Devices Model 1221L-002 accelerometer may be used. Although micro-electro-mechanical accelerometers are preferred, other accelerometers are within the scope of the invention, and the means by which the accelerometer works (piezoelectric crystals, gas bubbles, photonics, etc.) is not limiting. The outputs may be analog or digital. Advantageously, but without intending any limitation, an accelerometer selected for use in embodiments of the invention may be single axis with the axis of sensitivity aligned perpendicular to the muscle body; have bandwidth of about 150 Hz or more, and preferably be "small" relative to the muscle body/group being assessed (e.g., accelerometers of about 1 cm$^2$ are sufficiently small for performing measurements on the large muscles surrounding the knee or elbow). Note that for the analysis of activities involving impact, sensors with a higher working range of 5 or 10 g (50-100 m/s$^2$) are preferred. A positioned accelerometer 500 is represented in FIG. 24.

2. Motion Artifacts and Other High Energy Vibrations.

Figure 4:
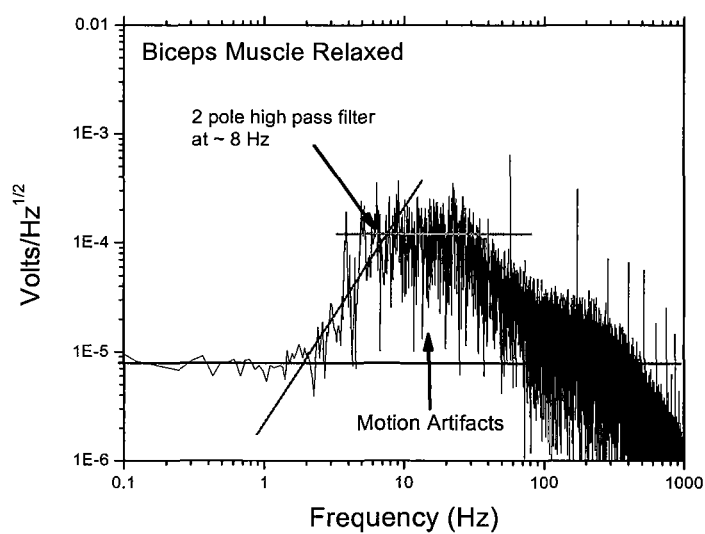
FIG. 4. VMG signal from the upper arm (biceps) when relaxed. (High-pass filtering at 8 Hz). A broad band of energy is evident up to 30 Hz as a result of macroscopic motion of the arm.
Figure 5:
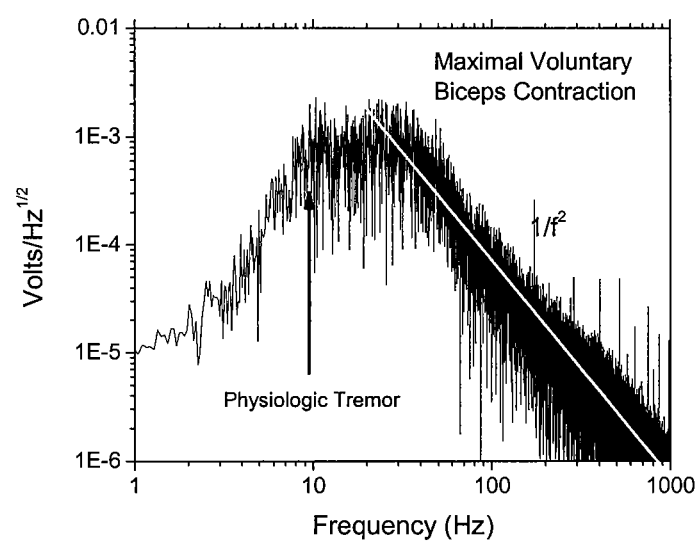
FIG. 5. VMG signal from the upper arm (biceps) during contraction. Distinct tremor component centered near 10 Hz is evident.
Figure 7A:
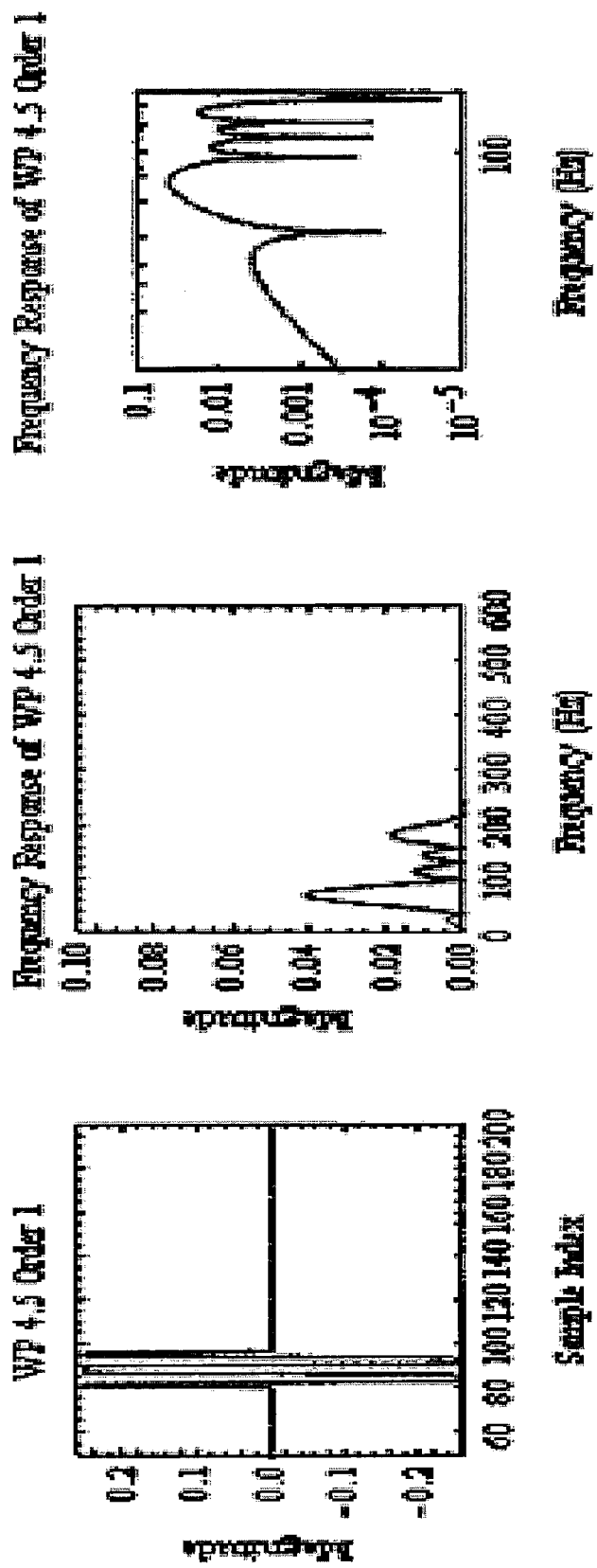
FIG. 7. Characteristics of wavelet packet 4.5, generated by applying Daubechies mother wavelets of orders 1-13 to VMG data sampled at 500 Hz. Packet 4.5 represents one of the preferred packets for the analysis of VMG data.
Figure 7B:
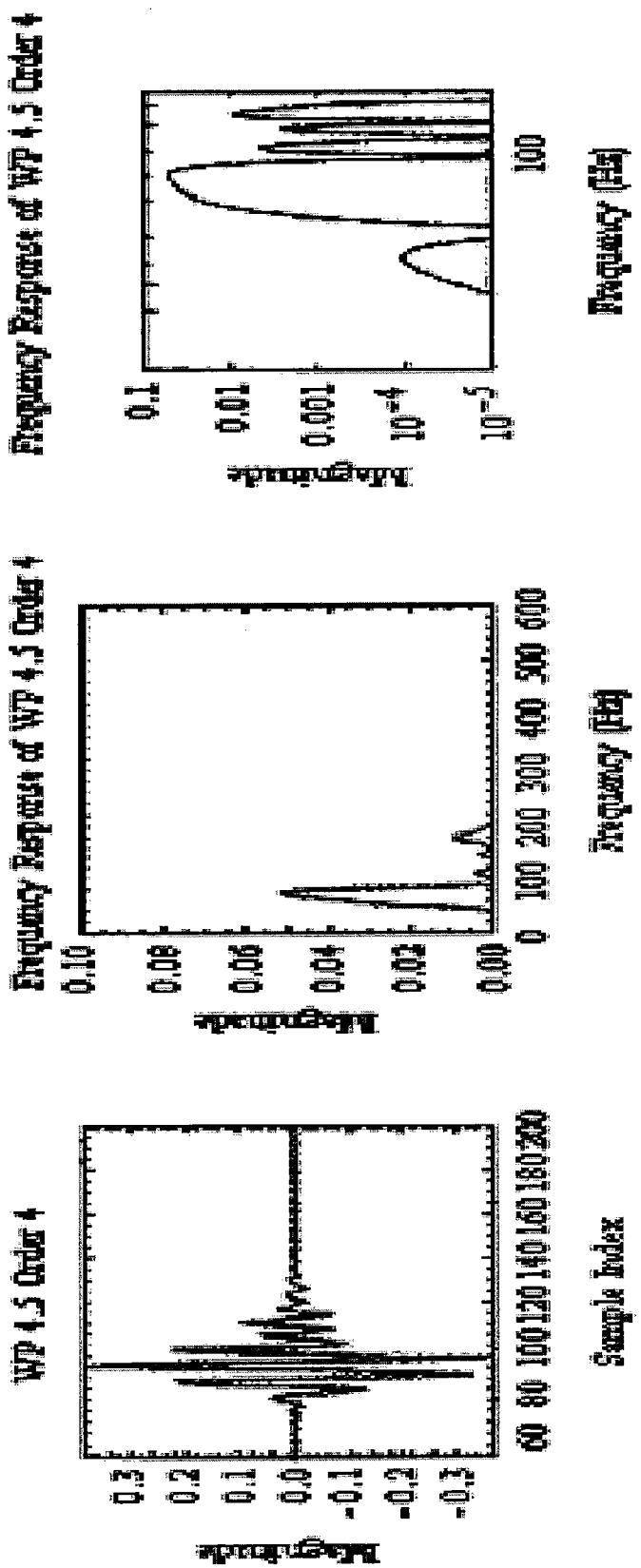
Figure 7C:
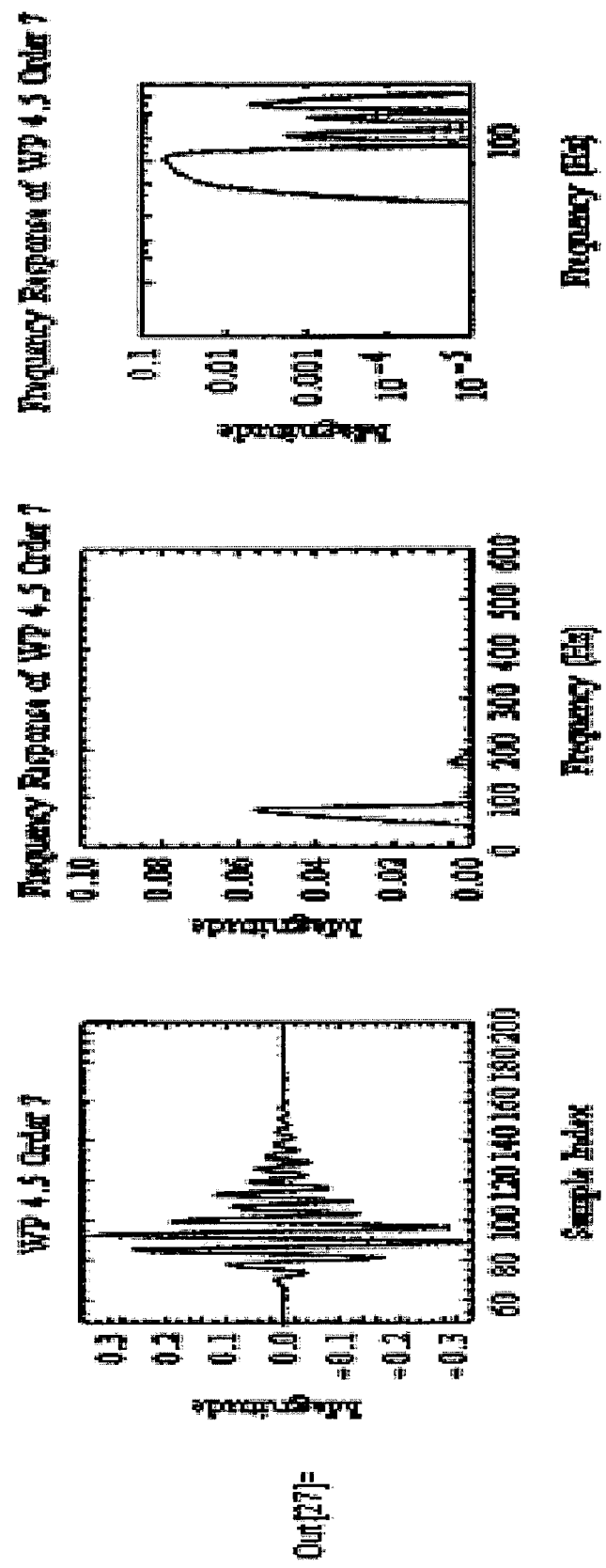
Figure 7D:
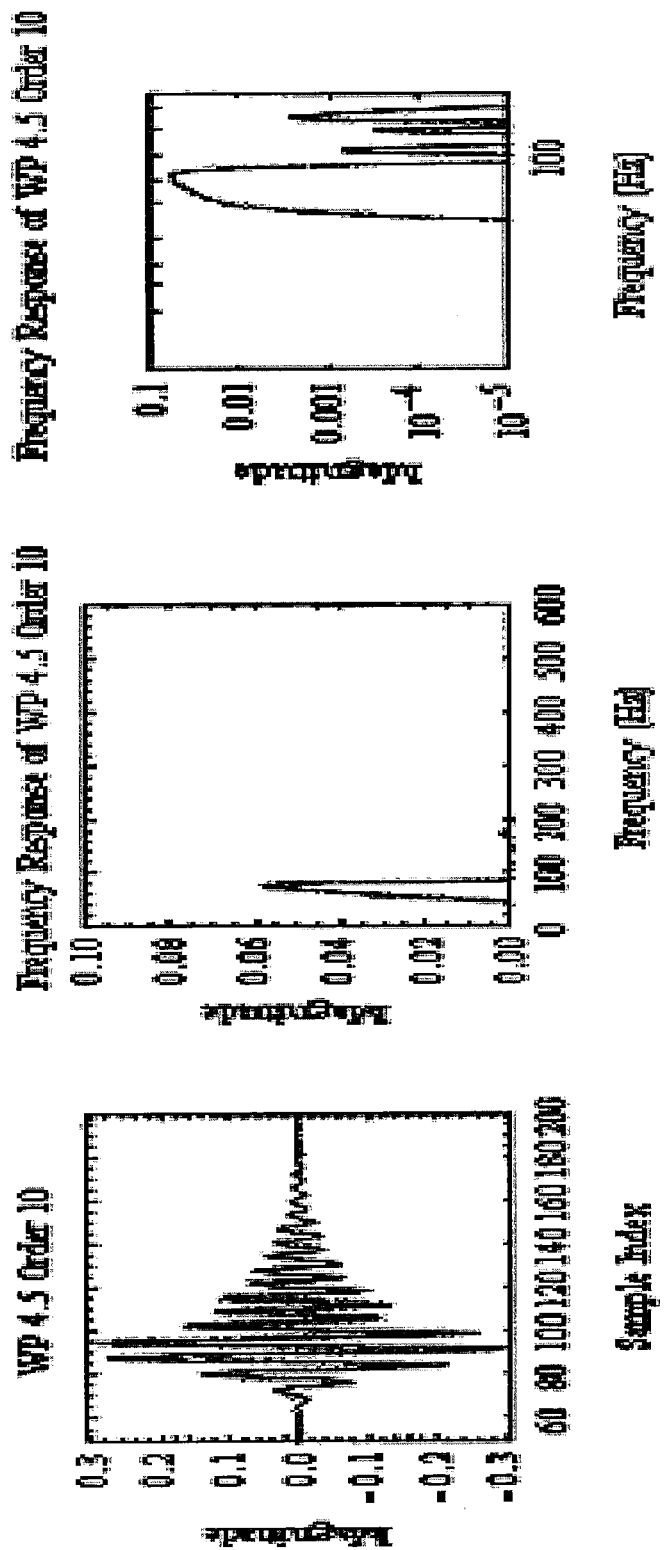
Figure 7E:
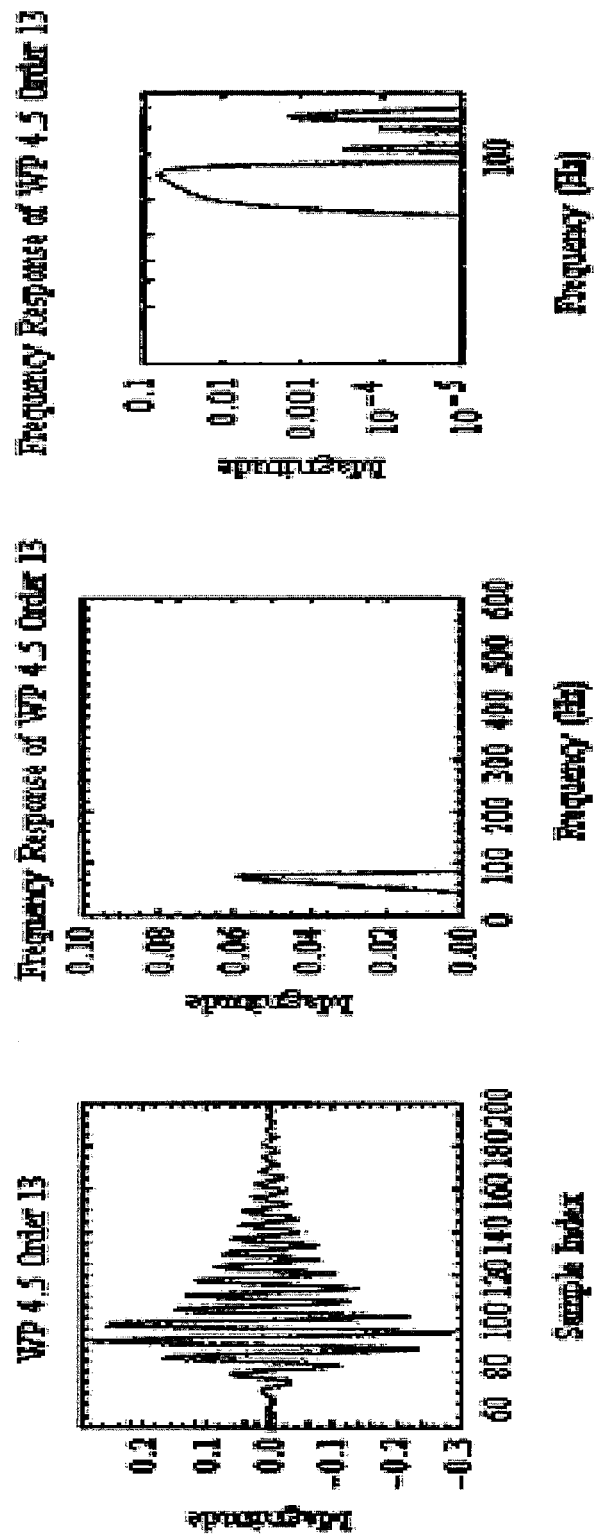
Figure 22:
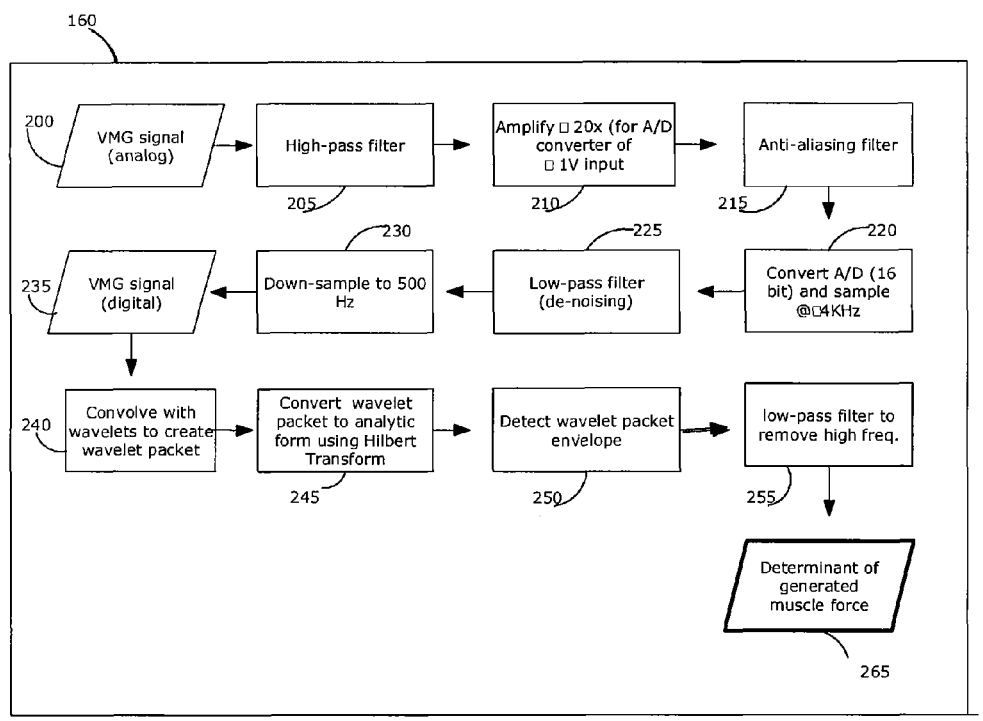
FIG. 22. Process flow diagram of steps for pre-processing a vibromyographic signal and obtaining from the signal, by means of wavelet packet analysis, a determinant of muscle force.
Figure 23A:
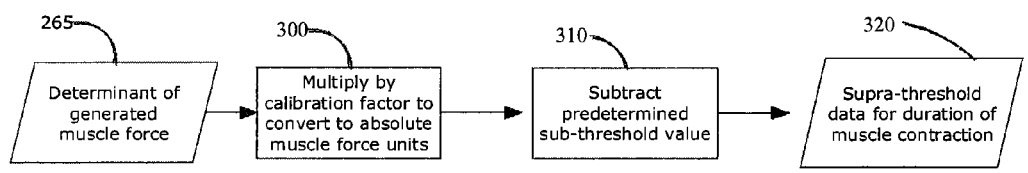
FIG. 23A. Process flow diagram for expressing a determinant of muscle force in units of force.
Figure 23B:
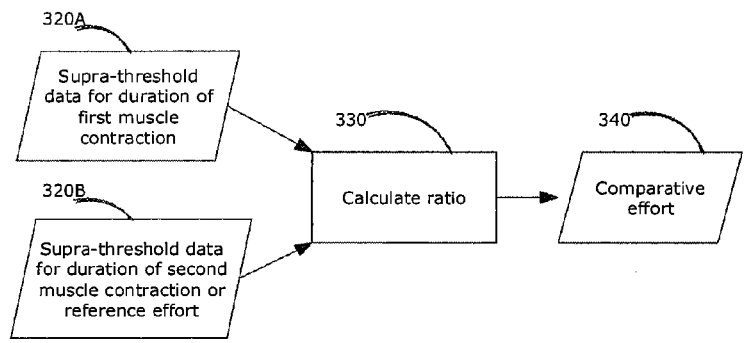
FIG. 23B. Process flow diagram for comparing performance of two muscles.

Closed chain activities typically involve large limb and muscle motions. An accelerometer attached to the skin above a muscle body undergoing assessment will detect such motions, but they only mask the small, high frequency vibrations that embodiments of the present invention utilize to directly assess muscle effort. A generally advantageous step in obtaining reproducible closed chain muscle effort evaluations using VMG, therefore, is the suppression of the various high energy signal components inherent to closed chain activities. The signal processing steps flow-charted in FIG. 22 are directed in part at achieving this result. High energy vibrations arise from a variety of physiologic processes. One type of artifact is the macroscopic motion of the muscle body upon initiation of contraction. Such macroscopic motion artifacts are exemplified in FIG. 4, which shows a VMG recording (high pass filtered at 8 Hz to remove the very low frequency accelerations associated with limb motion) from the biceps of a relaxed upper arm. A broad band of high amplitude spectral components is evident up to 30 Hz as a result of macroscopic motion of the muscle. Muscle tremor (oscillating motions of the muscle body), generally occurring in the 8-12 Hz region, is another source of motion artifact (FIG. 5). A third type of high energy artifact is "impact spikes" that occur at the start of a motion when an extremity makes contact with a constraining surface. Indeed, all of the high energy components of the vibration spectrum are "artifacts" in the context of the invention in its various embodiments. As noted above, the objective, in contrast to the guidance generally provided in the VMG literature, is to remove these components in order to focus the analysis on the underlying low energy, higher frequency vibrations which serve as the fundamental components of muscle contraction.

3. Macroscopic Skin Movement.

An additional type of motion artifact is associated with the movement of the skin relative to the underlying muscle body. While the common assumption among practitioners of VMG (or MMG) is that restraint of the accelerometer will suppress the vibration signal (which is correct if one is trying to pick up the lower frequency, high energy signal components) the applicants, who focus on the higher frequency, low energy components of the VMG signal, have found that compression (110) of the accelerometer against the muscle body significantly enhances the recording of the vibrations of interest. Therefore, in preferred embodiments, the vibromyographic measurement is made under conditions wherein movement of the skin (and therefore the accelerometer) over the muscle group of interest is restrained, and in addition serves to compress the accelerometer against the muscle body to increase the accuracy of the recording. In one embodiment, the vibromyographic sensor is held against the skin over the muscle group of interest by means of an elastic strap 505 (FIG. 24). A variety of elasticized materials can serve in this capacity, but a material capable of repeatedly experiencing a percent strain of 25-50% and returning to its original length is preferred. Similarly, a non-allergenic material, preferably washable or disposable, is preferred. Advantageously, the strap (which may be composed of two or more materials, one of which is elastic) is sufficiently wide (e.g., 8-12 cm for the vastus lateralis) that the muscle body is compressed after application, and sufficiently long (e.g. 50-150 cm for recording from muscles of the thigh) to permit at least one full wrap around the limb or body segment under investigation. Further, constant tension is preferred to insure stable, reproducible measurements (e.g. by using a material with a low coefficient of elasticity, the tension on the skin will be relatively constant independent of the extent to which the strap is stretched. Embodiments are also contemplated wherein the skin's freedom of movement over the muscle body is constrained by a wrapping material and the sensor is placed atop the wrap. Also, the sensor may be affixed to the wrap or embedded therein.

Referring again to FIG. 21, in various embodiments, an accelerometer pressed against the skin over a muscle body can be used to acquire vibrations at the skin surface (150) during closed chain (120) or open chain (130) activities, or during a contraction caused by external stimulation (140), and processed as outlined in FIG. 22.

4. Preprocessing of the Accelerometer Signal.

Turning now to FIG. 22, the signal is first pre-processed. One objective of pre-processing is to remove high energy vibrational components associated with macroscopic muscle motion or skin motion in order to extract for analysis the low level, higher frequency components of the VMG. To accomplish this, the raw accelerometer output 200 is filtered (205) through a high pass analog input filter with a preferred cut-off frequency in the 25-50 Hz range, and a most preferred cutoff frequency near 30 Hz. For example, without intending any limitation, a three pole, 30 Hz, high pass analog input filter may be used. A 5 pole Butterworth filter will provide a maximally flat pass-band, though with relatively slow cut-off; a 5 pole Type 2 Chebyshev filter will provide faster cutoff, but with ripple in the stop band; a 5 pole elliptic filter provides maximally sharp cutoff, but produces ripple in both the stop and pass bands. Preferably, the output of the accelerometer is amplified (i.e. an active filter can be utilized) (210). Amplification by a factor of 10-500, preferably a gain of 20×, will normally be required when using the accelerometers specified above (e.g., SDI 1221L-002), with the goal being to utilize the full range of a 16 bit A/D converter (e.g. the Linear Technology Corp. LTC2450, a 16-bit delta sigma A/D converter). The signal is anti-aliased (215) in at least a minimal (i.e. one-pole) filter prior to any analog to digital (A/D) conversion (220), though higher order filtering will improve performance.

Digitization schemes comprising an analog to digital converter having 12 bit resolution or higher are within the scope of the invention. Lower resolution A/D conversion provide adequate muscle effort assessments if generated forces are small, but, unless very low noise accelerometers are utilized, large efforts associated with near maximal voluntary contraction levels may be better determined using data converted at higher resolution. Because assessment over the full range of voluntary muscle contraction is preferred, minimizing noise and maximizing resolution are both preferred. In one embodiment, the amplified signal is low-pass filtered (225) at a cutoff frequency between 250 Hz to 2 KHz (preferably 360 Hz) to prevent the introduction of digitization artifacts. Any anti-aliasing measure that provides at least the Nyquist sampling frequency (twice the highest frequency in the signal of interest) is within the scope of the invention. It is to be noted that anti-aliasing step 215 may be applied before, during or after amplification, without limitation. In one embodiment, the digitized vibromyographic signal is "de-noised" prior to wavelet packet analysis by low pass filtering (225) at 200-500 Hz, preferably 225 Hz. Instruments for filtering digitized signals in this frequency range are ubiquitous and their use is well-known to persons of skill in the art. All pre-processing steps may be performed, for example, with a Krohn-Hite Corporation Model 3944 Multichannel Filter. In one embodiment, a de-noising step is included.

Many sudden accelerations related to impacts, to the extent they are unwanted motion artifacts in any embodiment of the invention, may be removed with a suitable digital filter during post-processing. Preferably, however, and typically, they are removed during pre-processing.

Analyzing the pre-processed signal in the various embodiments of the invention requires careful selection of the wavelet filters that are used to generate the wavelet packets from which the estimates of muscle effort measurements are to be made. As noted above, wavelet packets that have passed through, say, nine levels of decomposition to acquire the packet, although within the scope of the invention in principle, are expected to be too costly to be borne in a field environment for the foreseeable future.

B. Selecting Effective Wavelet Packets

In one embodiment, the invention provides a method of searching wavelet packet space to identify wavelet filters (or combinations of such filters) that transform VMG signals into consistent predictors of muscle effort. The qualifying criteria are derived from evaluations of dynamically contracting muscles in both women and men, young and old. These categories may be expanded and subdivided at will to create a database wherein evaluation data are segregated by, for example, weight, height, age, quintiles of life expectancy, specific indices of physical condition (e.g., body mass index, fitness index, basal metabolic rate, cardiovascular stress test results, etc.). Embodiments of the invention are also applicable to animals (e.g., race-horses, dogs, etc.). Segregation by muscle body, type of closed-chain or open-chain activity, duration of the activity, etc. are also contemplated. The method comprises acquiring load force data (with a dynamometer, for example, or by using free weights) and vibromyographic data from each of a plurality of individuals as described herein, applying various wavelet filters to transform the vibromyographic data into wavelet packets, as described, and determining the correlation coefficients between the resulting wavelet packet amplitudes (i.e., the instantaneous amplitudes of the envelope of the wavelet packet) and the load force generated in each case. The Wavelet Toolbox™ software available from MATLAB®, for example, provides the graphical tools and command-line functions needed for developing wavelet-based algorithms for the analysis of vibromyographic data, along with the ability to perform regression analysis, as required in practicing embodiments of the present invention. FIG. 6 illustrates the results of one such set of experiments, presented here by way of example and not of limitation. Each wavelet packet is identified by the center frequency of the power spectrum of the signal sub-band to which the wavelet packet applies. In this example, Daubechies Maximum Flat or "extremal phase" mother wavelets of order 1-16 were used, but others may be tested according to the method and thus are within the scope of various embodiments of the invention. The VMG signals were sampled at 5 kHz. It will be understood that any time-frequency analysis which processes, in real-time, a vibromyographic signal acquired from a muscle during a concentric, eccentric, or isometric contraction of that muscle, such that an effort-generation profile for that contraction is derived from the processed signal, is within the scope of the invention. Because of the preference to analyze muscle activities during functional activities (i.e. activities that produce statistically non-stationary VMG signals), however, wavelet packet analysis is most preferred. The criteria for qualifying a wavelet packet for use in embodiments of the invention are:

1. Regression Coefficients.

Figure 20:
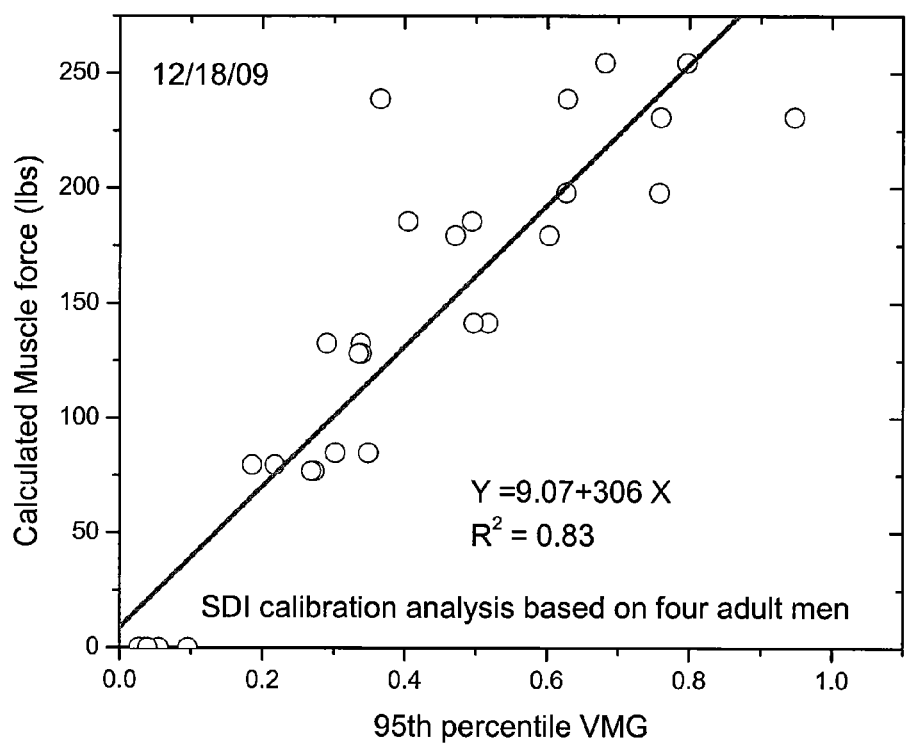
FIG. 20. Calibration data obtained from SDI model 1221L-002 (+/−2 g) accelerometer. Calibration based on the 95$^{th}$ percentile levels (i.e., two standards deviations above the mean) for analyzed outputs associated with loads of −zero to 22.5 lbs.

The regression coefficient between a measured load force and the magnitude (at any instant in time) of the envelope of the calculated analytic function associated with a VMG signal is obtained by single variate or multivariate regression analysis (linear or non-linear) as is conventional in the art. This coefficient provides a calibration, or scaling, factor which can be used to convert the wavelet packet amplitude (i.e., the amplitude of the envelope of the VMG signal that is extracted from a raw VMG signal by means of wavelet analysis) to a measure of force. FIG. 20 provides a specific example. Here, a unitless number (i.e., x-axis value) represents the effort that a contracting muscle produces as reflected through a wavelet packet analyzed VMG signal, but the number may be understood in more familiar terms by multiplying by 306 lbs to obtain the values on the y-axis which are in terms of force units (lbs). The converted expression is also more useful for making comparisons between individuals.

2. Frequency Content.

Wavelet packets having center frequencies in the 40-150 Hz range are useful in various embodiments of the invention. The 60-100 Hz range is preferred and the 70-90 Hz range is most preferred.

3. Sampling Rate.

The wavelet packets that can be generated from a given digitized signal depend on the rate at which the signal is sampled (the more decompositions, the more data are needed). Of those generated, the packets that measure muscle effort most effectively in a given case are ascertained by correlation analysis as noted above. In the present examples, for VMG data sampled at 5 KHz, the best performing wavelet packets were found to be 6.3, 7.4 and 8.8 (implying a relatively large number of decompositions), all with transfer functions centered between 70 and 90 Hz. Note that when using Daubechies mother wavelets, orders (not to be confused with "levels" of decomposition) less than 8 provide better correlations than higher order mother wavelets. For VMG data sampled at 500 Hz, which is advantageous in the development of a multichannel device to be used in real-time applications, the best correlations with force are found to be wavelet packets 2.2, 3.3, 4.4 and 4.5, that is, packets generated with a small number of decompositions ("x") and associated with sub-bands ("y") having center frequencies (70-100 Hz) which are at the higher end of the muscle vibrational frequency spectrum, in contradistinction to what is taught in the prior art.

C. Wavelet Transformation of VMG Signals for Wavelet Packet Analysis

Artisans will recognize that different muscle bodies contract with different characteristic frequencies. Thus, voluntary muscles populated with a preponderance of fast twitch fibers (often referred to as "Type IIb") have at least some frequency content >150 Hz, whereas involuntary muscle (Type I and IIa) contractions are generally below 40 Hz. For such muscles, a cutoff as low as 60 Hz or lower may be preferred. Referring again to FIG. 22, the digital, low-pass filtered signal may advantageously be down-sampled (230) (i.e. the sample resolution can be reduced) to enhance the speed of the wavelet packet analysis. An exemplary but non-limiting sampling rate for wavelet packet analysis is 500 Hz. The artisan may adjust this rate to optimize the relationship between precision and speed. For convenience, the analytical method is described in the context of a specific but non-limiting example below and summarized in FIG. 22. As noted, one embodiment of the invention comprises a method of scanning wavelet packet space to select an optimal packet or combination of packets for use in any particular circumstance, so the selection of the particular wavelet packet in the following example is not intended to be limiting. In this example, a $3^{rd}$ order Daubechies wavelet filterbank is arranged to generate a wavelet packet 4.4 representation of muscle effort. The VMG signal 235 is subjected (240) to four levels of decomposition in the filter bank. When applied to a VMG signal sampled at 500 Hz, a transformed signal sampled at 31.25 Hz is obtained. This follows from the dyadic decimation inherent in the process: After one decomposition, a 250 Hz sample remains; after two, a 125 Hz sample remains; after three, a 62.5 Hz sample, and after four, a 31.25 Hz sample. After the decomposition, (utilizing, in this case, maximally flat FIR filtering for convenience, without wishing to imply thereby any limitation, inasmuch as persons having skill in the art will recognize that many other filter designs may be employed as well), the envelope of the wavelet packet representation of the VMG data is determined. One means to determine the envelope of the VMG signal following WPA is to obtain the analytic function of the wavelet packet representation. This can be accomplished by computing the Hilbert transform of the wavelet packet data (245). In essence, two wavelet packets result, the original and another 90° out of phase with the original. This so-called "analytic signal" generally has positive and negative values. It is advantageous to eliminate negative values. This is conveniently achieved by finding the absolute value by using the square root of the sum of squares (250). At this point, low pass filtering (255) will reveal the envelope of the signal. The envelope amounts to a time-plot that represents generated muscle effort (265). While the above technique provides a substantial improvement in performance (more rapid response time with less phase shift) than simply averaging the accelerometer signal by the root mean square (RMS) technique (which is typically used in the field of VMG/MMG analysis), it is not intended to exclude other mathematical demodulation techniques.

Next, the envelope data may be converted to effort data in force units by multiplying envelope values by a calibration factor obtained empirically. In a preferred embodiment, muscle force relations are acquired under controlled conditions by gathering joint kinematics data in combination with load or torque measurements. In preferred embodiments, a dynamometer is used to measure torque, though free weights can be utilized for this step. While any joint can be utilized to obtain this calibration factor, simple geometries such as those that exist for the triceps insertion onto the ulna are the most direct. However, more complicated insertions, such as the vastus lateralis onto the tibia can be used provided joint mechanics are taken into account. Essentially, one must treat the limb of interest and its joints as a lever system that supports, lifts or otherwise moves a load and determine from the system's geometry the forces generated by the system. The values obtained are then correlated with the VMG envelope amplitude data (265) so that the latter can be expressed in terms of an effort in units of force (e.g., pounds-force). When this technique is applied in the specific example set forth above (i.e. for the triceps muscle controlling elbow extension utilizing the SDI 1221L-002 accelerometer with a gain of 20× and a 16 bit A/D convertor with a input range of ±1V), a calibration factor of approximately 300 is obtained (c.f., FIG. 20).

Although the envelope-force relation for each musculoskeletal system (e.g. ankle, knee, elbow, shoulder, etc) is expected to be different to a degree, average values may be acquired empirically for each system in the database contemplated hereinabove. It is within the scope of the invention to establish and use a single calibration or conversion factor in all assessments of muscle effort made according to embodiments of the invention. The artisan will appreciate, however, that a set of calibration factors may enhance the accuracy, precision and discriminatory power of the methods. Preferably, the practitioner will employ embodiments of the present invention to establish a different conversion factor for each muscle body type (I, IIa, IIb) and each anatomic arrangement of muscle (spindle, pennate, bipennate) and skeletal elements. The artisan will also readily appreciate that the conversion factor(s) will change whenever the accelerometer or method of processing the signal changes. Also, the artisan will readily appreciate that, once scaled to muscle effort, a threshold effort value (for example, 10 units in pound-force) may be established to delineate "functional activities" from non-functional activities.

Certain events which exceed the threshold and therefore may be considered to be "functional activities" may, in fact, be a result of "impact spikes" as described above. Impact spikes can be identified by their very short duration and their occurrence near the beginning of a muscle contractile event. While functional activities typically span at least 200 milliseconds in time, impact spikes are transient, and usually last less than 200 milliseconds, typically under 100 milliseconds, and often less than 50 milliseconds. Temporal filtering may therefore be used to exclude impact spikes from further analysis, by eliminating any "event" (i.e. where apparent muscle effort exceeds a predetermined threshold) of duration less than about 100-200 milliseconds, particularly those occurring near the initiation of a contractile event.

D. Apparatus

In some embodiments, the invention provides a muscle effort analyzer comprising the following hardware and software as schematically represented in FIG. 24:

1. At least one accelerometer (500), preferably realized as a microelectro-mechanical device having a working range of 2-50 g (where g=9.8 m/s$^2$; a bandwidth of 0-1 KHz; a sensitivity of 0.01-10 V/g, and a noise density of 1-100 µg/Hz$^{1/2}$. An SDI Model 1221L-002 MEMS accelerometer is currently most preferred.

2. A means (505) of compressing the accelerometer against the muscle body as well as minimizing changes in the accelerometer's position with respect to the muscle body during movements of a body part. In one embodiment, the invention provides a sheet of elasticized material, preferably a material having an elastic modulus along a strain axis of more than about 25% to 100%. Preferably, also, the sheet is sufficiently long under a strained condition to permit at least one full wrap around the limb or body segment under investigation, and sufficiently wide to keep the accelerometer against the muscle body. In preferred embodiments, the material stretches to more than about 150% of its resting length, and returns to approximately its original length when relieved of strain. In one embodiment, the accelerometer is placed between the elastic material and the skin. In an alternate embodiment, the accelerometer is affixed to one of the surfaces of the material. In another embodiment, the accelerometer is embedded in the material. Any suitable means of securing the wrap, including friction, adhesives, mechanical fasteners, hook and loop fasteners, etc., is within the scope of the invention.

3. A means (507) of sending the output of the accelerometer to the input port of a filter (510) for removing motion artifacts from the output signal. Preferably, the filter is a part of the sensor package. Alternative embodiments include wireless, wire cable, fiberoptic cable, etc. to convey the signal to the filter. Preferably, the output of the accelerometer is an analog signal and the filter accepts an analog input. Not excluded, however, are other compatible combinations such as a digital output sent to a digital filter or an analog signal that is converted to a digital signal before being sent to a digital filter.

4. The aforementioned filter (510) is preferably a high pass filter that tends to remove the high energy components of the VMG signal at frequencies less than 30 Hz (20-50 Hz).

5. A means (515) for amplifying the output of the high pass filter by a factor conditioned upon the capacity and sensitivity of the accelerometer and sufficient to utilize the full range of a 16 bit A/D converter (typically 10-100 fold). Preferably, the amplifier means is also a part of the sensor package. Thus, a preferred sensor package comprises the aforementioned accelerometer, filter and amplifier, in communication with one another wirelessly, electrically or optically, and an interface to permit wireless, electrical or optical communication of the sensor package with additional signal processing apparatus, as enumerated in 6-10 below.

6. A means (520) of preventing "misreading" of signals of signals during digitization and sampling ("aliasing"). In a preferred embodiment, at this sampling rate, a low pass filter 250 Hz to 2 KHz (preferably 360 Hz) is used. In general, prior to any sampling step, a low pass filter having a cutoff frequency between $1/16$ and $1/2$ of the sampling rate is preferred.

7. A means (525) for converting an analog signal to a digital signal at 16 bit resolution (though 12-24 bit resolution may be required for certain applications).

8. A means (530) for removing from the digital signal frequencies higher than about 60 Hz, preferably higher than about 100 Hz, and most preferably higher than about 225 Hz.

9. A means (535) of reducing the frequency of sampling ("down-sampling") to permit more rapid wavelet packet decompositions. Any amount of down-sampling is within the scope of the invention provided only that the number of samples retained is sufficiently low to meet the real-time criterion for embodiments of the invention and sufficiently high to permit a correlation between the processed VMG data and the muscle force data greater than about 0.3.

10. A computer (565) programmed to perform steps 240, 245, 250 and 255 as outlined in FIG. 22. The computer may be physically present or remotely situated. Preferably, however, feedback from the computations is available in real-time.

E. Kits

In a highly preferred embodiment, the invention provides a kit for assessing muscle effort, the kit comprising:
a. a means (505) of compressing an accelerometer against a muscle body as well as minimizing changes in the accelerometer's position with respect to the muscle body during movements of a body part;
b. a vibromyographic sensor comprising:
i. at least one accelerometer (500), preferably realized as a microelectro-mechanical device having a working range of 2-50 g (where g=9.8 m/s$^2$; a bandwidth of 0-1 KHz; a sensitivity of 0.01-10 V/g, and a noise density of 1-100 µg/Hz$^{1/2}$;
ii. a means (507) of sending the output of the accelerometer to the input port of a filter (510) for removing motion artifacts from the output signal. Preferably, the filter is a part of the sensor package. Alternative embodiments include wireless, wire cable, fiberoptic cable, etc. to convey the signal to the filter. Preferably, the output of the accelerometer is an analog signal and the filter accepts an analog input. Not excluded, however, are other compatible combinations such as a digital output sent to a digital filter or an analog signal that is converted to a digital signal before being sent to a digital filter;
iii. a filter (510), a high pass filter that tends to remove the high energy components of the VMG signal at frequencies less than 30 Hz (20-50 Hz). Preferably the filter is a part of the sensor package, and
iv. a means (515) for amplifying the output of the high pass filter by a factor conditioned upon the capacity and sensitivity of the accelerometer and sufficient to utilize the full range of a 16 bit A/D converter (typically 10-100 fold). Preferably, the amplifier means is also a part of the sensor package;
c. a software program to perform steps 240, 245, 250, 255 and 260 as outlined in FIG. 22, wherein said program is embodied in a machine-readable medium for use on a computer (565), and
d. instructions for the use of the sensor and the software.

E. Assessing Muscle Strength and Coordination

1. Single Muscle.

In one embodiment, the invention provides a method for measuring, directly from VMG recordings and in absolute units, the effort that a muscle of an individual can generate from moment to moment in a variety of circumstances. That is, specific sub-components of the VMG track changing muscle effort during limb motion.

Figure 8:
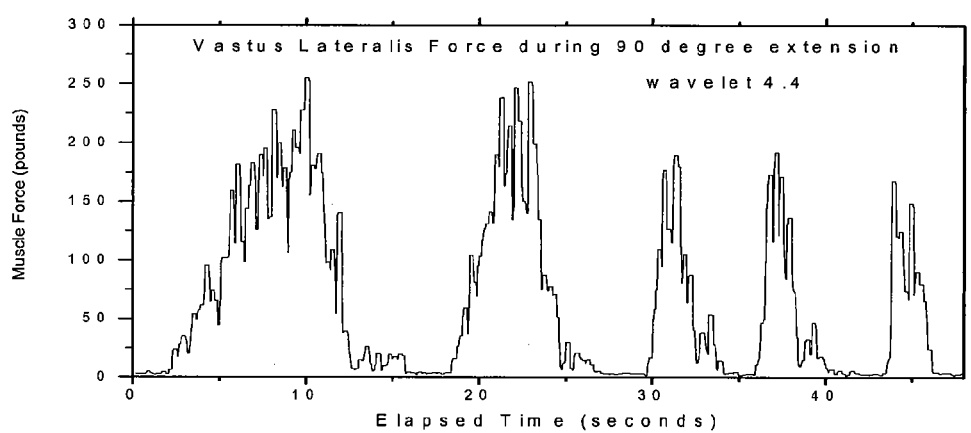
FIG. 8. Ability of VMG to track vastus lateralis muscle effort during a simulated "standing up" activity, using best wavelet packet identified by wavelet packet space screening (i.e. Daubechies order 3; packet 4.4). Sequence runs from slow, 10 second extension, to a rapid two second extension.

In one non-limiting example, VMG recordings were made from the vastus lateralis (VL) muscle during a series of 90 degree extensions of the knee against a 100 ft-lb torque, an exercise approximately equivalent to the act of standing from a seated position. FIG. 8 illustrates muscle effort generation in each of a series of extensions from quite slow (extending over approximately 10 seconds) to quite rapid (extension completed in less than two seconds). The ability of the VMG to track the increasing effort of the VL as the knee straightens is clearly evident.

Note that VMG recordings obtained in this manner have the capability of measuring muscle effort associated with both concentric and eccentric contractions and, as well, the effort generated during both open chain and closed chain exercises. Note also that when recording VMG data during exercises wherein the subject is jumping, or otherwise experiencing g forces higher than 2 g, accelerometers with a working range greater than 2 g (e.g., 5 g or 10 g) can readily replace the 2 g sensor described above, with suitable adjustments made for the scaling parameters. However, accelerometers with noise densities less than 50 µg/√Hz and size less than 4 cm$^2$ are preferred.

While the data above illustrates measurements from the vastus lateralis, which is a critical muscle in the context of the etiology of numerous knee injuries (e.g. anterior-cruciate ligament tears; patella-femoral syndrome, etc), the technology can be readily applied without modification, other than the means of attaching an accelerometer, to the evaluation of an assortment of muscles which are near the skin surface and sufficiently large to permit recording using an accelerometer with dimensions of 4 cm$^2$ or less. These muscles would include other large muscles around the thigh (e.g. vastus medialis; rectus femoris; biceps femoris, etc); muscles involved in ankle flexion and extension; muscles involved in elbow flexion and extension; muscles involved in wrist flexion and extension; muscles involved in shoulder rotation; muscles involved in the flexion and extension of the back; muscles involved in the flexion and extension of the neck; muscles involved with abdominal contraction and other obvious extensions of the technology which meet the requirement established above.

2. Ability of VMG to Identify Peak Effort (Muscle Strength) and Time to Peak Effort During Rapid Motion.

Figure 9:
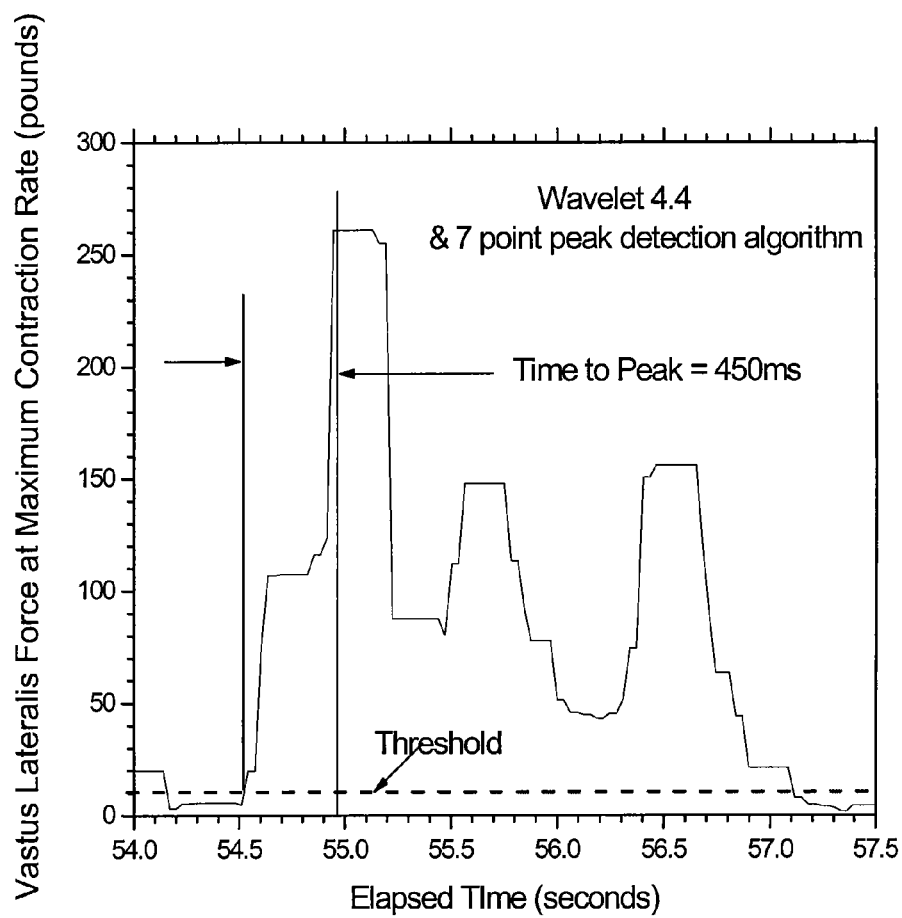
FIG. 9. Identification of Peak Muscle effort during "bursting" exercise, and time to peak force.

An important assessment for both PTs and trainers is the bursting power (often called explosive power) that an individual can generate. The ability to assess bursting power requires the ability to identify peak effort and time to peak effort. The ability of VMG to track such a burst of power, when analyzed as described above, is illustrated in FIG. 9 where the effort of the VL during a very rapid concentric (such as jumping) and eccentric (such as landing) contraction is seen. The time to peak muscle effort is seen to be approximately 450 ms in this instance, though the ability of VMG to identify even more rapid contraction times is evident (the time resolution of the analyzed VMG signal is on the order of tens of milliseconds).

Figure 10:
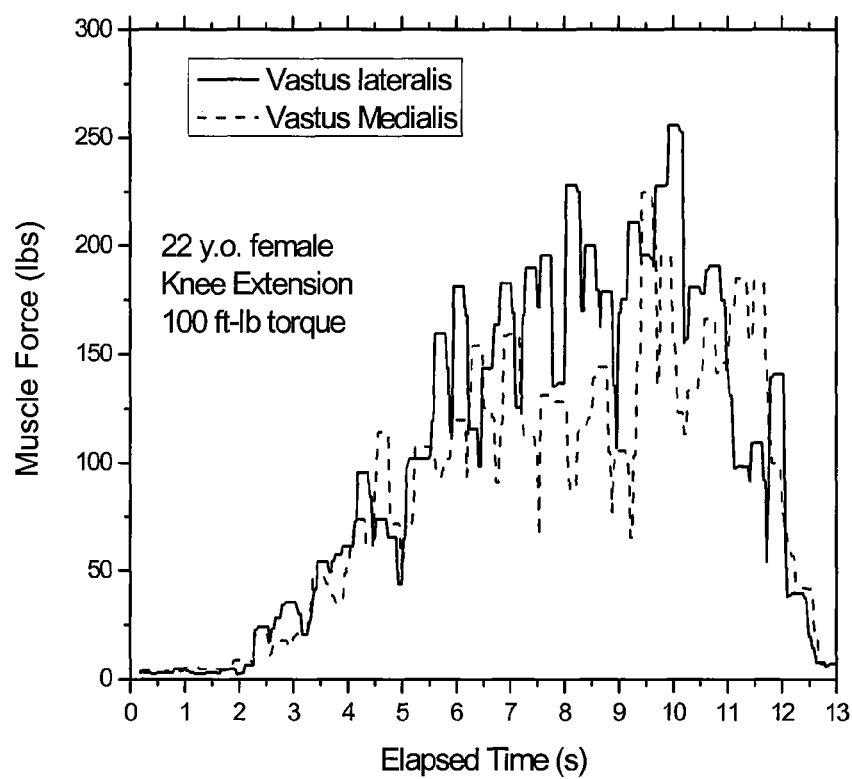
FIG. 10. Use of VMG to obtain simultaneous recording of vastus lateralis and vastus medialis muscle effort during a 90 degree knee extension representing standing from a seated position.
Figure 11:
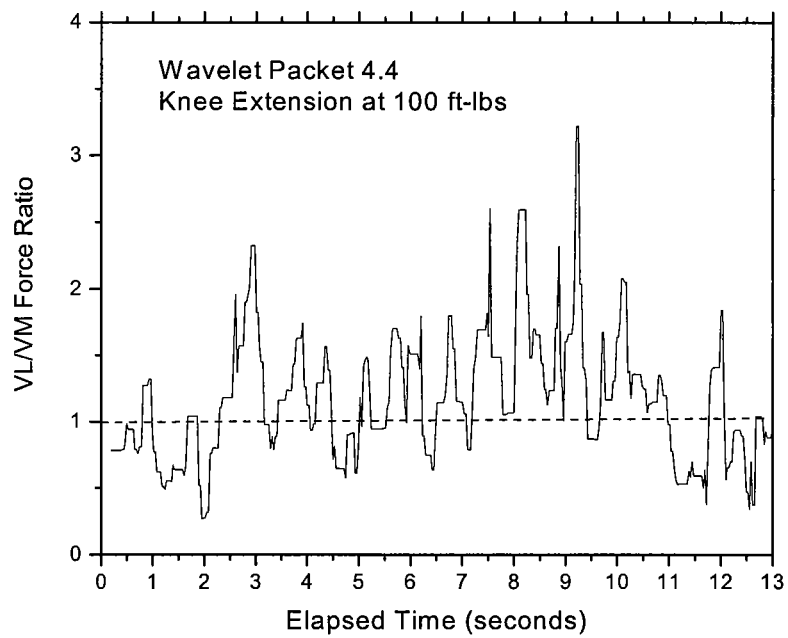
FIG. 11. Ratio of vastus lateralis effort to vastus medialis effort (FIG. 10) in a young female athlete during knee extension. Note that the activity of the muscle pair is largely balanced through full extension (ratio near 1) though a maximum ratio of approximately 3 is observed near the end of extension. Where the VL effort reaches maximum (at approximately the 10.5 second time point), the VL/VM ratio exceeds 2, indicative of an over-trained VL muscle in this individual.

3. Use of multiple real-time VMG assessments. In especially advantageous embodiments of the invention, one may obtain muscle effort ratios in healthy subjects. In preferred embodiments, a plurality of accelerometers and pre-processing filters are used simultaneously to acquire data conjointly from paired muscles. The ability to obtain real-time muscle effort assessments sets the stage for a wide range of diagnostic and evaluative procedures involving two or more muscles, as both normal activities of daily living, as well as sporting activities, rely extensively on the precise timing of the activation of, and the effort generated by, muscle pairs. This includes contralateral pairs (i.e. pairs across the body; e.g. the left and right vastus lateralis which are used to stand); supplemental (or synergistic) pairs (such as the vastus lateralis and vastus medialis in the leg, which both contribute to knee extension); antagonistic pairs (such as quadriceps and hamstrings which permit standing and walking), as well as complementary pairs (such as back and arm muscles used to lift). Importantly, muscle pair imbalances are the usual cause of muscle and joint injury. The simultaneous recording from such pairs of muscles can therefore be used to evaluate whether muscle timing and/or whether muscle force ratios are abnormal. An example of utilizing VMG to obtain real-time muscle effort data in a supplemental muscle pair (VL and VM) is shown in FIG. 10. The ratio data associated with the data shown in FIG. 10 is presented in FIG. 11.

F. Applications in Diagnostics

The VL/VM ratio is of considerable value in assessing the cause of patella-femoral syndrome. An over-trained VL is commonly the cause of this condition. In a similar manner, the right and left VL may be compared to identify right/left imbalances in leg strength (and this is commonly done in the initial stages of knee rehabilitation). Alternatively, the VL effort during an exercise may be compared to the biceps femoris (BF) effort. High quadriceps (VL) effort during rapid starts and stops, relative to BF (hamstring) forces, are a predominant cause of anterior cruciate ligament injuries.

Figure 12:
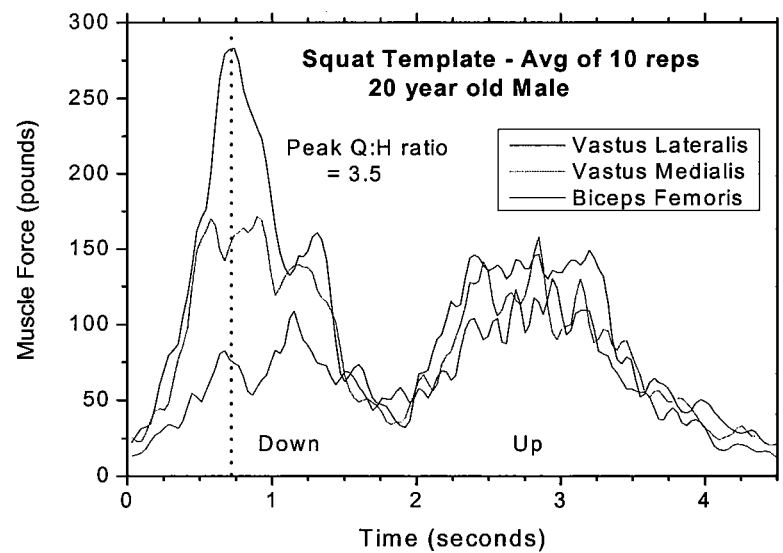
FIG. 12. Muscle effort template for young (20 y.o.) healthy, non-athlete, male. Template obtained from 10 repetitions of the fundamental motion commonly referred to as a "deep squat." VMG recordings from the vastus lateralis (VL), vastus medialis (VM) and biceps femoris (BF) were obtained throughout the 10 repetitions after which the squat events were synchronized in time and averaged.
Figure 13A:
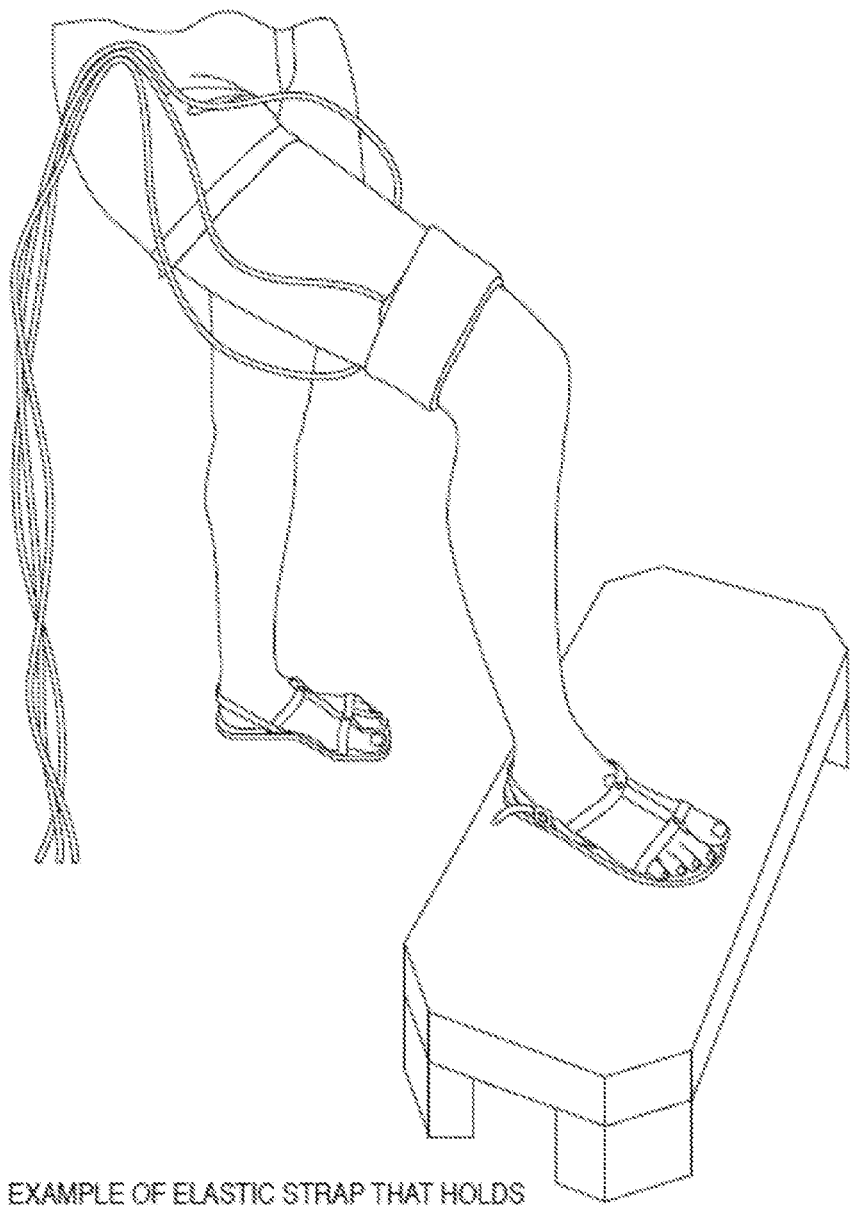
FIG. 13. Illustration of VMG recording apparatus for evaluation of the extensor and flexor muscles of the knee.
Figure 13B:
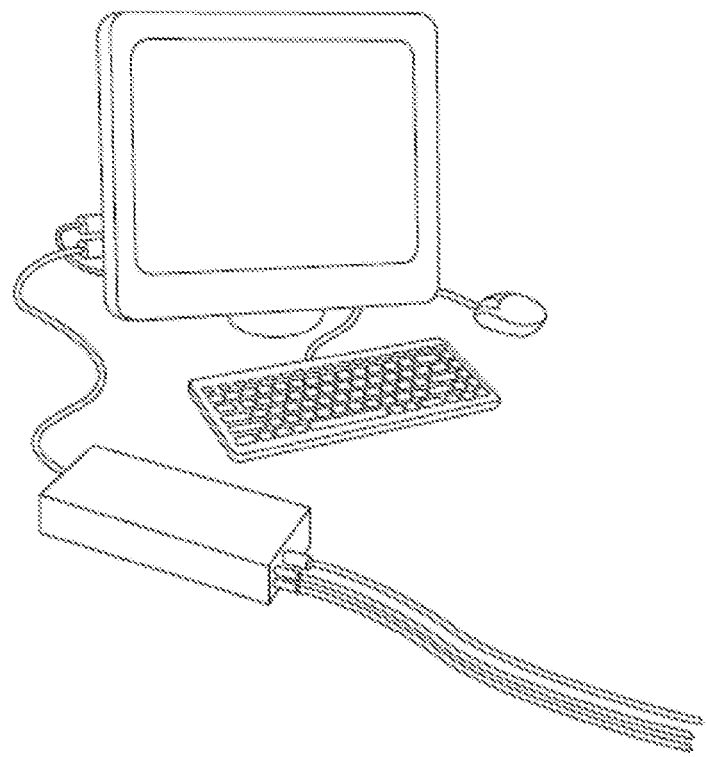
Figure 14:
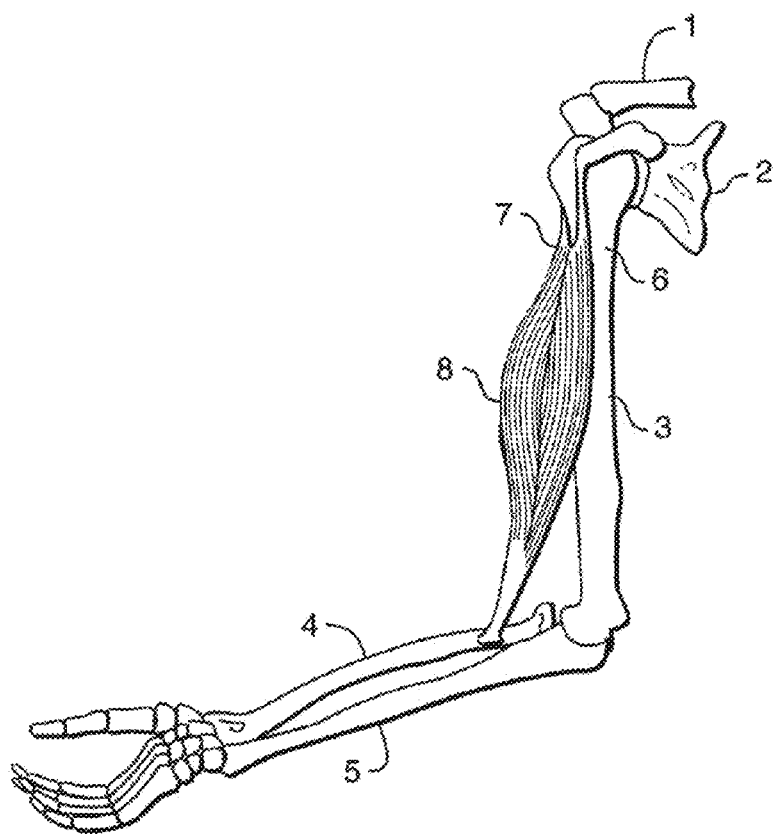
FIG. 14. Optimal VMG wavelet packets can be isolated using a supported load as a reference point. For example, in the evaluation of the lifting capacity of the biceps brachii, the load being supported by the hand provides a useful reference value. However, this load does not reflect the effort being generated by the muscle. The latter can be obtained by consideration of the geometry of the anatomy of the arm. If the load supported is multiplied by the ratio of the length of the arm (elbow to wrist) to the distance from the elbow to biceps insertion point on the forearm, an accurate estimate of muscle effort results. The estimate can then be utilized to calibrate the VMG data obtained during muscle effort as a function of time, to provide an expression of the data in familiar terms.

Over the last few decades, a consensus has formed among PT and trainers with respect to certain muscle pair ratios. For example, in healthy individuals, muscle strength on the left and right sides of the body are expected to be closely balanced (~1:1 ratio); lateralis:medialis ratios should not normally exceed 1.5:1; and Quad:Hamstring ratios are expected to be maintained below 3:1 during dynamic activity. These ratios can be substantially different in both the trained athlete (for example Quad/Hamstring ratios may exceed 10:1 in an elite athlete) and in the post-surgery or post-injured individual, where muscle weakness can be substantial. Further, it is important to note that the preferred assessment is based not simply on the peak effort being generated by the muscle group (i.e., muscle strength), but the dynamics involved in muscle force creation (i.e. muscle effort). FIG. 12 illustrates how a "standard" can be constructed which can be used by clinicians or trainers to diagnose muscle imbalance problems. Muscle effort templates can be constructed for a particular class of people, e.g., male, female, young, old, athletic, non-athlete (see FIG. 12 for young healthy non-athlete males). Lower body human motion is composed of a set of five fundamental motions (step, squat, lunge, leg raise and seated rotation). By recording muscle effort from individuals from the group of interest repeatedly performing one of the fundamental motions, a template can be constructed which can serve as a reference for clinicians and trainers. FIG. 12 illustrates a muscle effort template for three main knee flexor and extensor muscles. The relative effort generated by these three muscles, and the timing of contraction, are clearly evident in the average recording of 10 repetitions. Averaging of a greater number of repetitions would correspondingly result in a more smooth appearance to the template.

It is seen in this representative template that though both muscles of the quadriceps (VL and VM) activate at approximately the same time, the VL in young men tends to contribute twice the effort to the extension of the knee when squatting down (i.e. during eccentric contraction of the quadriceps), than the VM. Moreover, at the time of peak effort generation by the VL, the hamstrings (biceps femoris—which are in concentric contraction) are generating less the ⅓ the effort of the VL. It is also evident that the quadriceps develop effort much more quickly than the hamstrings. When rising from a squat, the VL is still the dominant muscle, but the effort of the three muscles is much more closely balanced. Recordings from young healthy non-athletic males can be obtained and compared to such a template to assist in the diagnosis of muscle imbalance during any of the fundamental human motions. This type of assessment cannot be obtained with either SEMG or dynamometer measurements. It is a unique feature of real-time VMG assessment, specifically as described herein.

TABLE 1

Muscle Pairs and Pathologies Related to Pair-Imbalance

| Anatomic Relationship | Muscle Pair | Pathology |
|---|---|---|
| Contralateral | Right and Left Vastus Lateralis | Knee injury |
| Contralateral | Paraspinal muscles | Scoliosis, chronic back pain |
| Supplemental/Synergists | Vastus lateralis and vastus medialis | Patello-femoral pain syndrome |
| Supplemental/Synergists | Biceps brachii and brachialis | Tennis elbow |
| Complementary | lower trapezius and serratus anterior/rotator cuff | glenohumeral joint pain and dysfunction |
| Complementary | Erector spinae and gluteus maximus | Lower back pain |
| Antagonistic | Quadriceps/Hamstrings | Anterior cruciate ligament injury |
| Antagonistic | Biceps/Triceps | Tennis elbow |

TABLE 1-continued

Muscle Pairs and Pathologies Related to Pair-Imbalance

| Anatomic Relationship | Muscle Pair | Pathology |
|---|---|---|
| Antagonistic | the hamstrings, adductors, hip flexors and abdominal recti/transversus abdorninis and posterior glutei mediae | sports hernia, osteitis pubis, chronic adductor tendinosis |
| Antagonistic | Digit flexors/extensors | Carpel tunnel syndrome |
| Antagonistic | Gastrocnemius, tibialis anterior | Tibial stress fractures, Achilles tendinosis, shin splints, compartment syndrome |

Most musculo-skeletal injuries are associated with one of these major types of muscle imbalances and so, correspondingly, there are a large number of muscle imbalances which could be identified using real-time VMG assessment.

G. Applications in Physical Therapy

Knee injuries and knee rehabilitation are remarkably common in most western countries. In the U.S., for example, over 2M knee injuries are treated each year. As most knee injuries are associated with muscle imbalances, this condition is an important application area for real-time VMG based muscle balance assessment. Therapeutically, treatment of the injury is directed at restoring appropriate balance in the muscles that contribute to stability of the joint. The ability to monitor those balances and changes in them over the course of treatment is an embodiment of the present invention. Moreover, the application of muscle effort ratio assessment to the rehabilitation or training of individuals can readily be extended to other important joints where injury is common or where performance is critically linked to the muscle pairs operating around the joint.

Important but non-limiting application areas include the elbow (e.g. tennis elbow has a prevalence of over 10% among 40-50 year olds); the shoulder (over 15M Americans each year are treated for tennis shoulder; swimmer's shoulder; rotator cuff injuries, etc.); the lower back (back pain is usually the result of imbalances in abdominal and back musculature, and afflicts close to 50% of all adult men); the neck (muscle imbalances of the neck are a common cause of migraine headaches), and the ankle (approximately 1M ankle injuries, the majority sprains, occur each year due to lower leg muscle imbalances).

Modern mechanomyography (MMG) recording techniques of muscle contraction have been under investigation since the 1970's [1], [2]. MMG data is multi-factorial, detecting the radial motion of a muscle body due to the intrinsic expansion of muscle fibers during contraction, gross muscle movement at the onset and cessation of contraction, oscillations of the muscle at its resonant frequency, and potentially, movement or oscillation of the limb. While position and velocity sensors have been widely used in this research, the accelerometer has been found to be one of the most reliable transducers for measuring muscle motion during contraction [2]. We utilize accelerometer recordings in our analyses, and therefore refer to the technique as vibromyography, or VMG. However, lack of a monotonic relationship between VMG amplitude and muscle force has precluded widespread adoption of this technology. Although under certain conditions, twitches from individual motor units can be resolved in VMG recordings [3], [4], [5], VMG:force relationships typically degenerate beyond 60-70% of Maximum Voluntary Contraction (MVC). This may be due to the non-linear twitch summation of the VMG signal beyond motor unit firing frequencies of about 20 Hz [3], [6], or it may be due to the biomechanical complexities in the study of pinnate muscles [7].

Investigators addressing the relationship between VMG recording and joint flexion force have processed their VMG data using techniques similar to those developed to evaluate electromyographic (EMG) data. Commonly, the RMS value of the recorded data is correlated to force [7], [8], [9]. Almost as commonly, investigators have applied Fourier analysis techniques in attempts to improve the performance of the VMG [4], [7]. These approaches have brought mixed success, likely due to the inherent non-stationarity of VMG recordings, suggesting that time-frequency analysis may prove a more effective strategy for information extraction.

The recently developed Wavelet Packet Analysis (WPA) has been shown to have superior performance to several Fourier-based techniques for de-noising and information extraction from single channel EMG signals [2] via thresholding, cumulative energy and shrinkage techniques [10], [11]. Investigators have also applied WPA to MMG recordings in order to determine whether improved performance could be obtained (Beck, et al 2009). However, these investigators focused on the low frequency, high energy wavelet packet modulations. The wavelet packet analyses undertaken by the applicants have revealed that the most relevant information in VMG recordings lies at higher frequencies where, in general, lower energies are found. Indeed, WPA of VMG signals in this region identifies the specific components of the VMG that permit real-time assessment of absolute muscle force so as to 1) provide a measure of absolute muscle effort over the full range of voluntary contraction levels; 2) provide sufficient time resolution to permit characterization of rapid voluntary motion (less than 200 ms); 3) permit assessment during open and closed chain events; 4) permit effort comparisons between individual muscles within an individual; 5) permit effort comparisons on a muscle over time (days, weeks, or months), and 6) permit muscle effort comparisons between individuals.

EXPERIMENTAL

The following examples serve to serve to illustrate certain exemplary embodiments and aspects of the present invention and are not to be construed as limiting the scope thereof.

Example 1

Wavelet Packet Analysis of VMG During Isometric Contraction

Muscle fibers in uni-pinnate muscle are not aligned with the direction of pull, and in bi-pinnate muscles the relationship between fiber motion and net muscle force may be even more complex. To eliminate this confounder, one may record from the brachioradialis, a non-pinnate muscle of the forearm muscle which is readily accessible to VMG recording, and relatively powerful, so that a wide force range can be studied. The biceps brachii and the brachioradialis are synergists for elbow flexion-extension with the brachioradialis acting as a strong elbow flexor when the radioulnar joint is in a mid-position between supination and pronation. When the VMG was recorded from the brachioradialis disposed in this position during stationary dynamic constant external resistance (DCER) contractions from 0 to 100% maximum flexion force (MFF), and the data were subjected to WPA (to separate components of the VMG) and to linear regression (to identify those components most closely related to force production), VMG recordings can provide an accurate non-invasive measurement of absolute muscle force in both men and women.

Subjects and Study Design

Inclusion criteria for this study were healthy adult men and women with no current fractures, bone disease, neuromuscular disease, muscle soreness or systemic illness and the capability of following the experimental protocol. After removing jewelry and arm coverings, subjects stood with their backs flat against a vertical wall. The subject's left elbow was positioned near the body and against the wall, elbow at 90°, forearm in mid-position between pronation and supination, with an open, relaxed palm. An accelerometer was affixed to the skin above the belly of the brachioradialis using 2.5 cm wide double-sided adhesive tape (3M Corporation, United Kingdom PLC). For stability, the lead was strain-relieved to the arm with tape and a wide elastic band was placed around the forearm over the accelerometer.

Mechanical loads were suspended from the wrist over the distal end of the radius and ulna, proximal to the styloid processes of the radius and ulna, with a padded 2.5 cm wide nylon strap. Loads were increased from 0% of maximum flexion force (MFF) (defined as only the force of gravity acting on the forearm) to 100% of MFF (the maximum load the subject could hold while maintaining the posture described above for a period of 3 seconds) in 0.4 Kg increments. The load was removed and a 60 second recovery time was provided before the next loading period to reduce the onset of fatigue (at the discretion of the subject). All contractions were nearly stationary during recording, with wrist motion >5 cm in any direction invalidating a lift. Data for each subject was collected during a single recording session.

Data Acquisition and Analysis

Analog VMG data were collected using a Kistler K-beam capacitive accelerometer (Model 8304B2), pre-amplified by a K-Beam 5210 power supply (10× gain). For each recording, approximately 3 seconds of VMG data were digitized using a Biopac MP35 data acquisition unit (Biopac Systems, Inc., Goleta, Calif.) sampling at 5 kHz with a low-pass biquadratic filter at 1.0 kHz (24 bit A/D resolution, DC coupled, 5× gain). Post processing of the digitized data was performed on blinded samples using Mathematica V 5.2 with Wavelet Explorer 1.2.2 (Wolfram Research, Inc., Champaign, Ill.), regressions were performed in SPSS V 10.0 (SPSS, Inc., Chicago, Ill.) and results were confirmed with Origin V 6.1 (OriginLab Corporation, Northampton, Mass.).

VMG data were decomposed using dyadic wavelet packet analysis using the level 10 Daubechies analyzing wavelet with 18 digits of precision. RMS values of individual wavelet packets (crystals) were obtained for each subject after 6, 7, 8, 9 and 10 decompositions. These pooled amplitude estimates were bootstrapped (resample size=13, n=1000) for male and female sub-populations separately and paired with force measurements for their respective lists and each was analyzed with a first-order bivariate regression. Since preliminary analyses identified a quadratic relationship between amplitude estimates and measured force, we performed regressions using the square of measured load force versus amplitude in the final regression models. Only crystals whose center frequency (the frequency to which the WP responds maximally) was located in the physiologically relevant regime (10 to 175 Hz) were entered in the regression models. The coefficient of determination calculated for the regression models was utilized as a metric to compare the predictive power of each crystal.

This non-parametric data de-noising/estimation method is a two step process where step one is non-parametric regression using wavelet packet decomposition following the model of signal plus noise giving, $$y(n,i) = f(n,i) + e(n,i), \quad (1)$$

where $$e(n, i) = \left(\sum_{k=1}^{p} f(n, k)\right) - f(n, i), \quad (2)$$

and $$p = 2^n, \quad (3)$$

where n is the index for the decomposition level, i is the sub-band index in sequence order, $f_{(n,i)}$ is considered the signal of interest, $e_{(n,i)}$ is considered noise. For simplicity, each level (n) was considered separately. Step two quantifies the goodness of fit of amplitude estimates from each bootstrapped $y_{(n,i)}$ in each gender group using the coefficient of determination of a bivariate linear regression between a vector of banded signal amplitude estimates and a vector of the square of the loads lifted by each subject, thus there was no normalization to 100% MFF. This methodology assumes the existence of a component whose amplitude has a straight line relationship with the square of net volitional elbow flexion force (EFF), and as such the results represent a phenomenological model of muscle activity where the component of interest is considered narrow-band and amplitude modulated. However, it is in not intended to imply that VMG data are composed of WP building blocks.

Results

Twenty-three male and thirteen female volunteers were recruited and entered into the study. Males were significantly taller, heavier, and stronger, with higher Body Mass Indices (BMI) (Table II).

TABLE II

Demographic and Summary Data.

| Variable | Males | Females |
| --- | --- | --- |
| Age, yr | 21.67 ± 1.33 | 21.0 ± 0.78 |
| Height, cm | 175.79 ± 1.21 | 160.61 ± 2.08* |

TABLE II-continued

Demographic and Summary Data.

| Variable | Males | Females |
|---|---|---|
| Weight, Kg | 75.96 ± 3.36 | 56.45 ± 1.85* |
| BMI, Kg/m² | 24.48 ± 0.96 | 21.99 ± 0.89* |
| Weight Lifted, Kg | | |
| Maximum | 89.0-311.5 | 75.7-182.5 |
| Average | 190.0 ± 11.7 | 111.6 ± 8.7* |

*indicates a difference between men and women (P < 0.05). Values are means ± SEM.

First order de-trended VMG recordings from each subject exhibited varying, non-monotonic relationships between VMG RMS and force especially beyond 65% MFF (FIG. 1). This behavior was in agreement with the findings of other studies involving similar muscles under voluntary control [12], [13], [14], and [15].

Figure 15:
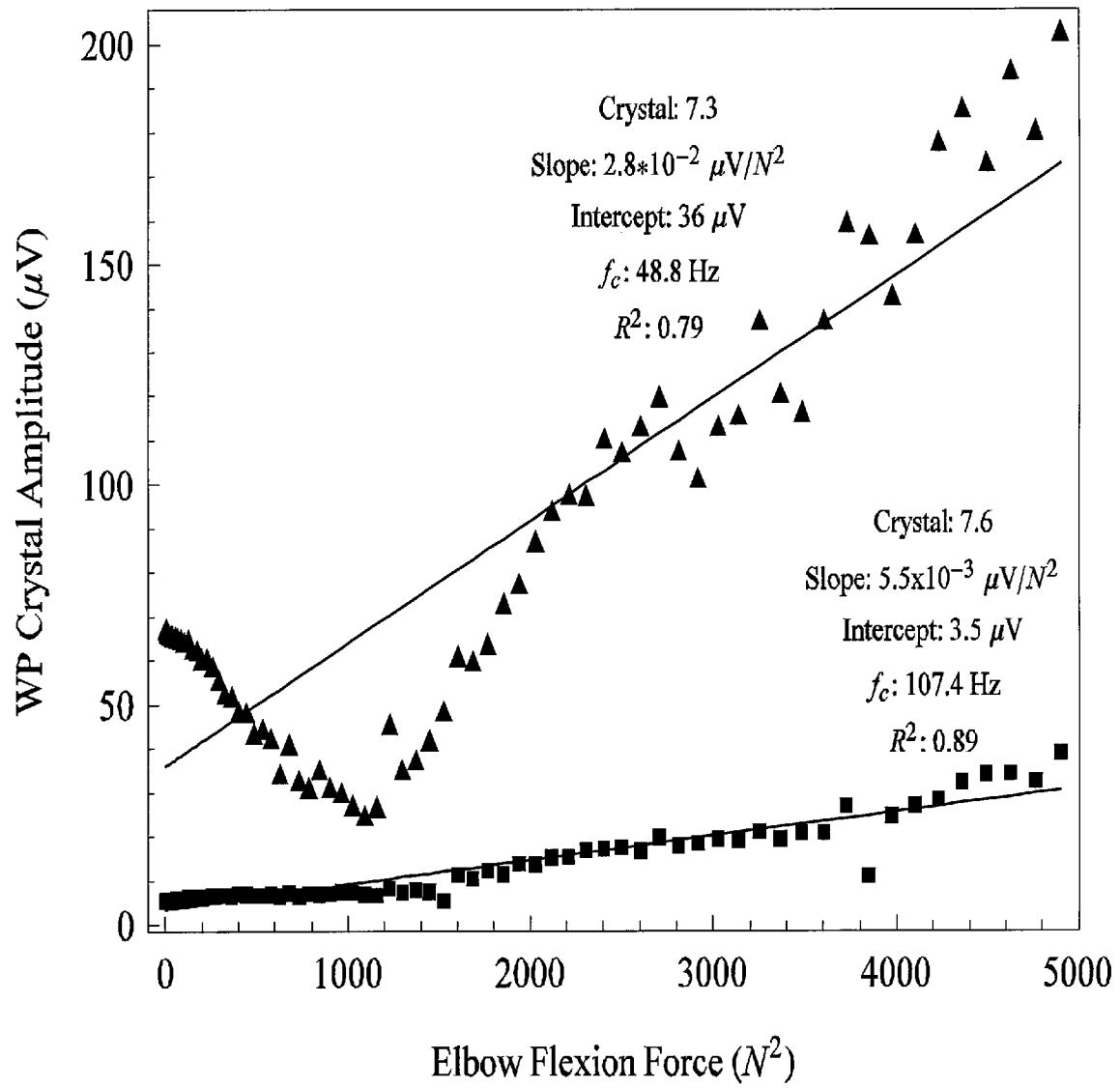
FIG. 15. Linear regression plots of elbow flexion load force squared ($EFF^2$) vs. amplitude of wavelet packet-modulated signal for Packet 7.3 ($f_c$=48.8 Hz) and Packet 7.6 ($f_c$=107.4 Hz). Results shown here are denoted with arrows in FIG. 16($a$), FIG. 17 and FIG. 18.

Relationships between $EFF^2$ and WP crystal amplitude were variable across crystals, even for single individuals. We characterize WP by their center frequency ($f_c$), which is the frequency to which the packet responds maximally. $EFF^2$:WP crystal amplitude relationships were often non-monotonic in character, but we consistently found more dynamic amplitude modulation in lower $f_c$ packets than in high $f_c$ packets, across levels of effort (FIG. 15).

Figure 16:
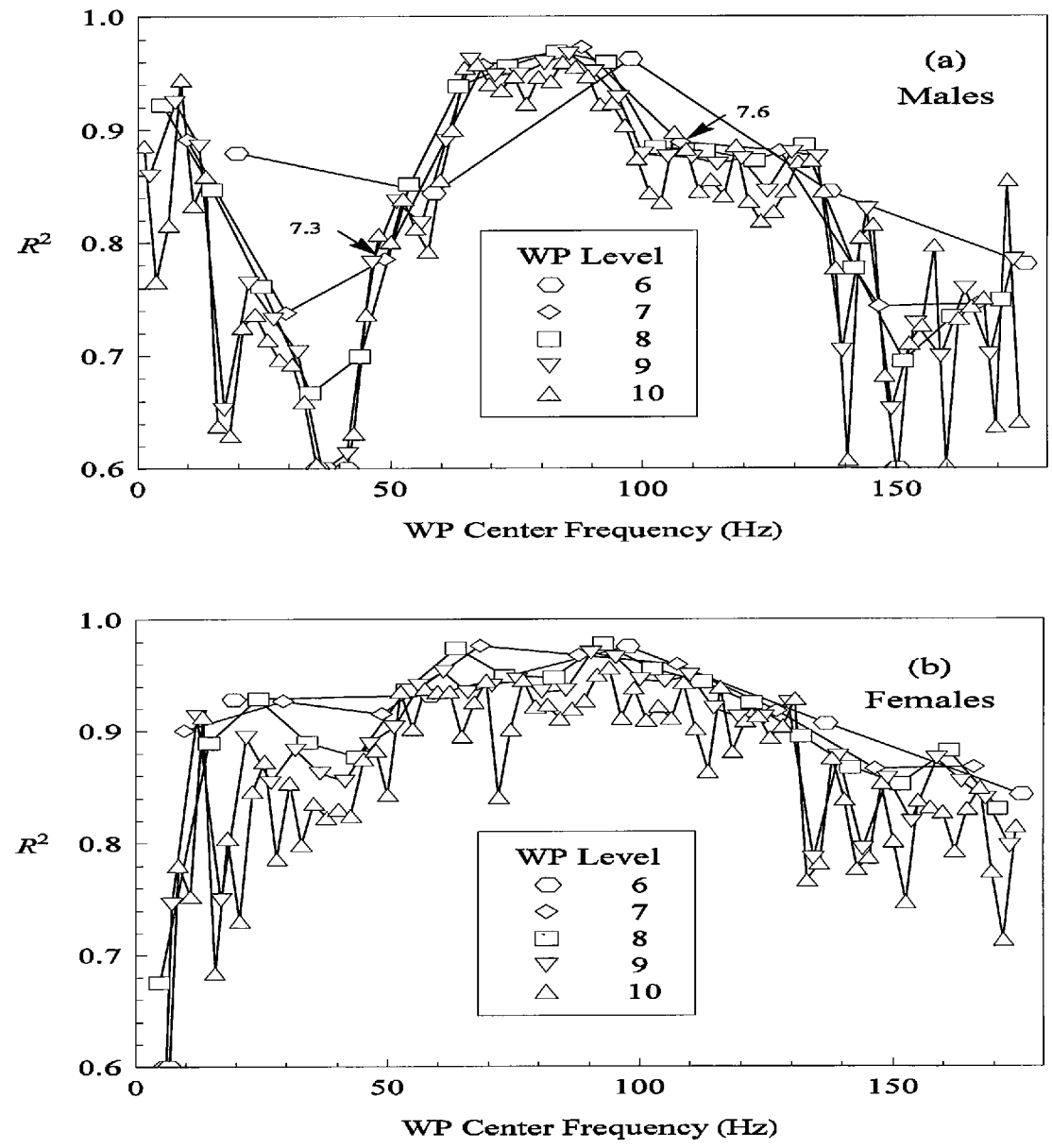
FIG. 16. Predictive power ($R^2$) of single wavelet packets resulting from wavelet decompositions (levels 6-10) of VMG signal.

Surprisingly, we found a prominent, consistent increase in the predictive power in packets whose center frequency was located between 60 and 100 Hz (FIG. 16), that is, at the high end of the frequency spectrum, for both men and women. This band was somewhat wider for women. Also surprisingly, there was a sharp decline in the predictive power of WP crystals with $f_c$ between 10 and 50 Hz, at least for men. We conclude that the most energetic microscopic vibrations that one finds in a contracting muscle are not necessarily the vibrations that contribute the most to the effort that a muscle generates.

Figure 17:
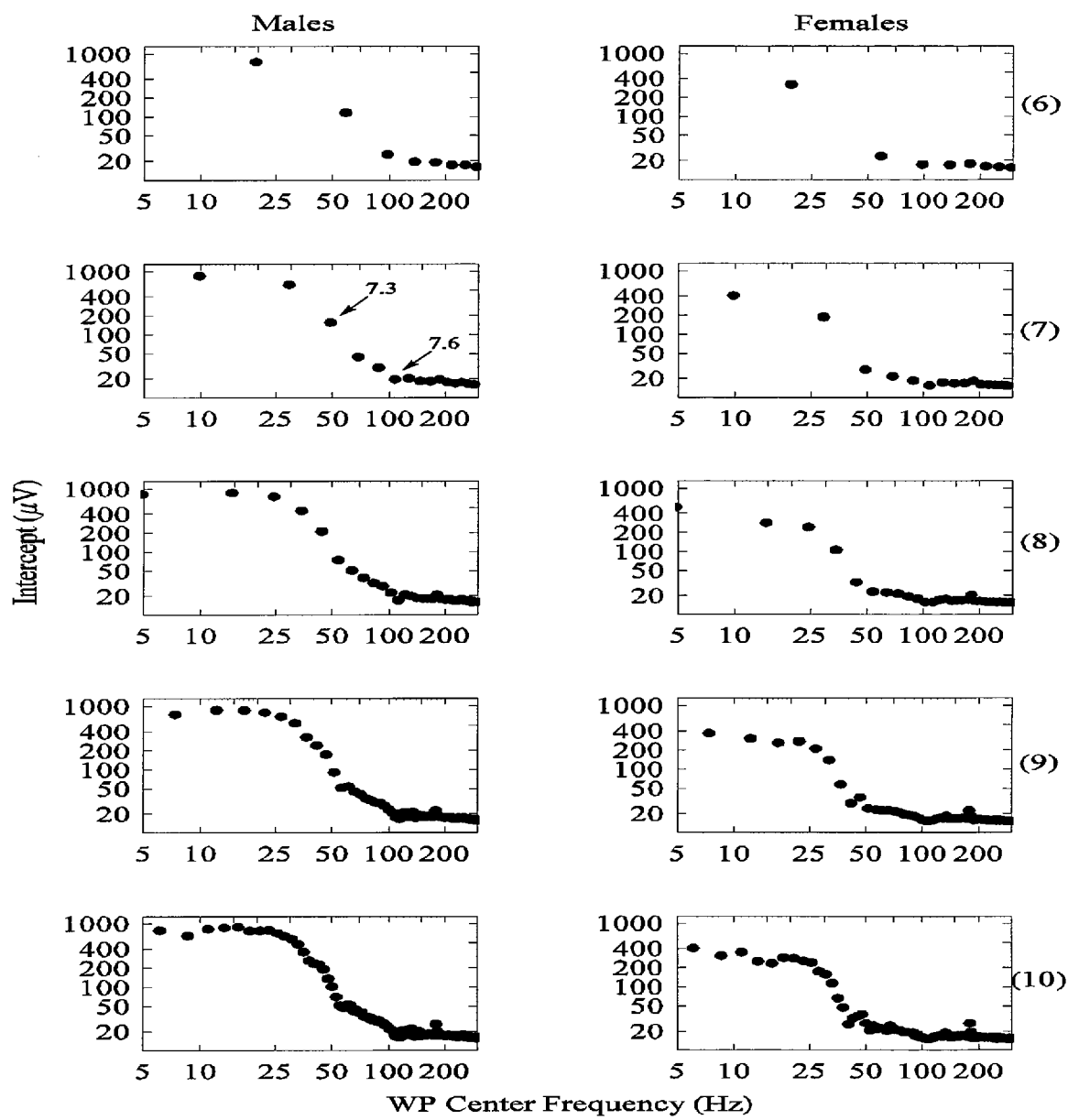
FIG. 17. Intercept parameters from the linear $EFF^2$ vs. wavelet packet amplitude regressions, plotted against center frequency of wavelet packets ($f_c$). Both axes are on log scale. Integers at right (in parentheses) indicate the number of wavelet decompositions applied to the VMG signal to provide the wavelet packet information.

Intercept parameter estimates from $EFF^2$ vs. WP crystal amplitude regressions exhibit a Lorentzian-type distribution [16] with a cut-off frequency of about 45 Hz in each level of decomposition (FIG. 17).

Figure 18:
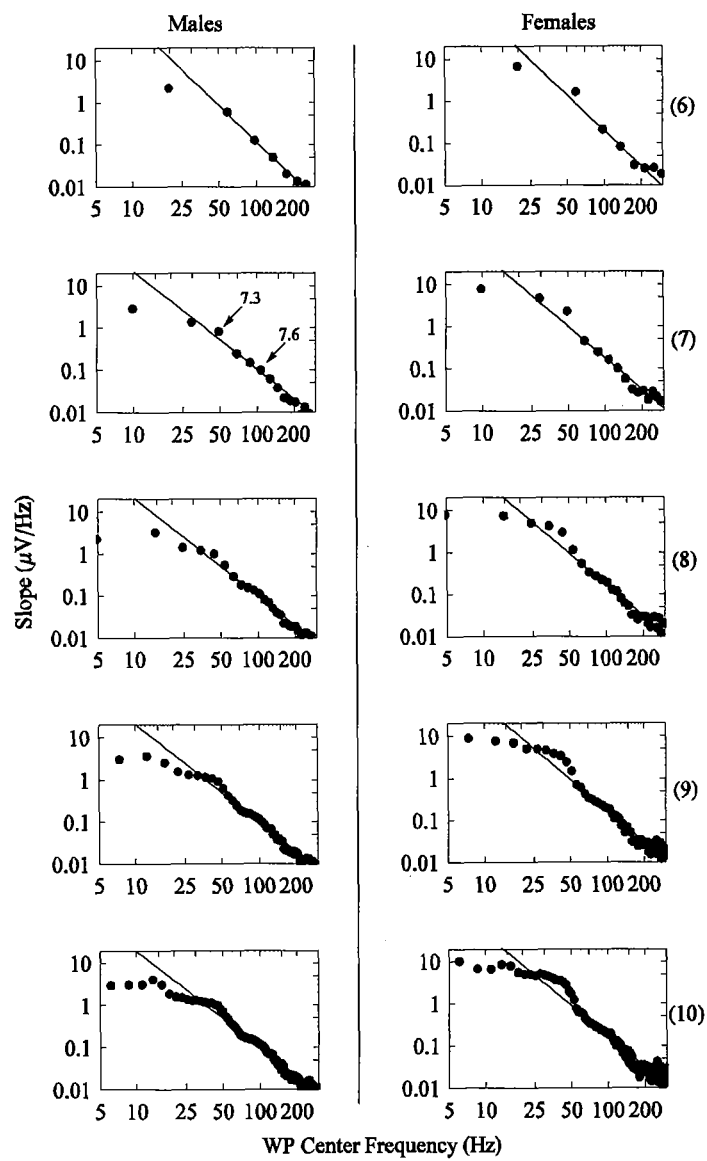
FIG. 18. Slope parameters of FIG. 15 fitted to a power-law function (y=a*x$^\alpha$) between $f_c$=50 Hz and $f_c$=300 Hz. All slopes were significantly greater than zero (p<0.001). Parameters a and α of the power-law function are shown in Table III.

There was measurable acceleration data at the skin surface at near zero EFF evident in every WP crystal, at all levels of decomposition (p<0.001). Slope parameters decreased in both male and female populations in a power law-like manner with increasing $f_c$ above 50 Hz (FIG. 18).

Sensitivity of WP crystals to EFF decreased in a consistent fashion above 50 Hz, independent of the number of WP decompositions. The specificity of WP crystals beyond 6 decompositions was similarly consistent (Table III).

Figure 19:
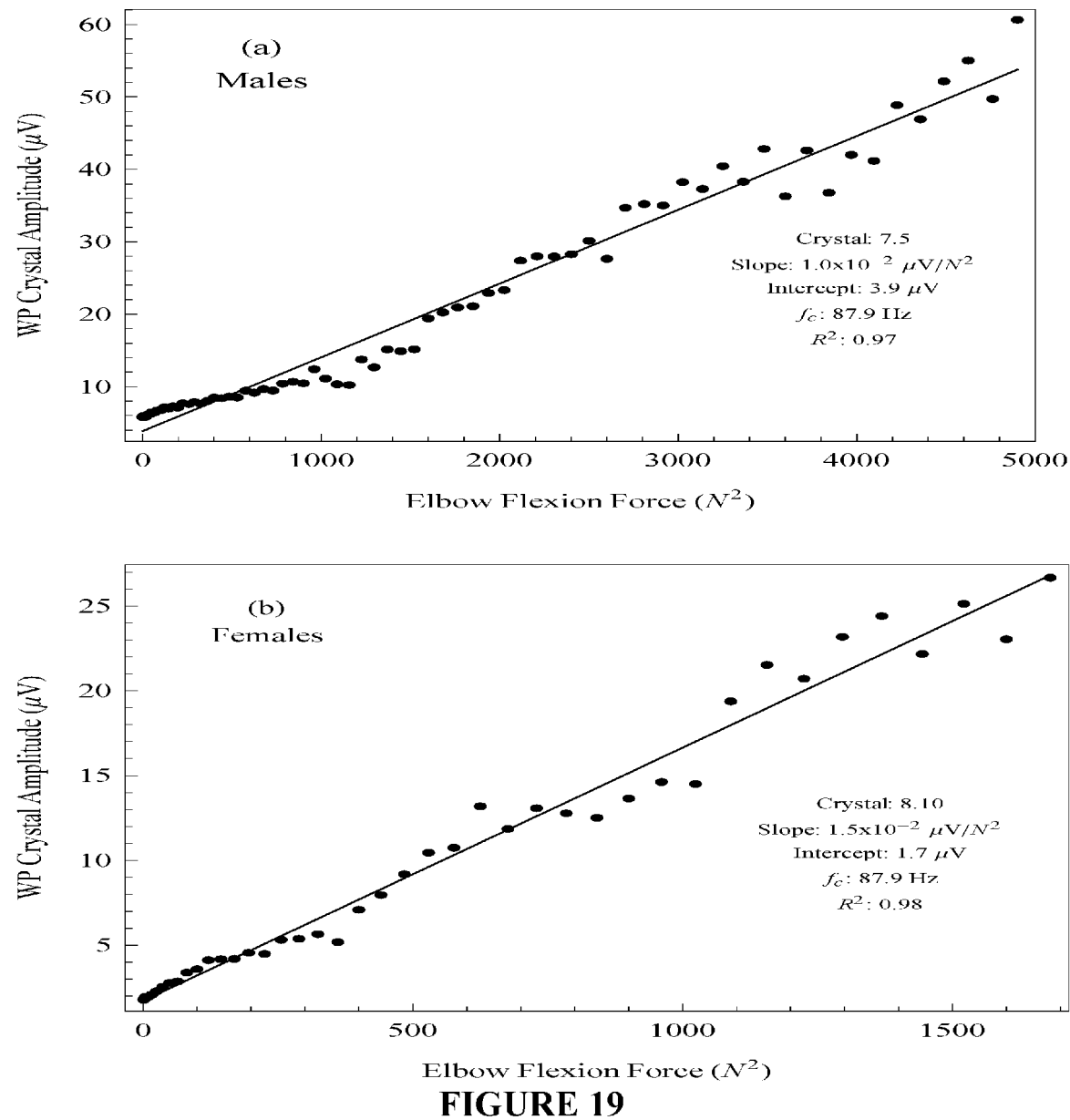
FIG. 19. Linear regression between $EFF^2$ and the single wavelet packet-modulated signal amplitude that resulted in the largest coefficient of determination.

Although at different levels of decomposition, the ability of bootstrapped amplitude estimates from WP crystals to predict absolute $EFF^2$ peaked at 87.9 Hz in both men (WP crystal 7.5, $R^2$=0.973) and women (WP crystal, 8.10, $R^2$=0.978). Further, the parameters of these regressions were different between genders, with higher specificity and sensitivity for women (FIG. 19).

Discussion

We have shown that during static DCER contractions, absolute EFF can be estimated using the amplitude of a single WP crystal from VMG data taken from the brachioradialis. Crystals with the most predictive power for both men and women, although they have a common center frequency of about 90 Hz. However, other WP crystals with center frequencies between 60 and 100 Hz also have predictive power. Further, WP crystals transition from low to high specificity for EFF as $f_c$ increases beyond 45 Hz.

TABLE III

Parameters from the power-law fits, shown in FIG. 18, between sensitivity of the force prediction measurement and $f_c$. The "α" parameters are consistent between genders, and the "a" parameters are relatively stable in decompositions 7-10.

| Number of decompositions | Males a | Males α | Females a | Females α |
|---|---|---|---|---|
| 6 | 57.46 | -2.84 | 79.10 | -2.80 |
| 7 | 4.59 | -2.32 | 16.40 | -2.48 |
| 8 | 4.42 | -2.32 | 15.01 | -2.47 |
| 9 | 4.32 | -2.32 | 14.65 | -2.47 |
| 10 | 3.63 | -2.28 | 11.62 | -2.42 |

Optimization, in the sense of identifying the best WP filter for a particular application, is necessarily application-specific: The application will dictate the appropriate trade offs between the need for accuracy, sensitivity and noise attenuation properties of a measurement made by the application of a WP filter(s) to VMG data. These properties can be examined by the use of coefficient of determination, slope and intercept parameters of the VMG WP RMS versus $EFF^2$ regression analyses, respectively, and maximizing a function of all three. For example, a function such as $$\frac{\text{slope}}{(1-R^2)*\text{Intercept}} \quad (5)$$

gives equal weight to specificity, sensitivity, and coefficient of determination in measuring flexion force, and thus could advantageously be used to choose the best sub-band for measurement of flexion force in a general case. In specific applications, the contribution from each variable can then easily be weighted in a manner which can be decided upon according to application.

The trade-off between time and frequency localization is predetermined in the decimated discrete dyadic WP transform used in this study. As such, the results presented here represent a coarse sweep of the possible solutions to band-limiting VMG data for the purposes of estimating muscle activity or forces exerted as a result of their activity. Windowed-sinc filters, for example, offer nearly arbitrary design flexibility with limitless frequency response, roll-off and phase characteristics. These filters are created by sampling the sinc(x) function, sin(x)/x, between $-\pi<x<\pi$ and multiplying by a windowing function, commonly the Hann or Hamming window. A person of skill in the art may wish to select one or more of these or other well-known filter variations to yield better estimates of optimal filter characteristics for the analysis of particular VMG signals.

In a muscle strength training application for example, an absolute measure of the net force generated by a muscle may be highly advantageous only when lifting a very heavy weight. In this case, background noise may be established at a level which permits optimizing the $R^2$ of the fit at high activation levels only. However, in an application involving assessment of the balance of muscle usage, such as in a post-injury rehabilitation or injury prevention setting, background noise and sensitivity may be lesser factors.

Persons of skill in the art will recognize that any diagnostic tool fashioned from embodiments of the present invention will require testing and validation on independent data sets, by k-fold cross-validation, for example, where data sets would be randomly assigned to the training or validation group.

The remarkable correlations between wavelet packet amplitudes and load force in our sample population provide only one example of the utility of certain embodiments of the invention. It will be understood that additional practice will more precisely ascertain the degree to which this relationship holds true for specific age, athletic ability, or ethnic groups. Practice involving other muscles will address the influence of varying joint angles and the introduction of fatigue. It is likely, for example, that different (unique) VMG data components will be found which are relatively unaffected by muscle fiber arrangement. Additionally, the precision of such measurements will become better known. Such findings will likely reveal other useful embodiments of the invention, including means of assessing muscle force development and effort in rapid or extensive motions where data acquisition time becomes short relative to the number of data points needed for analysis.

Conclusion

These findings are consistent with the view that select components of VMG signals, identified via wavelet packet analysis, have significant voluntary contractile muscle force resolving power particularly in the 80 to 100% MVC region. We have identified components of myographic signals collected from the brachioradialis with an accelerometer during static DCEM exercise that exhibit a reliable, monotonic correlation to force. Further, this relationship is based on absolute load force and is not normalized to 100% maximum voluntary contraction levels (MVC) of the subject, making it useful when conditions do not allow for collection of representative 100% MVC data.

Example 2

Wavelet Packet Analysis of VMG During Motion.

A micro-electro-mechanical accelerometer was utilized as the muscle vibration sensor. A Kistler™ Model 8305A, which has a working range of about ±2 g (g=9.8 m/s$^2$) over a 500 Hz bandwidth; sensitivity of 500 mV/g, and noise density of 20 µg/Hz$^{1/2}$ was used. In one case, the noise floor, i.e., the square root of required bandwidth times the noise density, was <300 µg. To achieve even lower noise floors, the Silicon Devices Model 1221L-002 accelerometer was used.

Closed chain activities typically involve large limb and muscle motions. An accelerometer attached to the skin above a muscle body undergoing assessment will detect such motions, but they only mask the small, high frequency vibrations that embodiments of the present invention utilize to directly assess muscle effort. A generally advantageous step in obtaining reproducible closed chain muscle effort evaluations using VMG, therefore, is the suppression of the various high energy "motion artifacts" inherent to closed chain activities. High energy vibrations arise from a variety of physiologic processes. One type of artifact is the macroscopic motion of the muscle body upon initiation of contraction. Such macroscopic motion artifacts are exemplified in FIG. 4, which shows a VMG recording (high pass filtered at 8 Hz to remove the very low frequency accelerations associated with limb motion) from the biceps of a relaxed upper arm. A broad band of high amplitude spectral components is evident up to 30 Hz as a result of macroscopic motion of the muscle. Muscle tremor (oscillating motions of the muscle body), generally occurring in the 8-12 Hz region, is another source of motion artifact (FIG. 5). A third type of high energy artifact is "impact spikes" that occur at the start of a motion when an extremity makes contact with a constraining surface. Indeed, all of the high energy components of the vibration spectrum are "artifacts" in the context of the invention in its various embodiments. As noted above, the objective, in contrast to the guidance generally provided in the VMG literature, is to remove these components in order to focus the analysis on the underlying low energy, higher frequency vibrations.

An additional type of motion artifact is associated with the movement of the skin relative to the underlying muscle body. While the common assumption among practitioners of VMG (or MMG) is that restraint of the accelerometer will suppress the vibration signal (which is correct if one is trying to pick up the lower frequency, high energy signal components) the applicants, who focus on the higher frequency, low energy components of the VMG signal, have found that compression of the accelerometer against the muscle body significantly enhances the recording of the vibrations of interest. The vibromyographic sensor was held against the skin over the muscle group of interest by means of an elastic strap. The material is capable of repeatedly experiencing a percent strain of 25-50% and returning to its original length. It is non-allergenic and washable. It is sufficiently wide (e.g., 8-12 cm for the vastus lateralis) that the muscle body is compressed after application, and sufficiently long (e.g. 50-150 cm for recording from muscles of the thigh) to permit at least one full wrap around the limb or body segment under investigation. The material has a low coefficient of elasticity.

To remove high energy vibrational components associated with macroscopic muscle motion or skin motion in order to extract the low level, high frequency components of the VMG, the raw accelerometer output was filtered through a high pass analog input filter having a cutoff frequency near 30 Hz. All pre-processing steps were performed with a Krohn-Hite Corporation Model 3944 Multichannel Filter. A minimal (i.e. one-pole) filter is required prior to any analog to digital (A/D) conversion. In this example, a three pole, 30 Hz, high pass analog input filter was used. The output of the high pass filter was amplified in order to minimize the influence of noise acquired during the analog to digital conversion step. Amplification by a gain of 20× was employed to utilize the full range of a 16 bit A/D converter (the Linear Technology Corp. LTC2450, a 16-bit delta sigma A/D converter). The amplified signal was low-pass filtered at a cutoff frequency of 360 as an anti-aliasing measure to prevent the introduction of digitization artifacts prior to sampling at 5 KHz.

The Wavelet Toolbox™ software available from MATLAB® provided graphical tools and command-line functions needed for developing wavelet-based algorithms for the analysis of vibromyographic data, along with the ability to perform regression analysis. FIG. 6 illustrates the results of one such set of experiments. Each wavelet packet was identified by the center frequency of the power spectrum of the signal sub-band which best matched the packet's wavelet function. In this example, Daubechies Maximum Flat or "extremal phase" mother wavelets of order 1-16 were used. The VMG signals were sampled at 5 kHz.

The regression coefficient between measured load force and the magnitude of the envelope of the calculated analytic function associated with a VMG signal was obtained by linear regression analysis. The coefficient provides a calibration, or scaling, factor which can be used to convert the wavelet packet amplitude to a measure of muscle effort. Wavelet packets having frequency spectra that overlapped with the vibration frequencies associated with a contraction of a muscle of interest were of particular interest. The frequency content of the wavelet packets which provided the highest levels of correlation tended to be in the 40-150 Hz range.

In the present example, for VMG data sampled at 5 KHz, the best performing wavelet packets were found to be 6.3, 7.4 and 8.8. Note that when using Daubechies mother wavelets, orders less than 8 provide better correlations than higher order mother wavelets. For VMG data sampled at 500 Hz, which is advantageous in the development of a multichannel device to be used in real time applications, the best correlations with load force were found to be wavelet packets 2.2, 3.3, 4.4 and 4.5, that is, packets generated with a small number of decompositions ("x") and associated with sub-bands having center frequencies at the higher end of the muscle vibrational frequency spectrum ("y"), in contradistinction to what is reported in the prior art.

Following the high-pass filtering and amplifications steps described above, the digitized vibromyographic signal was conditioned for wavelet packet analysis by low pass filtering at 225 Hz in order to prevent aliasing during digitization. The low-pass filtered signal was then down-sampled to 500 Hz to enhance the speed of the wavelet packet analysis. In this example, the $3^{rd}$ order Daubechies wavelet packet 4.4 was chosen to provide a wavelet-packet representation of muscle effort as a function of time. The VMG signal was subjected to four levels of decomposition in the filter bank. When applied to a VMG signal sampled at 500 Hz, a transformed signal sampled at 31.25 Hz was obtained. After the decomposition, (utilizing, in this case, maximally flat FIR filtering), the analytic function of the wavelet packet representation was obtained. This was accomplished by computing the Hilbert transform of the wavelet packet data. Next, the absolute value of the analytic signal (real plus 90 degree phase shifted signal) was computed using the square root of the sum of squares, then low pass filtered to estimate the amplitude of the envelope of the wavelet packet data.

Next, the envelope amplitude data were converted to values in force units (lbs) by multiplying envelope values by a calibration factor obtained empirically, as described above. Muscle effort relations were acquired by gathering joint kinematics data in combination with load or torque measurements. A dynamometer was used to measure torque. While any joint can be utilized to obtain the calibration factor, simple geometries such as those that exist for the triceps insertion onto the ulna are the most direct and were used here. The values obtained were then correlated with the VMG envelope amplitude data so that muscle effort could be expressed in units of force.

Although the envelope-force relation for each musculoskeletal system (e.g. ankle, knee, elbow, shoulder, etc) is expected to be different to a degree, average values may be acquired empirically for each system in the database contemplated hereinabove.

Example 3

Calibration Factor Obtained for SDI Model 1221L-002 (+/−2 g) Accelerometer Chip

To find a calibration factor for use in expressing VMG muscle effort data in terms of force units, subjects in supine position, forearm parallel to floor, upper arm perpendicular to floor. An SDI model 1221 L-002 accelerometer was pressed against the triceps muscle according to an embodiment of the invention. Accelerometer data were acquired and processed as described above during contractions against loads of 0-22.5 lbs. Load forces on the triceps were computed by treating the elbow as fulcrum and the forearm as lever.

Regression analysis of the relationship between measured load force and the magnitude of the envelope of the wavelet packet-analyzed vibromyographic data acquired from each of 4 males (where a value >two standard deviations above the envelope mean was defined as the characteristic magnitude) was performed. The results, shown in FIG. 20, indicate that VMG conversion factor equals about 300 lbs.

REFERENCES

[1] O. Lammert, F. Jorgenson, N. Einer-Jenson, "Accelerometermyography (AMG). I: Method for measuring mechanical vibrations from isometrically contracted muscles," Biomechanics V-A, pp. 152-158, 1976.

[2] R. Merletti, P. A. Parker, Electromyography: Physiology, Engineering, and noninvasive Applications. Piscataway, N.J.: IEEE Press, 2004, pp. 305-318.

[3] C. Orizio, D. Liberati, C. Locatelli, D. De Grandis, A. Veicsteinas, "Surface mechanomyogram reflects muscle fibres twitches summation," J. Biomechanics, vol. 29(4), pp. 475-481, 1996.

[4] Y. Yoshitake, T. Moritane, "The muscle sound properties of different muscle fiber types during voluntary and electrically induced contractions," J. Electromyog Kinesiol, vol. 9, pp. 209-217, 1999.

[5] M. Petitjean, B. Maton, "Phonomyogram from single motor units during voluntary isometric contraction," Eur. J. Appl. Physiol., vol. 71, pp. 215-222, 1995.

[6] J. Basmajian, C. De Luca, Muscles alive. Baltimore, Md.: Waverly Press, Inc, 1985.

[7] K. Akataki, K. Mita, Y. Itoh, "Relationship between mechanomyogram and force during voluntary contractions reinvestigated using spectral decomposition," Eur. J. Appl. Physiol., vol. 80, pp. 173-179, 1999.

[8] K. Akataki, K. Mita, M. Watakabe, K. Itoh, "Mechanomyogram and force relationship during voluntary isometric ramp contractions of the biceps brachii muscle," Eur. J. Appl. Physiol., vol. 84, pp. 19-25, 2001.

[9] K. Ebersole, T. Housh, G. Johnson, T. Evetovich, D. Smith, S. Perry, "The effect of leg flexion angle on the mechanomyographic responses to isometric muscle actions," Eur. J. Appl. Physiol. Occup. Physiol., vol. 78(3), pp. 264-269, 1998.

[10] D. Denoho, "De-noising by soft-thresholding," IEEE Trans. Informat. Theory, vol. 41, pp. 613-627, 1995.

[11] H. Gao, "Choice of thresholds for wavelet shrinkage estimate of the spectrum," J. Time Series Anal., vol. 18, pp. 231-251, 1997.

[12] K. Akataki, K. Mita, Y. Itoh, "Repeatability study of mechanomyography in submaximal isometric contractions using coefficient of variation and interclass correlation coefficient," Electromyogr. Clin. Neurophysiol., vol. 39, pp. 161-166, 1999.

[13] M. Kouzaki, M. Shinohra, T. Fukunaga, "Non-uniform mechanical activity of quadriceps muscle during fatigue by repeated maximal voluntary contraction in humans," Eur. J. Appl. Physiol., vol. 80, pp. 9-15, 1999.

[14] G. O. Matheson, L. Maffey-Ward, M. Mooney, K. Ladly, T. Fung, Y-T. Zhang, "Vibromyography as a quantitative measure of muscle force production," Scand. J. Rehab. Med., vol. 29, pp. 29-35, 1997.

[15] B. Maton, M. Petitjean, J. C. Cnockaert, "Phonomyogram and electromyogram relationships with isometric force reinvestigated in man," Eu. J. Appl. Physiol., vol. 60, pp. 194-201, 1990.

[16] L. J. DeFelice, Introduction to membrane noise. New York, Plenum Press, 1981, pp 291.

[17] C. J. DeLuca, R. S. LeFever, M. P. McCue, A. P. Xenakis, "Behavior of human motor units in different muscles during linearly varying contractions," *J. Physiol.*, vol. 329, pp. 113-128, 1982.

We claim:

1. A kit for assessment of a muscle effort, comprising:
   a. a vibromyographic sensor comprising:
      i. an accelerometer configured to detect microscopic muscle vibrations as vibromyographic signals; and
      ii. a wave filter configured to create a de-noised signal;
   b. a software program stored on a non-transient computer readable medium for execution by a processor, the program comprising instructions for identifying absolute muscle effort determinants comprising a monotonic correlation over an 80%-100% of maximal voluntary contraction of said microscopic muscle vibrations from said de-noised signal by detecting a wavelet packet envelope wherein said muscle effort determinant comprises a plurality of peak envelope values; and
   c. instructions for using said vibromyographic sensor and said software program.

2. The kit of claim 1 wherein said wavelet packet envelope is detected within said de-noised signals.

3. The kit of claim 2, wherein said wavelet packet envelope comprises analytic wavelet packets, wherein said packets are created by convolving said signal with a wavelet.

4. The kit of claim 2, wherein said wavelet packet envelope comprises a center frequency located between 60 and 100 Hz.

5. The kit of claim 1, wherein said absolute muscle effort determinant comprises peak muscular force.

6. The kit of claim 1, further comprising a means for pressing said accelerometer against a muscle body.

7. The kit of claim 1, further comprising a high bandpass filter.

8. The kit of claim 1, further comprising an amplifier.

9. The kit of claim 1, wherein said wave filter suppresses essentially all frequencies greater than 0 Hz and less than 40 Hz from said vibromyographic signals.

10. The kit of claim 1, wherein said vibromyographic sensor further comprises a sealed transducer.

* * * * *